US008618066B1

(12) United States Patent
McDaniel

(10) Patent No.: US 8,618,066 B1
(45) Date of Patent: *Dec. 31, 2013

(54) COATING COMPOSITIONS HAVING PEPTIDIC ANTIMICROBIAL ADDITIVES AND ANTIMICROBIAL ADDITIVES OF OTHER CONFIGURATIONS

(75) Inventor: C. Steven McDaniel, Austin, TX (US)

(73) Assignee: Reactive Surfaces, Ltd., LLP, Austin, TX (US)

(*) Notice: Subject to any disclaimer, the term of this patent is extended or adjusted under 35 U.S.C. 154(b) by 1359 days.

This patent is subject to a terminal disclaimer.

(21) Appl. No.: 11/865,514

(22) Filed: Oct. 1, 2007

Related U.S. Application Data

(63) Continuation-in-part of application No. 10/884,355, filed on Jul. 2, 2004, now abandoned.

(60) Provisional application No. 60/827,531, filed on Sep. 29, 2006, provisional application No. 60/485,234, filed on Jul. 3, 2003.

(51) Int. Cl.
  *A61K 38/00* (2006.01)
  *A61K 38/08* (2006.01)
  *A61K 38/10* (2006.01)
  *A61K 31/74* (2006.01)
  *C07K 7/00* (2006.01)
  *C07K 17/00* (2006.01)
  *A01N 25/00* (2006.01)

(52) U.S. Cl.
  USPC ........ 514/21.4; 514/21.5; 514/21.8; 530/326; 530/327; 530/329; 424/78.09; 424/404

(58) Field of Classification Search
  None
  See application file for complete search history.

(56) References Cited

U.S. PATENT DOCUMENTS

| | | | |
|---|---|---|---|
| 4,342,751 A | 8/1982 | Moore et al. | |
| 4,935,351 A | 6/1990 | Yamane et al. | |
| 5,177,012 A | 1/1993 | Kim et al. | |
| 5,482,996 A | 1/1996 | Russell et al. | |
| 5,602,097 A | 2/1997 | Edwards | |
| 5,646,014 A | 7/1997 | Hara | |
| 5,882,731 A | 3/1999 | Owens | |
| 5,885,782 A | 3/1999 | Edwards | |
| 5,919,689 A | 7/1999 | Selvig et al. | |
| 5,998,200 A | 12/1999 | Bonaventura et al. | |
| 6,020,312 A | 2/2000 | Edwards | |
| 6,054,504 A | 4/2000 | Dalla Riva Toma | |
| 6,294,183 B1 | 9/2001 | Ito et al. | |
| 6,642,037 B2 | 11/2003 | Gordon et al. | |
| 6,730,144 B2 | 5/2004 | Tanaka et al. | |
| 6,858,581 B2 * | 2/2005 | Kuhner et al. | 514/2.4 |
| 7,041,285 B2 | 5/2006 | Polsenski et al. | |
| 7,125,842 B2 | 10/2006 | Kawabe et al. | |
| 7,238,669 B2 | 7/2007 | Bishop-Hurley et al. | |
| 7,335,400 B2 | 2/2008 | Russell et al. | |
| 2002/0010228 A1 | 1/2002 | Simendinger, III | |
| 2002/0010229 A1 | 1/2002 | Medoff et al. | |
| 2002/0013385 A1 | 1/2002 | Simendinger, III | |
| 2002/0035239 A1 | 3/2002 | Andersen et al. | |
| 2002/0106361 A1 | 8/2002 | Poulsen et al. | |
| 2002/0132540 A1 | 9/2002 | Soerens et al. | |
| 2003/0047508 A1 | 3/2003 | Boles et al. | |
| 2003/0050247 A1 * | 3/2003 | Kuhner et al. | 514/16 |
| 2003/0166237 A1 | 9/2003 | Allermann et al. | |
| 2003/0194445 A1 | 10/2003 | Kuhner et al. | |
| 2004/0109853 A1 | 6/2004 | McDaniel | |
| 2004/0175407 A1 | 9/2004 | McDaniel | |
| 2004/0248783 A1 | 12/2004 | Kawabe et al. | |
| 2005/0147579 A1 | 7/2005 | Schneider et al. | |
| 2006/0160200 A1 | 7/2006 | Rathenow et al. | |
| 2008/0119381 A1 | 5/2008 | Wang et al. | |

FOREIGN PATENT DOCUMENTS

| | | |
|---|---|---|
| EP | 1174439 | 1/2002 |
| WO | 94/01459 | 1/1994 |
| WO | 95/08341 | 3/1995 |
| WO | 97/21805 | 6/1997 |
| WO | 01/72911 | 10/2001 |
| WO | 02/064183 | 8/2002 |
| WO | 2004/055044 | 7/2004 |

OTHER PUBLICATIONS

Nolla-Sala, J., et al. 1992 Clinical Infectious Diseases 14: 952-4.*
Mak et al., "Isolation, Antimicrobial Activities, and Primary Structures of Hamster Neutrophil Defensins," Infection & Immunity, Nov. 1996, pp. 4444-4449.
Mandard et al., "The solution structure of gomesin, an antimicrobial cysteine-rich peptide from the spider," Eur. J. Biochem., vol. 269, 2002, pp. 1190-1198.
Martins et al., "1H NMR Study of the Solution Structure of Ac-AMP2, a Sugar Binding Antimicrobial Protein Isolated from Amaranthus caudatus," J. Mol. Biol., vol. 258, 1996, pp. 322-333.
Moerman et al., "Antibacterial and antifungal properties of α-helical, cationic peptides in the venom of scorpions from southern Africa," Eur. J. Biochem., vol. 269, 2002, pp. 4799-4810.
Moore et al., "Antimicrobial Peptides in the Stomach of *Xenopus laevis*," The Journal of Biological Chemistry, vol. 266, No. 29, Oct. 1991, pp. 19851-19857.
Mor et al., "Isolation and structure of novel defensive peptides from frog skin," Eur. J. Biochem. vol. 219, 1994, pp. 145-154.

(Continued)

*Primary Examiner* — Marsha Tsay
(74) *Attorney, Agent, or Firm* — McDaniel & Associates, P.C.

(57) ABSTRACT

Coating compositions having a peptidic antimicrobial additive and an antimicrobial additive of another configuration are provided. The concentrations of the antimicrobial agents within the coating composition are sufficient to synergistically inhibit microbial growth on an inanimate surface coated with the surface coating composition or within a container storing the coating composition. Methods for making and using such compositions to inhibit microbial growth in stored coatings and on susceptible surfaces are also provided.

2 Claims, 1 Drawing Sheet

(56) References Cited

OTHER PUBLICATIONS

Mor et al., "Skip peptide tyrosine-tyrosine, a member of the pancreatic polypeptide family: Isolation, structure, synthesis, and endrocrine activity," Proc. Natl. Acad. Sci. USA, vol. 91, Oct. 1994, pp. 10295-10299.

Nagaoka et al., "Characterization of cDNA clones encoding guinea pig neutrophil cationic peptides," FEBS, vol. 280, No. 2, Mar. 1991, pp. 287-291.

Olson III et al., "Pseudin-2: An Antimicrobial Peptide with Low Hemolytic Activity from the Skin of the Paradixical Frog," Biochem. & Biophys. Res. Comm., vol. 288, 2001, pp. 1001-1005.

Oppenheim et al., "Histatins, a Novel Family of Histidine-rich Proteins in Human Parotid Secretion," The Journal of Biological Chemistry, vol. 263, No. 16, Jun. 1988, pp. 7472-7477.

Orivel et al., "Ponericins, New Antibacterial and Insecticidal Peptides from the Venom of the Ant *Pachycondyla goeldii*," The Journal of Biological Chemistry, vol. 276, No. 21, May 2001, pp. 17823-17829.

Park et al., "Antimicrobial Peptides from the Skin of a Korean Frog, *Rana rugosa*," Biochem. & Biophys. Res. Comm., vol. 205, No. 1, Nov. 1994, pp. 948-954.

Park et al., "A Novel Antimicrobial Peptide from *Bufo bufo gargarizans*," Biochem. & Biophys. Res. Comm., vol. 218, 1996, pp. 408-413.

Park et al., "Structural study of novel antimicrobial peptides, nigrocins, isolated from *Rana nigromaculata*," FEBS Letters, vol. 507, 2001, pp. 95-100.

Park et al., "A novel antimicrobial peptide from the loach, *Misgurnus anguillicaudatus*," FEBS Letters, vol. 411, 1997, pp. 173-178.

Raj et al., "Structure of Human Salivary Histatin 5 in Aqueous and Nonaqueous Solutions," Biopolymers, vol. 45, 1998, pp. 51-67.

Tailor et al., "A Novel Family of Small Cysteine-rich Antimicrobial Peptides from Seed of *Impatiens balsamina* is Derives from a Single Precursor Protein," The Journal of Biological Chemistry, vol. 272, No. 39, Sep. 1997, pp. 24480-24487.

Rebuffat et al., "Trichologins BI and BII, 19-residue peptaibols from *Trichoderma longibrachiatum*," Eur. J. Biochem., vol. 201, 1991, pp. 661-674.

Robinette et al., "Antimicrobial activity in the skin of the channel catfish *Ictalurus punctatus*: characterization of broad-spectrum histone-like antimicrobial proteins," CMLS, vol. 54, 1998, pp. 467-475.

Rozek et al., "Structure of the Bovine Antimicrobial Peptide Indolicidin Bound to Dodecylphosphocholine and Sodium Dodecyl Sulfate Micelles," Biochemistry, vol. 39, 2000, pp. 15765-15774.

Rozek et al., "The antibiotic and anticancer active aurein peptides from the Australian Bell Frogs *Litoria aurea* and *Litoria raniformis*," Eur. J. Biochem. vol. 267, 2000, pp. 5330-5341.

Ruissen et al., "Histatin 5 and derivatives: Their localization and effects on the ultra-structural level," Peptides, vol. 23, 2002, pp. 1391-1399.

Schibli et al., "Structure of the Antimicrobial Peptide Tritrpticin Bound to Micelles: A Distinct Membrane-Bound Peptide Fold," Biochemistry, vol. 38, 1999, pp. 16749-16755.

Schonwetter et al., "Epithelial antibiotics induced at sites of inflammation," Science, vol. 267, No. 5204, Mar. 1995, pp. 1645-1648.

Scocchi et al., "Structural organization of the bovine cathelicidin gene family and identification of a novel member," FEBS Letters, vol. 417, 1997, pp. 311-315.

Selsted et al., "Primary Structures of MCP-1 and MCP-2, Natural Peptide Antibiotics of Rabbit Lung Macrophages," The Journal of Biological Chemistry, vol. 258, No. 23, Dec. 1983, pp. 14485-14489.

Skerlavaj et al., Biological Characterization of Two Novel Cathelicidin-derived Peptides and Identification of Structural Requirements for Their Antimicrobial and Cell Lytic Activities, The Journal of Biological Chemistry, vol. 271, No. 45, Nov. 1996, pp. 28375-28381.

Tang et al., "Isolation, Characterication, cDNA Cloning, and Antimicrobial Properties of Two Distinct Subfamilies of α-Defensins from *Rhesus macaque* Leukocytes," Infection & Immunity, vol. 67, No. 11, Nov. 1999, pp. 6139-6144.

Terras et al., "A new family of basic cysteine-rich plant antifungal proteins from *Brassicaceae* species," FEBS, vol. 316, No. 3, Feb. 1993, pp. 233-240.

Tinoco et al., "NMR Structure of PW2 Bound to SDS Micelles," The Journal of Biological Chemistry, vol. 277, No. 39, Sep. 2002, pp. 36351-36356.

Ueta et al, "A novel bovine lactoferrin peptide, FKCRRWQWRM, suppresses Candida cell growth and activates neutrophils," J. Peptide Res., vol. 57, 2001, pp. 240-249.

Vogel et al., "Towards a structure-function analysis of bovine lactoferricin and related tryptophan- and arginine-containing peptides," Biochem. Cell Biol., vol. 80, 2002, pp. 49-63.

International Search Report, PCT/US2004/021711, mailed Feb. 23, 2005.

Wang et al., "Ginkbilobin, a Novel Antifungal Protein from *Ginkgo biloba* Seeds with Sequence Similarity to Embryo-Abundant Protein," Biochem. & Biophys. Res. Comm., vol. 279, 2000, pp. 407-411.

Wang et al., "Novel Antifungal Peptides from Ceylon Spinach Seeds," Biochem. & Biophys. Res. Comm., vol. 288, 2001, pp. 765-770.

Wilde et al., "Purification and Characterization of Human Neutrophil Peptide 4, a Novel Member of the Defensin Family," The Journal of Biological Chemistry, vol. 264, No. 19, Jul. 1989, pp. 11200-11203.

Yi et al., "Solution structure of an antimicrobial peptide buforin II," FEBS Letters, vol. 398, 1996, pp. 87-90.

Yin et al., "Physical parameters of hydroxyapatite adorption and effect on candidacidal activity of histatins," Archives of Oral Biology, vol. 48, 2003, pp. 361-368.

Zhang et al., "NMR Studies of Defensin Antimicrobial Peptides: 1. Resonance Assignment and Secondary Structure Determined of Rabbit NP-2 and Human HNP-1," Biochemistry, vol. 31, 1992, pp. 11348-11356.

Zhao et al., "Identification of a new member of the protegrin family by cDNA cloning," FEBS Letters, vol. 346, 1994, pp. 285-288.

Zhao et al., "The structure of porcine protegrin genes," FEBS Letters, vol. 368, 1995, pp. 197-202.

Zhu et al., "Isolation and Mode of Action of Rabbit Corticostatic (Antiadrenocorticotropin) Peptides," Endocrinology, vol. 130, No. 3, 1992, pp. 1413-1423.

Zimmermann et al., "Solution Structure of Bovine Neutrophil β-Defensin-12: The Peptide Fold of the β-Defensin is Identical to that of the Classical Defensins," Biochemistry, vol. 34, 1995, pp. 13663-13671.

Cutuli et al., "Antimicrobial effects of α-MSH peptides," Journal of Leukocyte Biology, vol. 67, Feb. 2000, pp. 233-239.

Destoumieux et al., "Penaeidins, a family of antimicrobial peptides from penaeid shrimp (Crustacea, Decapoda)," CMLS, vol. 57, 2000, pp. 1260-1271.

Fiedler et al., "Nikkomycins: Microbial Inhibitors of Chitin Synthase," J. Chem. Tech. Biotechnol., vol. 32, 1982, pp. 271-280.

Goraya et al., "Peptides with antimicrobial activity from four different families isolated from the skins of the North American frogs *Rana luteiventris, Rana berlandieri* and *Rana pipiens*," Eur. J. Biochem., vol. 267, 2000, pp. 894-900.

Guichard et al., "Antigenic mimicry of natural L-peptides with retro-inverso-peptidomimetics," Proc. Natl. Acad. Sci. USA, vol. 91, Oct. 1994, pp. 9765-9769.

Iijima et al., "A novel antimicrobial peptide from the sea hare *Dolabella auricularia*," Developmental & Comparative Immunology, vol. 27, 2003, pp. 305-311.

Koo et al., "Two hevein homologs isolated from the seed of Pharbitis nil L. exhibit potent antifungal activity,". Biochimica et Biophysica Acta, vol. 1382, 1998, pp. 80-90.

Jones et al., "Paneth Cells of the Human Small Intestine Express an Antimicrobial Peptide Gene," The Journal of Biological Chemistry, vol. 267, No. 32, Nov. 1992, pp. 23216-23225.

Lee et al., "Purification and cDNA Cloning of an Antifungal Protein from the Hemolymph of *Holotrichia diomphalia* Larvae," Biol. Pharm. Bull., vol. 18, No. 8, 1995, pp. 1049-1052.

(56) References Cited

OTHER PUBLICATIONS

Mandard et al., "Solution structure of thanatin, a potent bactericidal and fungicidal insect peptide, determined from proton two-dimensional nuclear magnetic resonance data," Eur. J. Biochem., vol. 256, 1998, pp. 404-410.

Mandard et al., "Androctonin, a Novel Antimicrobial Peptide from Scorpion *Androctonus australis*: Solution Structure and Molecular Dynamics Simulations in the Presence of a Lipid Monolayer," Journal of Biomolecular Structure & Dynamics, vol. 17, No. 2, 1999, pp. 367-380.

Nagaoka et al., "Cloning and characterization of the guinea pig neutrophil cationic peptide-1 and -2 genes," J. DNA Sequencing & Mapping, vol. 4, 1993, pp. 123-128.

Qu et al., "Insect Immunity: Isolation and Structure of Cecropins B and D from Pupae of the Chinese Oak Silk Moth, *Antheraea pernyi*," Eur. J. Biochem., vol. 127, 1982, pp. 219-224.

Soedjanaatmadja et al., "Demonstration by mass spectrometry that pseudo-hevein and hevein have ragged C-terminal sequences," Biochimica et Biophysica Acta, vol. 1209, 1994, pp. 144-148.

Theil et al., "Purification and Spectral Characterization of Seminalplasmin, an Antimicrobial Protein from Bull Semen," Hoppe-Seyler's Z. Physiol. Chem. Bd., vol. 364, Aug. 1983, pp. 1003-1009.

Xu et al., "Primary Structure and Anticandidal Actificy of the Major Histatin from Parotid Secretion of the Subhuman Primate, *Macaca fascicularis*," J. Dent. Res., vol. 69, No. 11, Nov. 1990, pp. 1717-1723.

Yount et al., "Rat Neutrophil Defensins: Precursor Structures and Expression During Neutrophilic Myelopoiesis," The Journal of Immunology, vol. 155, 1995, pp. 4476-4484.

Zasloff et al., "Magainins, a class of antimicrobial peptides from Xenopus skin: Isolation, characterization of two active forms, and partial cDNA sequence of a precursor," Proc. Natl. Acad. Sci. USA, vol. 84, Aug. 1987, pp. 5449-5453.

Zhu et al., "Isolation and structure of corticostatin peptides from rabbit fetal and adult lung," Proc. Natl. Acad. Sci. USA, vol. 85, Jan. 1988, pp. 592-596.

Grau et al., "A Biophysical Study of the Interaction of the Lipopeptide Antibiotic Iturin a with Aqueous Phospholipid Bilayers," Archives of Biochemistry & Biophysics, vol. 377, No. 2, May 2000, pp. 315-323.

Gillatt, "Microbiological Protection of Waterborne Paint Formulations," Waterborne Coatings and Additives, © The Royal Society of Chemistry 1995, pp. 202-216.

Brunt, "A Silver Lining for Paints and Coatings—A Revolutionary Preservative System," Waterborne Coatings and Additives, © The Royal Society of Chemistry 1995, pp. 243-246.

Paints, Coatings and Solvents, Second Completely Revised Edition, Edited by Stoye and Freitag, © Wiley-VCH 1998, pp. 6, 12-19, 127, 165, 288-290.

Plueddemann, Silane Coupling Agents, © 1982 Plenum Press, pp. 224-229.

Broun et al., "Catalytic Plasticity of Fatty Acid Modification Enzymes Underlying Chemical Diversity of Plant Lipids," Science, vol. 282, 1998, pp. 1315-1317.

Devos et al., "Practical Limits of Function Prediction," Proteins: Structure, Function, and Genetics, vol. 41, 2000, pp. 98-107.

Kisselev, "Polypeptide Release Factors in Prokaryotes and Eukaryotes: Same Function, Different Structure," Structure, vol. 10, 2002, pp. 8-9.

McDaniel et al., "Enzyme-based additives for paints and coatings," Progress in Organic Coatings, vol. 55, 2006, pp. 182-188.

Seffernick et al., "Melamine Deaminase and Atrazine Chlorohydrolase: 98 Percent Identical but Functionally Different," Journal of Bacteriology, vol. 183, No. 8, 2001, pp. 2405-2410.

Whisstock et al., "Prediction of protein function from protein sequence and structure," Quarterly Review of Biophysics, vol. 36, No. 3, 2003, pp. 307-340.

Witkowski et al., "Conversion of a β-Ketoacyl Synthase to a Malonyl Decarboxylase by Replacement of the Active-Site Cysteine with Glutamine," Biochemistry, vol. 38, 1999, pp. 11643-11650.

Gordon et al., "Organophosphate skin decontamination using immobilized enzymes," Chemico-Biological Interactions, vols. 119-120, 1999, pp. 463-470.

Lejeune et al., "Fighting Nerve Agent Chemical Weapons with Enzyme Technology," pp. 153-170.

Mulchandani et al., "Detoxification of Organophosphate Nerve Agents by Immobilized *Escherichia coli* with Surface-Expressed Organophosphorus Hydrolase," 1999, pp. 216-223.

Cheng et al., "*Alteromonas prolidase* for organophosphorus G-agent decontamination," Chemico-Biological Interactions, vols. 119-120, 1999, pp. 455-462.

Elashvili et al., "phnE and glpT Genes Enhance Utilization of Organophosphates in *Escherichia coli* K-12," Applied and Environmental Microbiology, vol. 64, No. 7, 1998, pp. 2601-2608.

D'Acunzo et al., "D-Amino Acid Oxidase from *Trigonopsis variabilis*: Immobilization of Whole Cells in Natural Polymeric Gels for Glutaryl-7-Aminocephalosporanic Acid Production," Journal of Fermentation and Bioengineering, vol. 81, No. 2, 1996, pp. 138-142.

Hoskin et al., "Degradation of nerve gases by CLECS and cells: kinetics of heterogenous systems," Chemico-Biological Interactions, vols. 119-120, 1999, pp. 439-444.

Kaneva et al., "Factors Influencing Parathion Degradation by Recombinant *Escherichia coli* with Surface-Expressed Organophosphorus Hydrolase," Biotechnol. Prog., vol. 14, 1998, pp. 275-278.

Sanders et al., "Stand-off tissue-based biosensors for the detection of chemical warfare agents using photosynthetic fluorescence induction," Biosensors & Bioelectronics, vol. 16, 2001, pp. 439-446.

Richins et al., "Biodegradation of organophosphorus pesticides by surface-expressed organophosphorus hydrolase," Nature Biotechnology, vol. 15, 1997, pp. 964-987.

Kim et al., "Processing Efficiency of Immobilized Non-Growing Bacteria: Biocatalytic Modeling and Experimental Analysis," Canadian Journal of Chemical Engineering, vol. 77, 1999, pp. 883-892.

Office Action mailed Apr. 28, 2010 for U.S. Appl. No. 12/243,755.

Office Action mailed Aug. 13, 2010 for EP Patent Application No. 03816944.7.

Abstract only, JP11124521, published May 1999.

Eisenberg et al., Structure Summary Printout for 2mlt, deposited to RCSB Protein Data Bank Oct. 1990.

Bulet et al., Sequence, Function, Subunit, Subcellular Location, Tissue Induction, Mass Spectrometry, and Amidation, submitted to Swiss-Prot. Data Bank Jul. 2002.

Michalowski et al., Sequence from Nucleic Acid, submitted to the EMBL/GenBank/DDGB Databases Jun. 1998.

ASTM D 964, Standard Specification for Metallic Copper Powder for Use in Antifouling Paints, published May 2003, 1 page.

ASTM D 2574, Standard Test Method for Resistance of Emulsion Paints in the Container to Attack by Microorganisms, published Sep. 1997, 4 pages.

ASTM D 3273, Standard Test Method for Resistance to Growth of Mold on the Surface of Interior Coatings in an Environmental Chamber, published Oct. 1994, 3 pages.

ASTM D 3274, Standard Test Method for Evaluating Degree of Surface Disfigurement of Paint Films by Microbial (Fungal or Algal) Growth or Soil and Dirt Accumulation, published Jun. 1995, 4 pages.

ASTM D 3456, Standard Practice for Determining by Exterior Exposure Tests the Susceptibility of Paint Films to Microbiological Attack, published May 1986, 4 pages.

ASTM D 3623, Standard Test Method for Testing Antifouling Panels in Shallow Submergence, published Jun. 2004, 8 pages.

ASTM D 4610, Standard Guide for Determining the Presence of and Removing Microbial (Fungal or Algal) Growth on Paint and Related Coatings, published Jun. 2004, 2 pages.

ASTM D 4938, Standard Test Method for Erosion Testing of Antifouling Paints Using High Velocity Water, published Jun. 1989, 4 pages.

ASTM D 4939, Standard Test Method for Subjecting Marine Antifouling Coating to Biofouling and Fluid Shear Forces in Natural Seawater, published May 2003, 5 pages.

(56) References Cited

OTHER PUBLICATIONS

ASTM D 5108, Standard Test Method for Organotin Release Rates of Antifouling Coating Systems in Sea Water, published Feb. 1991, 6 pages.
ASTM D 5479, Standard Practice for Testing Biofouling Resistance of Marine Coatings Partially Immersed, published May 1994, 2 pages.
ASTM D 5589, Standard Practice Test Method for Determining the Resistance of Paint Films and Related Coatings to Algal Defacement, published Sep. 1997, 4 pages.
ASTM D 5590, Standard Test Method for Determining the Resistance of Paint Films and Related Coatings to Fungal Defacement by Accelerated Four-Week Agar Plate Assay, published Oct. 1994, 4 pages.
ASTM D 5618, Standard Test Method for Measurement of Barnacle Adhesion Strength in Shear, published Dec. 1994, 2 pages.
ASTM D 912, Standard Specification for Cuprous Oxide for Use in Antifouling Paints, Dec. 1981, 1 page.
Bell et al., "Reactive Coatings Literature Review," prepared for the U.S. Army Research Office, Dec. 2001, 41 pages.
"Green Marine Paint," Chemical Week, Apr. 2001, p. 33.
Flick, Handbook of Paint Raw Materials, 2nd Ed., published by Noyes Publications, Aug. 1989, pp. 263-285.
Wicks et al., Organic Coatings, Science and Technology, vol. 1: Film Formation, Components, and Appearance, published by Wiley-Interscience, Oct. 1992, pp. 318-320.
Wicks et al., Organic Coatings, Science and Technology, vol. 2: Applications, Properties, and Performance, published by Wiley-Interscience, Nov. 1993, pp. 145, 309, 319-323, 340-341.
"PPG Installs Cleaning System," PCI Magazine, Jul. 2002, pp. 68-70.
"Copper-8-Quinolinolate Chemistry for Specialty Wood Preservative," PCI Magazine, Jun. 2002, 3 pages.
"Emulsion Polymer Technologies," Paint Research Association, vol. 13, No. 12, Apr. 2002, 24 pages.
"The PCI 50 & Global Top 10," PCI Magazine, Jun. 2002, 34 pages.
Winkowski, "Controlling Microbial Contamination," PCI Magazine, Jun. 2002, 6 pages.
Paint and Surface Coatings, Theory and Practice, 2nd Ed., © 1999 Woodhead Publishing Ltd., pp. 2, 3, 10, 24, 51, 162, 193, 194, 371-383, 397, 448, 494-497, 533, 541-547, 700.
Drevon et al., "High-Activity Enzyme-Polyurethane Coatings," Biotechnology & Bioengineering, vol. 79, No. 7, 2002, pp. 785-794.
Handbook of Coatings Additives, © 1987 Marcel Dekker, Inc., pp. 43-63 and 177-224.
Almeida et al., "Solution Structure of *Pisum sativum* Defensin 1 by High Resolution NMR: Plant Defensins, Identical Backbone with Different Mechanisms of Action," J. Mol. Biol., vol. 315, 2002, pp. 749-757.
Bobek et al., "MUC7 20-Mer: Investigation of Antimicrobial Activity, Secondary Structure, and Possible Mechanism of Antifungal Action," Antimicrobial Agents & Chemotherapy, vol. 47, No. 2, Feb. 2003, pp. 643-652.
Cammue et al., "Isolation and Characterization of a Novel Class of Plant Antimicrobial Peptides from *Mirabilis jalapa* L. Seeds," The Journal of Biological Chemistry, vol. 267, No. 4, Feb. 1992, pp. 2228-2233.
Duvick et al., "Purification and Characterization of a Novel Antimicrobial Peptide from Maize (*Zea mays* L.) Kernels," The Journal of Biological Chemistry, vol. 267, No. 26, Sep. 1992, pp. 18814-18820.

Fernandes et al., "Anti-microbial properties of histone H2A from skin secretions of rainbow trout, *Oncorhynchus mykiss*," Biochem. J., vol. 368, 2002, pp. 611-620.
Fujitani et al., "Structure of the Antimicrobial Peptide Tachystatin A," The Journal of Biological Chemistry, vol. 277, No. 26, Jun. 2002, pp. 23651-23657.
Gao et al., "Solution Structure of PAFP-S: A New Knottin-Type Antifungal Peptide from the Seeds of *Phytolacca americana*," Biochemistry, vol. 40, 2001, pp. 10973-10978.
Gesell et al., "Two-dimensional 1H NMR experiments show that the 23-residue magainin antibiotic peptide is an α-helix in dodecylphosphocholine micelles, sodium dodecylsulfate micelles, and trifluoroethanol/water solution," Journal of Biololecular NMR, vol. 9, 1997, pp. 127-135.
Halverson et al., "Purification and characterization of antimicrobial peptides from the skin of the North American green frog *Rana clamitans*," Peptides, vol. 21, 2000, pp. 469-476.
Hara et al., "Effects of Peptide Dimerization on Pore Formation: Antiparallel Disulfide-Dimerized Magainin 2 Analogue," Biopolymers, vol. 58, 2001, pp. 437-446.
Hill et al., "Crystal Structure of Defensin HNP-3, an Amphiphilic Dimer: Mechanisms of Membrane Permeabilization," Science, New Series, vol. 251, No. 5000, Mar. 1991, pp. 1481-1485.
Hunter et al., "The Solution Structure of Human Hepcidin, a Peptide Hormone with Antimicrobial Activity that is Involved in Iron Uptake and Hereditary Hemochromatosis," The Journal of Biological Chemistry, vol. 277, No. 40, Oct. 2002, pp. 37597-37603.
Hwang et al., "Three-Dimensional Solution Structure of Lactoferricin B, an Antimicrobial Peptide Derived from Bovine Lactoferrin," Biochemistry, vol. 37, 1998, pp. 4288-4298.
Jones et al., "Defensin-6 mRNA in human Paneth cells: implications for antimicrobial peptides in host defense of the human bowel," FEBS Lett., vol. 315, No. 2, Jan. 1993, pp. 187-192.
Kokryakov et al., "Protegrins: leukocyte antimicrobial peptides that combine features of corticostatic defensins and tachyplesins," FEBS Lett., vol. 327, No. 2, Jul. 1993, pp. 231-236.
Lamberty et al., "Solution Structures of the Antifungal Heliomicin and a Selected Variant with both Antibacterial and Antifungal Activities," Biochemistry, vol. 40, 2001, pp. 11995-12003.
Lamberty et al., "Insect Immunity, Constitutive Expression of a Cysteine-Rich Antifungal and a Linear Antibacterial Peptide in a Termite Insect," The Journal of Biological Chemistry, vol. 276, No. 6, Feb. 2001, pp. 4085-4092.
Lee et al., "Antibiotic Activity of Reversed Peptides of α-Helical Antimicrobial Peptide, P18," Protein & Peptide Letters, vol. 9, No. 5, 2002, pp. 395-402.
Jamieson, "New Perspectives on Seed Enhancement," Acta Hort., vol. 782, ISHS 2008, pp. 143-150.
Johnson, "Germination," Seed Development, Copyright 2003 by Elsevier Ltd., pp. 1298-1304.
Scott, "Seed Coatings and Treatments and Their Effects on Plant Establishment," Advances in Agronomy, vol. 42, Copyright 1989 by Academic Press, Inc., pp. 43-83.
Taylor et al., "Concepts and Technologies of Selected Seed Treatments," Annu. Rev. Phytopathol., Copyright 1990 by Annual Reviews Inc., pp. 321-339.
Taylor, "Seed Treatments," Seed Development, Copyright 2003 by Elsevier Ltd., pp. 1291-1298.

\* cited by examiner

```
                        SEQUENCE LISTING

<160> NUMBER OF SEQ ID NOS: 199

<210> SEQ ID NO 1
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 1

Xaa Xaa Xaa Xaa Arg Phe
1               5

<210> SEQ ID NO 2
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 2

Xaa Xaa Xaa Xaa Phe His
1               5

<210> SEQ ID NO 3
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 3

Xaa Xaa Xaa Xaa Lys Phe
1               5

<210> SEQ ID NO 4
<211> LENGTH: 6
<212> TYPE: PRT
```

```
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 4

Xaa Xaa Xaa Xaa Gln Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 5

Xaa Xaa Xaa Xaa Arg Met
1               5

<210> SEQ ID NO 6
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 6

Xaa Xaa Xaa Xaa His Met
1               5

<210> SEQ ID NO 7
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 7

Xaa Xaa Xaa Xaa Lys Leu
1               5

<210> SEQ ID NO 8
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 8

Xaa Xaa Xaa Xaa Arg Leu
1               5
```

```
<210> SEQ ID NO 9
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 9

Xaa Xaa Xaa Leu Arg Phe
1               5

<210> SEQ ID NO 10
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 10

Xaa Xaa Xaa Ile Arg Phe
1               5

<210> SEQ ID NO 11
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 11

Xaa Xaa Xaa Phe Arg Phe
1               5

<210> SEQ ID NO 12
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 12

Xaa Xaa Xaa Trp Arg Phe
1               5

<210> SEQ ID NO 13
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid
```

```
<400> SEQUENCE: 13

Xaa Xaa Xaa Met Arg Phe
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 14

Xaa Xaa Lys Leu Arg Phe
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 15

Xaa Xaa Arg Leu Arg Phe
1               5

<210> SEQ ID NO 16
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 16

Xaa Xaa His Leu Arg Phe
1               5

<210> SEQ ID NO 17
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 17

Xaa Xaa Thr Leu Arg Phe
1               5

<210> SEQ ID NO 18
<211> LENGTH: 6
<212> TYPE: PRT
<213> ORGANISM: Artificial Sequence
<220> FEATURE:
```

```
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 18

Xaa Xaa Phe Leu Arg Phe
1               5

<210> SEQ ID NO 19
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 19

Xaa Xaa Ser Leu Arg Phe
1               5

<210> SEQ ID NO 20
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 20

Xaa Xaa Ile Leu Arg Phe
1               5

<210> SEQ ID NO 21
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 21

Xaa Xaa Leu Leu Arg Phe
1               5

<210> SEQ ID NO 22
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 22

Xaa Xaa Ala Leu Arg Phe
1               5
```

```
<210> SEQ ID NO 23
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 23

Xaa Xaa Trp Leu Arg Phe
1               5

<210> SEQ ID NO 24
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 24

Xaa Xaa Met Leu Arg Phe
1               5

<210> SEQ ID NO 25
<211> LENGTH: 3
<212> TYPE: PRT
<213> ORGANISM: Artificial Sequence
<220> FEATURE:
<223> OTHER INFORMATION: Synthesized

<400> SEQUENCE: 25

Phe Arg Phe
1

<210> SEQ ID NO 26
<211> LENGTH: 3
<212> TYPE: PRT
<213> ORGANISM: Artificial Sequence
<220> FEATURE:
<223> OTHER INFORMATION: Synthesized

<400> SEQUENCE: 26

Leu Arg Phe
1

<210> SEQ ID NO 27
<211> LENGTH: 3
<212> TYPE: PRT
<213> ORGANISM: Artificial Sequence
<220> FEATURE:
<223> OTHER INFORMATION: Synthesized

<400> SEQUENCE: 27

Trp Arg Phe
1

<210> SEQ ID NO 28
<211> LENGTH: 3
<212> TYPE: PRT
<213> ORGANISM: Artificial Sequence
<220> FEATURE:
<223> OTHER INFORMATION: Synthesized
```

```
<400> SEQUENCE: 28

His Arg Phe
1

<210> SEQ ID NO 29
<211> LENGTH: 4
<212> TYPE: PRT
<213> ORGANISM: Artificial Sequence
<220> FEATURE:
<223> OTHER INFORMATION: Synthesized

<400> SEQUENCE: 29

Phe Leu Arg Phe
1

<210> SEQ ID NO 30
<211> LENGTH: 4
<212> TYPE: PRT
<213> ORGANISM: Artificial Sequence
<220> FEATURE:
<223> OTHER INFORMATION: Synthesized

<400> SEQUENCE: 30

Trp Leu Arg Phe
1

<210> SEQ ID NO 31
<211> LENGTH: 5
<212> TYPE: PRT
<213> ORGANISM: Artificial Sequence
<220> FEATURE:
<223> OTHER INFORMATION: Synthesized

<400> SEQUENCE: 31

Phe His Leu Arg Phe
1               5

<210> SEQ ID NO 32
<211> LENGTH: 6
<212> TYPE: PRT
<213> ORGANISM: Artificial Sequence
<220> FEATURE:
<223> OTHER INFORMATION: Synthesized

<400> SEQUENCE: 32

Phe Phe Lys Leu Arg Phe
1               5

<210> SEQ ID NO 33
<211> LENGTH: 6
<212> TYPE: PRT
<213> ORGANISM: Artificial Sequence
<220> FEATURE:
<223> OTHER INFORMATION: Synthesized

<400> SEQUENCE: 33

Val Phe Lys Leu Arg Phe
1               5

<210> SEQ ID NO 34
<211> LENGTH: 6
<212> TYPE: PRT
<213> ORGANISM: Artificial Sequence
<220> FEATURE:
<223> OTHER INFORMATION: Synthesized

<400> SEQUENCE: 34
```

```
His Phe Lys Leu Arg Phe
1               5

<210> SEQ ID NO 35
<211> LENGTH: 6
<212> TYPE: PRT
<213> ORGANISM: Artificial Sequence
<220> FEATURE:
<223> OTHER INFORMATION: Synthesized

<400> SEQUENCE: 35

Ile Phe Lys Leu Arg Phe
1               5

<210> SEQ ID NO 36
<211> LENGTH: 6
<212> TYPE: PRT
<213> ORGANISM: Artificial Sequence
<220> FEATURE:
<223> OTHER INFORMATION: Synthesized

<400> SEQUENCE: 36

Lys Arg Lys Leu Arg Phe
1               5

<210> SEQ ID NO 37
<211> LENGTH: 6
<212> TYPE: PRT
<213> ORGANISM: Artificial Sequence
<220> FEATURE:
<223> OTHER INFORMATION: Synthesized

<400> SEQUENCE: 37

Leu Phe Lys Leu Arg Phe
1               5

<210> SEQ ID NO 38
<211> LENGTH: 6
<212> TYPE: PRT
<213> ORGANISM: Artificial Sequence
<220> FEATURE:
<223> OTHER INFORMATION: Synthesized

<400> SEQUENCE: 38

Tyr Phe Lys Leu Arg Phe
1               5

<210> SEQ ID NO 39
<211> LENGTH: 7
<212> TYPE: PRT
<213> ORGANISM: Artificial Sequence
<220> FEATURE:
<223> OTHER INFORMATION: Synthesized

<400> SEQUENCE: 39

Phe His Phe Lys Leu Arg Phe
1               5

<210> SEQ ID NO 40
<211> LENGTH: 7
<212> TYPE: PRT
<213> ORGANISM: Artificial Sequence
<220> FEATURE:
<223> OTHER INFORMATION: Synthesized

<400> SEQUENCE: 40

Ile His Phe Lys Leu Arg Phe
1               5
```

```
<210> SEQ ID NO 41
<211> LENGTH: 6
<212> TYPE: PRT
<213> ORGANISM: Artificial Sequence
<220> FEATURE:
<223> OTHER INFORMATION: Synthesized

<400> SEQUENCE: 41

Phe Arg Leu Lys Phe His
1               5

<210> SEQ ID NO 42
<211> LENGTH: 6
<212> TYPE: PRT
<213> ORGANISM: Artificial Sequence
<220> FEATURE:
<223> OTHER INFORMATION: Synthesized

<400> SEQUENCE: 42

Arg Phe Lys Leu Arg Phe
1               5

<210> SEQ ID NO 43
<211> LENGTH: 6
<212> TYPE: PRT
<213> ORGANISM: Artificial Sequence
<220> FEATURE:
<223> OTHER INFORMATION: Synthesized

<400> SEQUENCE: 43

Ser Phe Lys Leu Arg Phe
1               5

<210> SEQ ID NO 44
<211> LENGTH: 6
<212> TYPE: PRT
<213> ORGANISM: Artificial Sequence
<220> FEATURE:
<223> OTHER INFORMATION: Synthesized

<400> SEQUENCE: 44

Met Phe Lys Leu Arg Phe
1               5

<210> SEQ ID NO 45
<211> LENGTH: 6
<212> TYPE: PRT
<213> ORGANISM: Artificial Sequence
<220> FEATURE:
<223> OTHER INFORMATION: Synthesized

<400> SEQUENCE: 45

Thr Phe Lys Leu Arg Phe
1               5

<210> SEQ ID NO 46
<211> LENGTH: 6
<212> TYPE: PRT
<213> ORGANISM: Artificial Sequence
<220> FEATURE:
<223> OTHER INFORMATION: Synthesized

<400> SEQUENCE: 46

Gln Phe Lys Leu Arg Phe
1               5
```

```
<210> SEQ ID NO 47
<211> LENGTH: 6
<212> TYPE: PRT
<213> ORGANISM: Artificial Sequence
<220> FEATURE:
<223> OTHER INFORMATION: Synthesized

<400> SEQUENCE: 47

Trp Phe Lys Leu Arg Phe
1               5

<210> SEQ ID NO 48
<211> LENGTH: 44
<212> TYPE: PRT
<213> ORGANISM: Tachypleus tridentatus
<220> FEATURE:
<221> NAME/KEY: misc_feature
<223> OTHER INFORMATION: Tachystatin A Peptide

<400> SEQUENCE: 48

Tyr Ser Arg Cys Gln Leu Gln Gly Phe Asn Cys Val Val Arg Ser Tyr
1               5                   10                  15

Gly Leu Pro Thr Ile Pro Cys Cys Arg Gly Leu Thr Cys Arg Ser Tyr
            20                  25                  30

Phe Pro Gly Ser Thr Tyr Gly Arg Cys Gln Arg Tyr
        35                  40

<210> SEQ ID NO 49
<211> LENGTH: 25
<212> TYPE: PRT
<213> ORGANISM: Androctonus australis

<400> SEQUENCE: 49

Arg Ser Val Cys Arg Gln Ile Lys Ile Cys Arg Arg Gly Gly Cys
1               5                   10                  15

Tyr Tyr Lys Cys Thr Asn Arg Pro Tyr
            20                  25

<210> SEQ ID NO 50
<211> LENGTH: 13
<212> TYPE: PRT
<213> ORGANISM: Unknown
<220> FEATURE:
<223> OTHER INFORMATION: Synthetic Tritrpticin

<400> SEQUENCE: 50

Val Arg Arg Phe Pro Trp Trp Trp Pro Phe Leu Arg Arg
1               5                   10

<210> SEQ ID NO 51
<211> LENGTH: 30
<212> TYPE: PRT
<213> ORGANISM: Homo sapiens
<220> FEATURE:
<221> NAME/KEY: misc_feature
<223> OTHER INFORMATION: HNP-3 Defensin

<400> SEQUENCE: 51

Asp Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 52
<211> LENGTH: 38
<212> TYPE: PRT
```

-continued

<213> ORGANISM: Phytolacca americana

<400> SEQUENCE: 52

Ala Gly Cys Ile Lys Asn Gly Gly Arg Cys Asn Ala Ser Ala Gly Pro
1               5                   10                  15

Pro Tyr Cys Cys Ser Ser Tyr Cys Phe Gln Ile Ala Gly Gln Ser Tyr
            20                  25                  30

Gly Val Cys Lys Asn Arg
        35

<210> SEQ ID NO 53
<211> LENGTH: 23
<212> TYPE: PRT
<213> ORGANISM: Unknown
<220> FEATURE:
<223> OTHER INFORMATION: Synthetic construct Magainin 2

<400> SEQUENCE: 53

Gly Ile Gly Lys Tyr Leu His Ser Ala Lys Phe Gly Lys Ala Trp
1               5                   10                  15

Val Gly Glu Ile Met Asn Ser
            20

<210> SEQ ID NO 54
<211> LENGTH: 13
<212> TYPE: PRT
<213> ORGANISM: Bos taurus

<400> SEQUENCE: 54

Ile Leu Pro Trp Lys Trp Pro Trp Trp Pro Trp Arg Arg
1               5                   10

<210> SEQ ID NO 55
<211> LENGTH: 44
<212> TYPE: PRT
<213> ORGANISM: Heliothis virescens

<400> SEQUENCE: 55

Asp Lys Leu Ile Gly Ser Cys Val Trp Gly Ala Val Asn Tyr Thr Ser
1               5                   10                  15

Asp Cys Asn Gly Glu Cys Lys Arg Arg Gly Tyr Lys Gly Gly His Cys
            20                  25                  30

Gly Ser Phe Ala Asn Val Asn Cys Trp Cys Glu Thr
        35                  40

<210> SEQ ID NO 56
<211> LENGTH: 44
<212> TYPE: PRT
<213> ORGANISM: Heliothis virescens

<400> SEQUENCE: 56

Asp Lys Leu Ile Gly Ser Cys Val Trp Gly Ala Val Asn Tyr Thr Ser
1               5                   10                  15

Asp Cys Asn Gly Glu Cys Lys Arg Arg Gly Tyr Lys Gly Gly His Cys
            20                  25                  30

Gly Ser Phe Ala Asn Val Asn Cys Trp Cys Glu Thr
        35                  40

<210> SEQ ID NO 57
<211> LENGTH: 46
<212> TYPE: PRT
<213> ORGANISM: Pisum sativum
<220> FEATURE:

```
<221> NAME/KEY: misc_feature
<223> OTHER INFORMATION: Seed of pea defensin 1 (psd1)

<400> SEQUENCE: 57

Lys Thr Cys Glu His Leu Ala Asp Thr Tyr Arg Gly Val Cys Phe Thr
1               5                   10                  15

Asn Ala Ser Cys Asp Asp His Cys Lys Asn Lys Ala His Leu Ile Ser
            20                  25                  30

Gly Thr Cys His Asn Trp Lys Cys Phe Cys Thr Gln Asn Cys
        35                  40                  45

<210> SEQ ID NO 58
<211> LENGTH: 18
<212> TYPE: PRT
<213> ORGANISM: Unknown
<220> FEATURE:
<223> OTHER INFORMATION: Synthetic Gomesin

<400> SEQUENCE: 58

Gln Cys Arg Arg Leu Cys Tyr Lys Gln Arg Cys Val Thr Tyr Cys Arg
1               5                   10                  15

Gly Arg

<210> SEQ ID NO 59
<211> LENGTH: 25
<212> TYPE: PRT
<213> ORGANISM: Bos taurus
<220> FEATURE:
<221> NAME/KEY: misc_feature
<223> OTHER INFORMATION: Lactoferricin B

<400> SEQUENCE: 59

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 60
<211> LENGTH: 12
<212> TYPE: PRT
<213> ORGANISM: Unknown
<220> FEATURE:
<223> OTHER INFORMATION: Synthetic PW2

<400> SEQUENCE: 60

His Pro Leu Lys Gln Tyr Trp Trp Arg Pro Ser Ile
1               5                   10

<210> SEQ ID NO 61
<211> LENGTH: 20
<212> TYPE: PRT
<213> ORGANISM: Homo sapiens
<220> FEATURE:
<221> NAME/KEY: misc_feature
<223> OTHER INFORMATION: Hepcidin 20

<400> SEQUENCE: 61

Ile Cys Ile Phe Cys Cys Gly Cys Cys His Arg Ser Lys Cys Gly Met
1               5                   10                  15

Cys Cys Lys Thr
            20

<210> SEQ ID NO 62
<211> LENGTH: 25
<212> TYPE: PRT
```

```
<213> ORGANISM: Homo sapiens
<220> FEATURE:
<221> NAME/KEY: misc_feature
<223> OTHER INFORMATION: Hepcidin 25

<400> SEQUENCE: 62

Asp Thr His Phe Pro Ile Cys Ile Phe Cys Cys Gly Cys Cys His Arg
1               5                   10                  15

Ser Lys Cys Gly Met Cys Cys Lys Thr
            20                  25

<210> SEQ ID NO 63
<211> LENGTH: 30
<212> TYPE: PRT
<213> ORGANISM: Amaranthus caudatus

<400> SEQUENCE: 63

Val Gly Glu Cys Val Arg Gly Arg Cys Pro Ser Gly Met Cys Cys Ser
1               5                   10                  15

Gln Phe Gly Tyr Cys Gly Lys Gly Pro Lys Tyr Cys Gly Arg
            20                  25                  30

<210> SEQ ID NO 64
<211> LENGTH: 78
<212> TYPE: PRT
<213> ORGANISM: Amaranthus caudatus

<400> SEQUENCE: 64

Gly Tyr Phe Cys Glu Ser Cys Arg Lys Ile Ile Gln Lys Leu Glu Asp
1               5                   10                  15

Met Val Gly Pro Gln Pro Asn Glu Asp Thr Val Thr Gln Ala Ala Ser
            20                  25                  30

Gln Val Cys Asp Lys Leu Lys Ile Leu Arg Gly Leu Cys Lys Lys Ile
        35                  40                  45

Met Arg Ser Phe Leu Arg Arg Ile Ser Trp Asp Ile Leu Thr Gly Lys
    50                  55                  60

Lys Pro Gln Ala Ile Cys Val Asp Ile Lys Ile Cys Lys Glu
65                  70                  75

<210> SEQ ID NO 65
<211> LENGTH: 23
<212> TYPE: PRT
<213> ORGANISM: Xenopus laevis
<220> FEATURE:
<221> NAME/KEY: misc_feature
<223> OTHER INFORMATION: Magainin 2

<400> SEQUENCE: 65

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 66
<211> LENGTH: 26
<212> TYPE: PRT
<213> ORGANISM: Apis mellifera
<220> FEATURE:
<221> NAME/KEY: misc_feature
<223> OTHER INFORMATION: venom Melittin B

<400> SEQUENCE: 66

Gly Ile Gly Ala Val Leu Lys Val Leu Thr Thr Gly Leu Pro Ala Leu
1               5                   10                  15
```

Ile Ser Trp Ile Lys Arg Lys Arg Gln Gln
            20                  25

<210> SEQ ID NO 67
<211> LENGTH: 21
<212> TYPE: PRT
<213> ORGANISM: Podisus maculiventris

<400> SEQUENCE: 67

Gly Ser Lys Lys Pro Val Pro Ile Ile Tyr Cys Asn Arg Arg Thr Gly
1               5                   10                  15

Lys Cys Gln Arg Met
            20

<210> SEQ ID NO 68
<211> LENGTH: 38
<212> TYPE: PRT
<213> ORGANISM: Mesembryanthemum crystallinum
<220> FEATURE:
<221> NAME/KEY: misc_feature
<223> OTHER INFORMATION: Antimicrobial peptide 1

<400> SEQUENCE: 68

Ala Lys Cys Ile Lys Asn Gly Lys Gly Cys Arg Glu Asp Gln Gly Pro
1               5                   10                  15

Pro Phe Cys Cys Ser Gly Phe Cys Tyr Arg Gln Val Gly Trp Ala Arg
            20                  25                  30

Gly Tyr Cys Lys Asn Arg
        35

<210> SEQ ID NO 69
<211> LENGTH: 13
<212> TYPE: PRT
<213> ORGANISM: Bos taurus
<220> FEATURE:
<221> NAME/KEY: misc_feature
<223> OTHER INFORMATION: Melanotropin alpha (Alpha-MSH)

<400> SEQUENCE: 69

Ser Tyr Ser Met Glu His Phe Arg Trp Gly Lys Pro Val
1               5                   10

<210> SEQ ID NO 70
<211> LENGTH: 33
<212> TYPE: PRT
<213> ORGANISM: Oryctolagus cuniculus
<220> FEATURE:
<221> NAME/KEY: misc_feature
<223> OTHER INFORMATION: Corticostatin III (MCP-1)

<400> SEQUENCE: 70

Val Val Cys Ala Cys Arg Arg Ala Leu Cys Leu Pro Arg Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 71
<211> LENGTH: 33
<212> TYPE: PRT
<213> ORGANISM: Oryctolagus cuniculus
<220> FEATURE:
<221> NAME/KEY: misc_feature
<223> OTHER INFORMATION: Corticostatin IV (MCP-2)

-continued

```
<400> SEQUENCE: 71

Val Val Cys Ala Cys Arg Arg Ala Leu Cys Leu Pro Leu Glu Arg Arg
1               5                   10                  15

Ala Gly Phe Cys Arg Ile Arg Gly Arg Ile His Pro Leu Cys Cys Arg
            20                  25                  30

Arg

<210> SEQ ID NO 72
<211> LENGTH: 35
<212> TYPE: PRT
<213> ORGANISM: Antheraea pernyi
<220> FEATURE:
<221> NAME/KEY: misc_feature
<223> OTHER INFORMATION: Cecropin B

<400> SEQUENCE: 72

Lys Trp Lys Ile Phe Lys Lys Ile Glu Lys Val Gly Arg Asn Ile Arg
1               5                   10                  15

Asn Gly Ile Ile Lys Ala Gly Pro Ala Val Ala Val Leu Gly Glu Ala
            20                  25                  30

Lys Ala Leu
        35

<210> SEQ ID NO 73
<211> LENGTH: 48
<212> TYPE: PRT
<213> ORGANISM: Bos taurus
<220> FEATURE:
<221> NAME/KEY: misc_feature
<223> OTHER INFORMATION: Seminalplasmin

<400> SEQUENCE: 73

Ser Asp Glu Lys Ala Ser Pro Asp Lys His His Arg Phe Ser Leu Ser
1               5                   10                  15

Arg Tyr Ala Lys Leu Ala Asn Arg Leu Ala Asn Pro Lys Leu Leu Glu
            20                  25                  30

Thr Phe Leu Ser Lys Trp Ile Gly Asp Arg Gly Asn Arg Ser Val Lys
        35                  40                  45

<210> SEQ ID NO 74
<211> LENGTH: 34
<212> TYPE: PRT
<213> ORGANISM: Oryctolagus cuniculus
<220> FEATURE:
<221> NAME/KEY: misc_feature
<223> OTHER INFORMATION: NP-3A defensin

<400> SEQUENCE: 74

Gly Ile Cys Ala Cys Arg Arg Arg Phe Cys Pro Asn Ser Glu Arg Phe
1               5                   10                  15

Ser Gly Tyr Cys Arg Val Asn Gly Ala Arg Tyr Val Arg Cys Cys Ser
            20                  25                  30

Arg Arg

<210> SEQ ID NO 75
<211> LENGTH: 30
<212> TYPE: PRT
<213> ORGANISM: Homo sapiens
<220> FEATURE:
<221> NAME/KEY: misc_feature
<223> OTHER INFORMATION: HNP-1 Defensin

<400> SEQUENCE: 75
```

```
Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30
```

<210> SEQ ID NO 76
<211> LENGTH: 29
<212> TYPE: PRT
<213> ORGANISM: Homo sapiens
<220> FEATURE:
<221> NAME/KEY: misc_feature
<223> OTHER INFORMATION: HNP-2 Defensin

<400> SEQUENCE: 76

```
Cys Tyr Cys Arg Ile Pro Ala Cys Ile Ala Gly Glu Arg Arg Tyr Gly
1               5                   10                  15

Thr Cys Ile Tyr Gln Gly Arg Leu Trp Ala Phe Cys Cys
            20                  25
```

<210> SEQ ID NO 77
<211> LENGTH: 33
<212> TYPE: PRT
<213> ORGANISM: Homo sapiens
<220> FEATURE:
<221> NAME/KEY: misc_feature
<223> OTHER INFORMATION: HNP-4 Defensin

<400> SEQUENCE: 77

```
Val Cys Ser Cys Arg Leu Val Phe Cys Arg Arg Thr Glu Leu Arg Val
1               5                   10                  15

Gly Asn Cys Leu Ile Gly Gly Val Ser Phe Thr Tyr Cys Cys Thr Arg
            20                  25                  30

Val
```

<210> SEQ ID NO 78
<211> LENGTH: 24
<212> TYPE: PRT
<213> ORGANISM: Homo sapiens
<220> FEATURE:
<221> NAME/KEY: misc_feature
<223> OTHER INFORMATION: Histatin 5

<400> SEQUENCE: 78

```
Asp Ser His Ala Lys Arg His His Gly Tyr Lys Arg Lys Phe His Glu
1               5                   10                  15

Lys His His Ser His Arg Gly Tyr
            20
```

<210> SEQ ID NO 79
<211> LENGTH: 32
<212> TYPE: PRT
<213> ORGANISM: Homo sapiens
<220> FEATURE:
<221> NAME/KEY: misc_feature
<223> OTHER INFORMATION: Histatin 3

<400> SEQUENCE: 79

```
Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30
```

<210> SEQ ID NO 80
<211> LENGTH: 12
<212> TYPE: PRT

```
<213> ORGANISM: Unknown
<220> FEATURE:
<223> OTHER INFORMATION: Histatin 8

<400> SEQUENCE: 80

Lys Phe His Glu Lys His His Ser His Arg Gly Tyr
1               5                   10

<210> SEQ ID NO 81
<211> LENGTH: 38
<212> TYPE: PRT
<213> ORGANISM: Bos taurus
<220> FEATURE:
<221> NAME/KEY: misc_feature
<223> OTHER INFORMATION: Tracheal antimicrobial peptide

<400> SEQUENCE: 81

Asn Pro Val Ser Cys Val Arg Asn Lys Gly Ile Cys Val Pro Ile Arg
1               5                   10                  15

Cys Pro Gly Ser Met Lys Gln Ile Gly Thr Cys Val Gly Arg Ala Val
                20                  25                  30

Lys Cys Cys Arg Lys Lys
            35

<210> SEQ ID NO 82
<211> LENGTH: 37
<212> TYPE: PRT
<213> ORGANISM: Mirabilis jalapa
<220> FEATURE:
<221> NAME/KEY: misc_feature
<223> OTHER INFORMATION: antimicrobial peptidic agent1 (MJ-antimicrobial
      peptidic agent1)

<400> SEQUENCE: 82

Gln Cys Ile Gly Asn Gly Gly Arg Cys Asn Glu Asn Val Gly Pro Pro
1               5                   10                  15

Tyr Cys Cys Ser Gly Phe Cys Leu Arg Gln Pro Gly Gln Gly Tyr Gly
                20                  25                  30

Tyr Cys Lys Asn Arg
            35

<210> SEQ ID NO 83
<211> LENGTH: 36
<212> TYPE: PRT
<213> ORGANISM: Mirabilis jalapa
<220> FEATURE:
<221> NAME/KEY: misc_feature
<223> OTHER INFORMATION: antimicrobial peptidic agent2 (MJ-antimicrobial
      peptidic agent2)

<400> SEQUENCE: 83

Cys Ile Gly Asn Gly Gly Arg Cys Asn Glu Asn Val Gly Pro Pro Tyr
1               5                   10                  15

Cys Cys Ser Gly Phe Cys Leu Arg Gln Pro Asn Gln Gly Tyr Gly Val
                20                  25                  30

Cys Arg Asn Arg
            35

<210> SEQ ID NO 84
<211> LENGTH: 33
<212> TYPE: PRT
<213> ORGANISM: Zea mays
<220> FEATURE:
<221> NAME/KEY: misc_feature
<223> OTHER INFORMATION: MBP-1
```

<400> SEQUENCE: 84

Arg Ser Gly Arg Gly Glu Cys Arg Arg Gln Cys Leu Arg Arg His Glu
1               5                   10                  15

Gly Gln Pro Trp Glu Thr Gln Glu Cys Met Arg Arg Cys Arg Arg Arg
            20                  25                  30

Gly

<210> SEQ ID NO 85
<211> LENGTH: 23
<212> TYPE: PRT
<213> ORGANISM: Brassica napus
<220> FEATURE:
<221> NAME/KEY: misc_feature
<223> OTHER INFORMATION: AFP2

<400> SEQUENCE: 85

Gln Lys Leu Cys Glu Arg Pro Ser Gly Thr Trp Ser Gly Val Cys Gly
1               5                   10                  15

Asn Asn Asn Ala Cys Lys Asn
            20

<210> SEQ ID NO 86
<211> LENGTH: 27
<212> TYPE: PRT
<213> ORGANISM: Brassica rapa
<220> FEATURE:
<221> NAME/KEY: misc_feature
<223> OTHER INFORMATION: AFP1

<400> SEQUENCE: 86

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Asn
            20                  25

<210> SEQ ID NO 87
<211> LENGTH: 27
<212> TYPE: PRT
<213> ORGANISM: Brassica rapa
<220> FEATURE:
<221> NAME/KEY: misc_feature
<223> OTHER INFORMATION: AFP2

<400> SEQUENCE: 87

Gln Lys Leu Cys Glu Arg Pro Ser Gly Thr Trp Ser Gly Val Cys Gly
1               5                   10                  15

Asn Asn Asn Ala Cys Lys Asn Gln Cys Ile Arg
            20                  25

<210> SEQ ID NO 88
<211> LENGTH: 33
<212> TYPE: PRT
<213> ORGANISM: Phyllomedusa bicolor
<220> FEATURE:
<221> NAME/KEY: misc_feature
<223> OTHER INFORMATION: Adenoregulin

<400> SEQUENCE: 88

Gly Leu Trp Ser Lys Ile Lys Glu Val Gly Lys Glu Ala Ala Lys Ala
1               5                   10                  15

Ala Ala Lys Ala Ala Gly Lys Ala Ala Leu Gly Ala Val Ser Glu Ala
            20                  25                  30

Val

<210> SEQ ID NO 89
<211> LENGTH: 16
<212> TYPE: PRT
<213> ORGANISM: Sus scrofa
<220> FEATURE:
<221> NAME/KEY: misc_feature
<223> OTHER INFORMATION: Protegrin 2

<400> SEQUENCE: 89

Arg Gly Gly Arg Leu Cys Tyr Cys Arg Arg Arg Phe Cys Ile Cys Val
1               5                   10                  15

<210> SEQ ID NO 90
<211> LENGTH: 18
<212> TYPE: PRT
<213> ORGANISM: Sus scrofa
<220> FEATURE:
<221> NAME/KEY: misc_feature
<223> OTHER INFORMATION: Protegrin 3

<400> SEQUENCE: 90

Arg Gly Gly Gly Leu Cys Tyr Cys Arg Arg Arg Phe Cys Val Cys Val
1               5                   10                  15

Gly Arg

<210> SEQ ID NO 91
<211> LENGTH: 38
<212> TYPE: PRT
<213> ORGANISM: Macaca fascicularis
<220> FEATURE:
<221> NAME/KEY: misc_feature
<223> OTHER INFORMATION: Histatin 1

<400> SEQUENCE: 91

Asp Ser His Glu Glu Arg His His Gly Arg His Gly His His Lys Tyr
1               5                   10                  15

Gly Arg Lys Phe His Glu Lys His His Ser His Arg Gly Tyr Arg Ser
                20                  25                  30

Asn Tyr Leu Tyr Asp Asn
        35

<210> SEQ ID NO 92
<211> LENGTH: 24
<212> TYPE: PRT
<213> ORGANISM: Xenopus laevis
<220> FEATURE:
<221> NAME/KEY: misc_feature
<223> OTHER INFORMATION: Peptide PGQ

<400> SEQUENCE: 92

Gly Val Leu Ser Asn Val Ile Gly Tyr Leu Lys Lys Leu Gly Thr Gly
1               5                   10                  15

Ala Leu Asn Ala Val Leu Lys Gln
            20

<210> SEQ ID NO 93
<211> LENGTH: 20
<212> TYPE: PRT
<213> ORGANISM: Rana catesbeiana
<220> FEATURE:
<221> NAME/KEY: misc_feature
<223> OTHER INFORMATION: Ranalexin

<400> SEQUENCE: 93

Phe Leu Gly Gly Leu Ile Lys Ile Val Pro Ala Met Ile Cys Ala Val
1               5                   10                  15

Thr Lys Lys Cys
        20

<210> SEQ ID NO 94
<211> LENGTH: 30
<212> TYPE: PRT
<213> ORGANISM: Cavia cutleri
<220> FEATURE:
<221> NAME/KEY: misc_feature
<223> OTHER INFORMATION: GNCP-2

<400> SEQUENCE: 94

Arg Cys Ile Cys Thr Thr Arg Thr Cys Arg Phe Pro Tyr Arg Arg Leu
1               5                   10                  15

Gly Thr Cys Leu Phe Gln Asn Arg Val Tyr Thr Phe Cys Cys
        20                  25                  30

<210> SEQ ID NO 95
<211> LENGTH: 18
<212> TYPE: PRT
<213> ORGANISM: Sus scrofa
<220> FEATURE:
<221> NAME/KEY: misc_feature
<223> OTHER INFORMATION: Protegrin 4

<400> SEQUENCE: 95

Arg Gly Gly Arg Leu Cys Tyr Cys Arg Gly Trp Ile Cys Phe Cys Val
1               5                   10                  15

Gly Arg

<210> SEQ ID NO 96
<211> LENGTH: 18
<212> TYPE: PRT
<213> ORGANISM: Sus scrofa
<220> FEATURE:
<221> NAME/KEY: misc_feature
<223> OTHER INFORMATION: Protegrin 5

<400> SEQUENCE: 96

Arg Gly Gly Arg Leu Cys Tyr Cys Arg Pro Arg Phe Cys Val Cys Val
1               5                   10                  15

Gly Arg

<210> SEQ ID NO 97
<211> LENGTH: 27
<212> TYPE: PRT
<213> ORGANISM: Bos taurus
<220> FEATURE:
<221> NAME/KEY: misc_feature
<223> OTHER INFORMATION: BMAP-27

<400> SEQUENCE: 97

Gly Arg Phe Lys Arg Phe Arg Lys Lys Phe Lys Lys Leu Phe Lys Lys
1               5                   10                  15

Leu Ser Pro Val Ile Pro Leu Leu His Leu Gly
        20                  25

<210> SEQ ID NO 98
<211> LENGTH: 28
<212> TYPE: PRT
<213> ORGANISM: Bos taurus
<220> FEATURE:
<221> NAME/KEY: misc_feature
<223> OTHER INFORMATION: BMAP-28

<400> SEQUENCE: 98

```
Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile Gly
            20                  25
```

```
<210> SEQ ID NO 99
<211> LENGTH: 39
<212> TYPE: PRT
<213> ORGANISM: Bufo bufo gargarizans
<220> FEATURE:
<221> NAME/KEY: misc_feature
<223> OTHER INFORMATION: Buforin 1

<400> SEQUENCE: 99
```

```
Ala Gly Arg Gly Lys Gln Gly Gly Lys Val Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Asn Tyr
        35
```

```
<210> SEQ ID NO 100
<211> LENGTH: 21
<212> TYPE: PRT
<213> ORGANISM: Bufo bufo gargarizans
<220> FEATURE:
<221> NAME/KEY: misc_feature
<223> OTHER INFORMATION: Buforin II

<400> SEQUENCE: 100
```

```
Thr Arg Ser Ser Arg Ala Gly Leu Gln Phe Pro Val Gly Arg Val His
1               5                   10                  15

Arg Leu Leu Arg Lys
            20
```

```
<210> SEQ ID NO 101
<211> LENGTH: 34
<212> TYPE: PRT
<213> ORGANISM: Bos taurus
<220> FEATURE:
<221> NAME/KEY: misc_feature
<223> OTHER INFORMATION: BMAP-34

<400> SEQUENCE: 101
```

```
Gly Leu Phe Arg Arg Leu Arg Asp Ser Ile Arg Arg Gly Gln Gln Lys
1               5                   10                  15

Ile Leu Glu Lys Ala Arg Arg Ile Gly Glu Arg Ile Lys Asp Ile Phe
            20                  25                  30

Arg Gly
```

```
<210> SEQ ID NO 102
<211> LENGTH: 19
<212> TYPE: PRT
<213> ORGANISM: Trichoderma longibrachiatum
<220> FEATURE:
<221> NAME/KEY: misc_feature
<223> OTHER INFORMATION: Tricholongin

<400> SEQUENCE: 102
```

```
Ala Gly Phe Ala Ala Gln Ala Ala Ala Ser Leu Ala Pro Val Ala Ala
1               5                   10                  15

Gln Gln Leu
```

```
<210> SEQ ID NO 103
<211> LENGTH: 34
<212> TYPE: PRT
<213> ORGANISM: Phyllomedusa sauvagei
<220> FEATURE:
<221> NAME/KEY: misc_feature
<223> OTHER INFORMATION: Dermaseptin 1

<400> SEQUENCE: 103

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 104
<211> LENGTH: 45
<212> TYPE: PRT
<213> ORGANISM: Hevea brasiliensis
<220> FEATURE:
<221> NAME/KEY: misc_feature
<223> OTHER INFORMATION: Pseudo-hevein (Minor hevein)

<400> SEQUENCE: 104

Glu Gln Cys Gly Arg Gln Ala Gly Gly Lys Leu Cys Pro Asn Asn Leu
1               5                   10                  15

Cys Cys Ser Gln Tyr Gly Trp Cys Gly Ser Ser Asp Asp Tyr Cys Ser
            20                  25                  30

Pro Ser Lys Asn Cys Gln Ser Asn Cys Lys Gly Gly Gly
            35                  40                  45

<210> SEQ ID NO 105
<211> LENGTH: 33
<212> TYPE: PRT
<213> ORGANISM: Rana rugosa
<220> FEATURE:
<221> NAME/KEY: misc_feature
<223> OTHER INFORMATION: Gaegurin-1

<400> SEQUENCE: 105

Ser Leu Phe Ser Leu Ile Lys Ala Gly Ala Lys Phe Leu Gly Lys Asn
1               5                   10                  15

Leu Leu Lys Gln Gly Ala Cys Tyr Ala Ala Cys Lys Ala Ser Lys Gln
            20                  25                  30

Cys

<210> SEQ ID NO 106
<211> LENGTH: 36
<212> TYPE: PRT
<213> ORGANISM: Phyllomedusa bicolor
<220> FEATURE:
<221> NAME/KEY: misc_feature
<223> OTHER INFORMATION: Skin peptide tyrosine-tyrosine

<400> SEQUENCE: 106

Tyr Pro Pro Lys Pro Glu Ser Pro Gly Glu Asp Ala Ser Pro Glu Glu
1               5                   10                  15

Met Asn Lys Tyr Leu Thr Ala Leu Arg His Tyr Ile Asn Leu Val Thr
            20                  25                  30

Arg Gln Arg Tyr
            35

<210> SEQ ID NO 107
<211> LENGTH: 50
```

<212> TYPE: PRT
<213> ORGANISM: Penaeus vannamei
<220> FEATURE:
<221> NAME/KEY: misc_feature
<223> OTHER INFORMATION: Penaeidin-1

<400> SEQUENCE: 107

Tyr Arg Gly Gly Tyr Thr Gly Pro Ile Pro Arg Pro Pro Ile Gly
1               5                   10                  15

Arg Pro Pro Leu Arg Leu Val Val Cys Ala Cys Tyr Arg Leu Ser Val
            20                  25                  30

Ser Asp Ala Arg Asn Cys Cys Ile Lys Phe Gly Ser Cys Cys His Leu
        35                  40                  45

Val Lys
    50

<210> SEQ ID NO 108
<211> LENGTH: 33
<212> TYPE: PRT
<213> ORGANISM: Mesocricetus auratus
<220> FEATURE:
<221> NAME/KEY: misc_feature
<223> OTHER INFORMATION: Neutrophil defensin 1 (HANP-1)

<400> SEQUENCE: 108

Val Thr Cys Phe Cys Arg Arg Arg Gly Cys Ala Ser Arg Glu Arg His
1               5                   10                  15

Ile Gly Tyr Cys Arg Phe Gly Asn Thr Ile Tyr Arg Leu Cys Cys Arg
            20                  25                  30

Arg

<210> SEQ ID NO 109
<211> LENGTH: 33
<212> TYPE: PRT
<213> ORGANISM: Mesocricetus auratus
<220> FEATURE:
<221> NAME/KEY: misc_feature
<223> OTHER INFORMATION: Neutrophil defensin 3 (HANP-3)

<400> SEQUENCE: 109

Val Thr Cys Phe Cys Arg Arg Arg Gly Cys Ala Ser Arg Glu Arg Leu
1               5                   10                  15

Ile Gly Tyr Cys Arg Phe Gly Asn Thr Ile Tyr Gly Leu Cys Cys Arg
            20                  25                  30

Arg

<210> SEQ ID NO 110
<211> LENGTH: 21
<212> TYPE: PRT
<213> ORGANISM: Misgurnus anguillicaudatus
<220> FEATURE:
<221> NAME/KEY: misc_feature
<223> OTHER INFORMATION: Misgurin

<400> SEQUENCE: 110

Arg Gln Arg Val Glu Glu Leu Ser Lys Phe Ser Lys Lys Gly Ala Ala
1               5                   10                  15

Ala Arg Arg Arg Lys
            20

<210> SEQ ID NO 111
<211> LENGTH: 41
<212> TYPE: PRT
<213> ORGANISM: Pharbitis nil

```
<220> FEATURE:
<221> NAME/KEY: misc_feature
<223> OTHER INFORMATION: PN-antimicrobial peptidic agent

<400> SEQUENCE: 111
```

Gln Gln Cys Gly Arg Gln Ala Ser Gly Arg Leu Cys Gly Asn Arg Leu
1               5                   10                  15

Cys Cys Ser Gln Trp Gly Tyr Cys Gly Ser Thr Ala Ser Tyr Cys Gly
            20                  25                  30

Ala Gly Cys Gln Ser Gln Cys Arg Ser
        35                  40

```
<210> SEQ ID NO 112
<211> LENGTH: 19
<212> TYPE: PRT
<213> ORGANISM: Oncorhynchus mykiss
<220> FEATURE:
<221> NAME/KEY: misc_feature
<223> OTHER INFORMATION: Histone H2B-1(HLP-1)(Fragment)

<400> SEQUENCE: 112
```

Pro Asp Pro Ala Lys Thr Ala Pro Lys Lys Gly Ser Lys Lys Ala Val
1               5                   10                  15

Thr Lys Ala

```
<210> SEQ ID NO 113
<211> LENGTH: 17
<212> TYPE: PRT
<213> ORGANISM: Oncorhynchus mykiss
<220> FEATURE:
<221> NAME/KEY: misc_feature
<223> OTHER INFORMATION: Histone H2B-3(HLP-3)(Fragment)

<400> SEQUENCE: 113
```

Pro Asp Pro Ala Lys Thr Ala Pro Lys Lys Lys Ser Lys Lys Ala Val
1               5                   10                  15

Thr

```
<210> SEQ ID NO 114
<211> LENGTH: 30
<212> TYPE: PRT
<213> ORGANISM: Macaca mulatta
<220> FEATURE:
<221> NAME/KEY: misc_feature
<223> OTHER INFORMATION: neutrophil defensin 2 (RMAD-2)

<400> SEQUENCE: 114
```

Ala Cys Tyr Cys Arg Ile Pro Ala Cys Leu Ala Gly Glu Arg Arg Tyr
1               5                   10                  15

Gly Thr Cys Phe Tyr Met Gly Arg Val Trp Ala Phe Cys Cys
            20                  25                  30

```
<210> SEQ ID NO 115
<211> LENGTH: 36
<212> TYPE: PRT
<213> ORGANISM: Pseudacanthotermes spiniger
<220> FEATURE:
<221> NAME/KEY: misc_feature
<223> OTHER INFORMATION: Termicin

<400> SEQUENCE: 115
```

Ala Cys Asn Phe Gln Ser Cys Trp Ala Thr Cys Gln Ala Gln His Ser
1               5                   10                  15

Ile Tyr Phe Arg Arg Ala Phe Cys Asp Arg Ser Gln Cys Lys Cys Val
            20                  25                  30

Phe Val Arg Gly
        35

<210> SEQ ID NO 116
<211> LENGTH: 25
<212> TYPE: PRT
<213> ORGANISM: Pseudacanthotermas spiniger
<220> FEATURE:
<221> NAME/KEY: misc_feature
<223> OTHER INFORMATION: Spingerin

<400> SEQUENCE: 116

His Val Asp Lys Lys Val Ala Asp Lys Val Leu Leu Leu Lys Gln Leu
1               5                   10                  15

Arg Ile Met Arg Leu Leu Thr Arg Leu
            20                  25

<210> SEQ ID NO 117
<211> LENGTH: 13
<212> TYPE: PRT
<213> ORGANISM: Litoria raniformis
<220> FEATURE:
<221> NAME/KEY: misc_feature
<223> OTHER INFORMATION: Aurein 1.1

<400> SEQUENCE: 117

Gly Leu Phe Asp Ile Ile Lys Lys Ile Ala Glu Ser Ile
1               5                   10

<210> SEQ ID NO 118
<211> LENGTH: 30
<212> TYPE: PRT
<213> ORGANISM: Pachycondyla goeldii
<220> FEATURE:
<221> NAME/KEY: misc_feature
<223> OTHER INFORMATION: Ponericin G1

<400> SEQUENCE: 118

Gly Trp Lys Asp Trp Ala Lys Lys Ala Gly Gly Trp Leu Lys Lys Lys
1               5                   10                  15

Gly Pro Gly Met Ala Lys Ala Ala Leu Lys Ala Ala Met Gln
            20                  25                  30

<210> SEQ ID NO 119
<211> LENGTH: 24
<212> TYPE: PRT
<213> ORGANISM: Rana berlandieri
<220> FEATURE:
<221> NAME/KEY: misc_feature
<223> OTHER INFORMATION: Brevinin-1BB

<400> SEQUENCE: 119

Phe Leu Pro Ala Ile Ala Gly Met Ala Ala Lys Phe Leu Pro Lys Ile
1               5                   10                  15

Phe Cys Ala Ile Ser Lys Lys Cys
            20

<210> SEQ ID NO 120
<211> LENGTH: 20
<212> TYPE: PRT
<213> ORGANISM: Rana clamitans
<220> FEATURE:
<221> NAME/KEY: misc_feature
<223> OTHER INFORMATION: Ranalexin-1CB

<400> SEQUENCE: 120

Phe Leu Gly Gly Leu Met Lys Ala Phe Pro Ala Ile Ile Cys Ala Val
1               5                   10                  15

Thr Lys Lys Cys
            20

<210> SEQ ID NO 121
<211> LENGTH: 31
<212> TYPE: PRT
<213> ORGANISM: Rana clamitans
<220> FEATURE:
<221> NAME/KEY: misc_feature
<223> OTHER INFORMATION: Ranatuerin-2CA

<400> SEQUENCE: 121

Gly Leu Phe Leu Asp Thr Leu Lys Gly Ala Ala Lys Asp Val Ala Gly
1               5                   10                  15

Lys Leu Leu Glu Gly Leu Lys Cys Lys Ile Ala Gly Cys Lys Pro
            20                  25                  30

<210> SEQ ID NO 122
<211> LENGTH: 27
<212> TYPE: PRT
<213> ORGANISM: Rana clamitans
<220> FEATURE:
<221> NAME/KEY: misc_feature
<223> OTHER INFORMATION: Ranatuerin-2CB

<400> SEQUENCE: 122

Gly Leu Phe Leu Asp Thr Leu Lys Gly Leu Ala Gly Lys Leu Leu Gln
1               5                   10                  15

Gly Leu Lys Cys Ile Lys Ala Gly Cys Lys Pro
            20                  25

<210> SEQ ID NO 123
<211> LENGTH: 40
<212> TYPE: PRT
<213> ORGANISM: Ginkgo biloba
<220> FEATURE:
<221> NAME/KEY: misc_feature
<223> OTHER INFORMATION: Ginkbilobin

<400> SEQUENCE: 123

Ala Asn Thr Ala Phe Val Ser Ser Ala His Asn Thr Gln Lys Ile Pro
1               5                   10                  15

Ala Gly Ala Pro Phe Asn Arg Asn Leu Arg Ala Met Leu Ala Asp Leu
            20                  25                  30

Arg Gln Asn Ala Ala Phe Ala Gly
            35                  40

<210> SEQ ID NO 124
<211> LENGTH: 20
<212> TYPE: PRT
<213> ORGANISM: Basella alba
<220> FEATURE:
<221> NAME/KEY: misc_feature
<223> OTHER INFORMATION: Alpha-basrubrin (Fragment)

<400> SEQUENCE: 124

Gly Ala Asp Phe Gln Glu Cys Met Lys Glu His Ser Gln Lys Gln His
1               5                   10                  15

Gln His Gln Gly
            20

<210> SEQ ID NO 125
<211> LENGTH: 24

```
<212> TYPE: PRT
<213> ORGANISM: Pseudis paradoxa
<220> FEATURE:
<221> NAME/KEY: misc_feature
<223> OTHER INFORMATION: Pseudin 1

<400> SEQUENCE: 125

Gly Leu Asn Thr Leu Lys Lys Val Phe Gln Gly Leu His Glu Ala Ile
1               5                   10                  15

Lys Leu Ile Asn Asn His Val Gln
            20

<210> SEQ ID NO 126
<211> LENGTH: 45
<212> TYPE: PRT
<213> ORGANISM: Parabuthus schlechteri
<220> FEATURE:
<221> NAME/KEY: misc_feature
<223> OTHER INFORMATION: Parabutoporin

<400> SEQUENCE: 126

Phe Lys Leu Gly Ser Phe Leu Lys Lys Ala Trp Lys Ser Lys Leu Ala
1               5                   10                  15

Lys Lys Leu Arg Ala Lys Gly Lys Glu Met Leu Lys Asp Tyr Ala Lys
            20                  25                  30

Gly Leu Leu Glu Gly Gly Ser Glu Glu Val Pro Gly Gln
        35                  40                  45

<210> SEQ ID NO 127
<211> LENGTH: 44
<212> TYPE: PRT
<213> ORGANISM: Opistophthalmus carinatus
<220> FEATURE:
<221> NAME/KEY: misc_feature
<223> OTHER INFORMATION: Opistoporin 1

<400> SEQUENCE: 127

Gly Lys Val Trp Asp Trp Ile Lys Ser Thr Ala Lys Lys Leu Trp Asn
1               5                   10                  15

Ser Glu Pro Val Lys Glu Leu Lys Asn Thr Ala Leu Asn Ala Ala Lys
            20                  25                  30

Asn Leu Val Ala Glu Lys Ile Gly Ala Thr Pro Ser
        35                  40

<210> SEQ ID NO 128
<211> LENGTH: 44
<212> TYPE: PRT
<213> ORGANISM: Opistophthalmus carinatus
<220> FEATURE:
<221> NAME/KEY: misc_feature
<223> OTHER INFORMATION: Opistoporin 2

<400> SEQUENCE: 128

Gly Lys Val Trp Asp Trp Ile Lys Ser Thr Ala Lys Lys Leu Trp Asn
1               5                   10                  15

Ser Glu Pro Val Lys Glu Leu Lys Asn Thr Ala Leu Asn Ala Ala Lys
            20                  25                  30

Asn Phe Val Ala Glu Lys Ile Gly Ala Thr Pro Ser
        35                  40

<210> SEQ ID NO 129
<211> LENGTH: 12
<212> TYPE: PRT
<213> ORGANISM: Oncorhynchus mykiss
<220> FEATURE:
```

```
<221> NAME/KEY: misc_feature
<223> OTHER INFORMATION: Histone H2A (Fragment)

<400> SEQUENCE: 129

Ala Glu Arg Val Gly Ala Gly Ala Pro Val Tyr Leu
1               5                   10

<210> SEQ ID NO 130
<211> LENGTH: 33
<212> TYPE: PRT
<213> ORGANISM: Dolabella auricularia
<220> FEATURE:
<221> NAME/KEY: misc_feature
<223> OTHER INFORMATION: Dolabellanin B2

<400> SEQUENCE: 130

Ser His Gln Asp Cys Tyr Glu Ala Leu His Lys Cys Met Ala Ser His
1               5                   10                  15

Ser Lys Pro Phe Ser Cys Ser Met Lys Phe His Met Cys Leu Gln Gln
                20                  25                  30

Gln

<210> SEQ ID NO 131
<211> LENGTH: 35
<212> TYPE: PRT
<213> ORGANISM: Heliothis virescens
<220> FEATURE:
<221> NAME/KEY: misc_feature
<223> OTHER INFORMATION: Cecropin A

<400> SEQUENCE: 131

Arg Trp Lys Val Phe Lys Lys Ile Glu Lys Val Gly Arg Asn Ile Arg
1               5                   10                  15

Asp Gly Val Ile Lys Ala Ala Pro Ala Ile Glu Val Leu Gly Gln Ala
                20                  25                  30

Lys Ala Leu
        35

<210> SEQ ID NO 132
<211> LENGTH: 35
<212> TYPE: PRT
<213> ORGANISM: Homo sapiens
<220> FEATURE:
<221> NAME/KEY: misc_feature
<223> OTHER INFORMATION: HNP-5 Defensin

<400> SEQUENCE: 132

Gln Ala Arg Ala Thr Cys Tyr Cys Arg Thr Gly Arg Cys Ala Thr Arg
1               5                   10                  15

Glu Ser Leu Ser Gly Val Cys Glu Ile Ser Gly Arg Leu Tyr Arg Leu
                20                  25                  30

Cys Cys Arg
        35

<210> SEQ ID NO 133
<211> LENGTH: 35
<212> TYPE: PRT
<213> ORGANISM: Homo sapiens
<220> FEATURE:
<221> NAME/KEY: misc_feature
<223> OTHER INFORMATION: HNP-6 Defensin

<400> SEQUENCE: 133

Ser Thr Arg Ala Phe Thr Cys His Cys Arg Arg Ser Cys Tyr Ser Thr
1               5                   10                  15
```

```
Glu Tyr Ser Tyr Gly Thr Cys Thr Val Met Gly Ile Asn His Arg Phe
            20                  25                  30

Cys Cys Leu
        35

<210> SEQ ID NO 134
<211> LENGTH: 84
<212> TYPE: PRT
<213> ORGANISM: Holotrichia diomphalia
<220> FEATURE:
<221> NAME/KEY: misc_feature
<223> OTHER INFORMATION: Holotricin 3

<400> SEQUENCE: 134

Tyr Gly Pro Gly Asp Gly His Gly Gly His Gly Gly His Gly
1               5                   10                  15

Gly Gly His Gly Asn Gly Gln Gly Gly His Gly His Pro Gly
            20                  25                  30

Gly Gly Phe Gly Gly Gly His Gly Gly His Gly Gly Gly Arg
        35                  40                  45

Gly Gly Gly Gly Ser Gly Gly Gly Ser Pro Gly His Gly Ala Gly
50                  55                  60

Gly Gly Tyr Pro Gly Gly His Gly Gly His His Gly Gly Tyr Gln
65                  70                  75                  80

Thr His Gly Tyr

<210> SEQ ID NO 135
<211> LENGTH: 45
<212> TYPE: PRT
<213> ORGANISM: Bos taurus
<220> FEATURE:
<221> NAME/KEY: misc_feature
<223> OTHER INFORMATION: Lingual antimicrobial peptide

<400> SEQUENCE: 135

Gly Phe Thr Gln Gly Val Arg Asn Ser Gln Ser Cys Arg Arg Asn Lys
1               5                   10                  15

Gly Ile Cys Val Pro Ile Arg Cys Pro Gly Ser Met Arg Gln Ile Gly
            20                  25                  30

Thr Cys Leu Gly Ala Gln Val Lys Cys Cys Arg Arg Lys
        35                  40                  45

<210> SEQ ID NO 136
<211> LENGTH: 29
<212> TYPE: PRT
<213> ORGANISM: Rattus norvegicus
<220> FEATURE:
<221> NAME/KEY: misc_feature
<223> OTHER INFORMATION: RatNP-3

<400> SEQUENCE: 136

Cys Ser Cys Arg Thr Ser Ser Cys Arg Phe Gly Glu Arg Leu Ser Gly
1               5                   10                  15

Ala Cys Arg Leu Asn Gly Arg Ile Tyr Arg Leu Cys Cys
            20                  25

<210> SEQ ID NO 137
<211> LENGTH: 31
<212> TYPE: PRT
<213> ORGANISM: Cavia cutleri
<220> FEATURE:
<221> NAME/KEY: misc_feature
<223> OTHER INFORMATION: GNCP-1
```

<400> SEQUENCE: 137

Arg Arg Cys Ile Cys Thr Thr Arg Thr Cys Arg Phe Pro Tyr Arg Arg
1               5                   10                  15

Leu Gly Thr Cys Ile Phe Gln Asn Arg Val Tyr Thr Phe Cys Cys
            20                  25                  30

<210> SEQ ID NO 138
<211> LENGTH: 47
<212> TYPE: PRT
<213> ORGANISM: Penaeus vannamei
<220> FEATURE:
<221> NAME/KEY: misc_feature
<223> OTHER INFORMATION: Penaeidin-4a

<400> SEQUENCE: 138

His Ser Ser Gly Tyr Thr Arg Pro Leu Pro Lys Pro Ser Arg Pro Ile
1               5                   10                  15

Phe Ile Arg Pro Ile Gly Cys Asp Val Cys Tyr Gly Ile Pro Ser Ser
            20                  25                  30

Thr Ala Arg Leu Cys Cys Phe Arg Tyr Gly Asp Cys Cys His Arg
        35                  40                  45

<210> SEQ ID NO 139
<211> LENGTH: 6
<212> TYPE: PRT
<213> ORGANISM: Bos taurus
<220> FEATURE:
<221> NAME/KEY: misc_feature
<223> OTHER INFORMATION: hexapeptide

<400> SEQUENCE: 139

Arg Arg Trp Gln Trp Arg
1               5

<210> SEQ ID NO 140
<211> LENGTH: 18
<212> TYPE: PRT
<213> ORGANISM: Penaeus vannamei

<400> SEQUENCE: 140

Lys Trp Lys Leu Phe Lys Lys Ile Pro Lys Phe Leu His Leu Ala Lys
1               5                   10                  15

Lys Phe

<210> SEQ ID NO 141
<211> LENGTH: 20
<212> TYPE: PRT
<213> ORGANISM: Homo sapiens
<220> FEATURE:
<221> NAME/KEY: misc_feature
<223> OTHER INFORMATION: MUC7 20-Mer

<400> SEQUENCE: 141

Leu Ala His Gln Lys Pro Phe Ile Arg Lys Ser Tyr Lys Cys Leu His
1               5                   10                  15

Lys Arg Cys Arg
            20

<210> SEQ ID NO 142
<211> LENGTH: 21
<212> TYPE: PRT
<213> ORGANISM: Rana nigromaculata
<220> FEATURE:
<221> NAME/KEY: misc_feature
<223> OTHER INFORMATION: Nigrocin 2

<400> SEQUENCE: 142

Gly Leu Leu Ser Lys Val Leu Gly Val Gly Lys Lys Val Leu Cys Gly
1               5                   10                  15

Val Ser Gly Leu Cys
            20

<210> SEQ ID NO 143
<211> LENGTH: 33
<212> TYPE: PRT
<213> ORGANISM: Rana nigromaculata
<220> FEATURE:
<221> NAME/KEY: misc_feature
<223> OTHER INFORMATION: Nigrocin 1

<400> SEQUENCE: 143

Gly Leu Leu Asp Ser Ile Lys Gly Met Ala Ile Ser Ala Gly Lys Gly
1               5                   10                  15

Ala Leu Gln Asn Leu Leu Lys Val Ala Ser Cys Lys Leu Asp Lys Thr
            20                  25                  30

Cys

<210> SEQ ID NO 144
<211> LENGTH: 10
<212> TYPE: PRT
<213> ORGANISM: Unknown
<220> FEATURE:
<223> OTHER INFORMATION: lactoferrin (Lf) peptide 2

<400> SEQUENCE: 144

Phe Lys Cys Arg Arg Trp Gln Trp Arg Met
1               5                   10

<210> SEQ ID NO 145
<211> LENGTH: 18
<212> TYPE: PRT
<213> ORGANISM: Impatiens balsamina
<220> FEATURE:
<221> NAME/KEY: misc_feature
<223> OTHER INFORMATION: Ib-antimicrobial peptidic agent3

<400> SEQUENCE: 145

Arg His Arg Cys Cys Ala Trp Gly Pro Gly Arg Lys Tyr Cys Lys Arg
1               5                   10                  15

Trp Cys

<210> SEQ ID NO 146
<211> LENGTH: 18
<212> TYPE: PRT
<213> ORGANISM: Impatiens balsamina
<220> FEATURE:
<221> NAME/KEY: misc_feature
<223> OTHER INFORMATION: Ib-antimicrobial peptidic agent4

<400> SEQUENCE: 146

Gly Arg Arg Cys Cys Gly Trp Gly Pro Gly Arg Arg Tyr Cys Arg Arg
1               5                   10                  15

Trp Cys

<210> SEQ ID NO 147
<211> LENGTH: 14
<212> TYPE: PRT
<213> ORGANISM: Unknown
<220> FEATURE:

```
<223> OTHER INFORMATION: Synthesis dhvar4

<400> SEQUENCE: 147

Lys Arg Leu Phe Lys Lys Leu Leu Phe Ser Leu Arg Lys Tyr
1               5                   10

<210> SEQ ID NO 148
<211> LENGTH: 14
<212> TYPE: PRT
<213> ORGANISM: Unknown
<220> FEATURE:
<223> OTHER INFORMATION: Synthesis dhvar5

<400> SEQUENCE: 148

Leu Leu Leu Phe Leu Leu Lys Lys Arg Lys Lys Arg Lys Tyr
1               5                   10

<210> SEQ ID NO 149
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 149

Xaa Xaa Xaa Xaa Xaa Cys
1               5

<210> SEQ ID NO 150
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 150

Xaa Xaa Xaa Xaa Phe Cys
1               5

<210> SEQ ID NO 151
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 151

Xaa Xaa Xaa Xaa Asn Cys
1               5

<210> SEQ ID NO 152
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
```

```
<222> LOCATION: (1)..(6)
<223> OTHER INFORMATION: X = any amino acid

<400> SEQUENCE: 152

Xaa Xaa Xaa Xaa Trp Cys
1               5

<210> SEQ ID NO 153
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 153

Xaa Xaa Xaa Xaa Ile Cys
1               5

<210> SEQ ID NO 154
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 154

Xaa Xaa Xaa Xaa Thr Cys
1               5

<210> SEQ ID NO 155
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 155

Xaa Xaa Xaa Xaa Tyr Cys
1               5

<210> SEQ ID NO 156
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 156

Xaa Xaa Xaa Xaa Val Cys
1               5

<210> SEQ ID NO 157
<211> LENGTH: 6
<212> TYPE: PRT
```

```
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 157

Xaa Xaa Xaa Xaa Met Cys
1               5

<210> SEQ ID NO 158
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 158

Xaa Xaa Xaa Xaa Gly Cys
1               5

<210> SEQ ID NO 159
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 159

Xaa Xaa Xaa Xaa Glu Cys
1               5

<210> SEQ ID NO 160
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 160

Xaa Xaa Xaa Xaa Ser Cys
1               5

<210> SEQ ID NO 161
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 161

Xaa Xaa Xaa Xaa Leu Cys
1               5
```

<210> SEQ ID NO 162
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 162

Xaa Xaa Xaa Xaa Pro Cys
1               5

<210> SEQ ID NO 163
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 163

Xaa Xaa Xaa Xaa His Cys
1               5

<210> SEQ ID NO 164
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 164

Xaa Xaa Xaa Xaa Cys Cys
1               5

<210> SEQ ID NO 165
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 165

Xaa Xaa Xaa Xaa Ala Cys
1               5

<210> SEQ ID NO 166
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 166

Xaa Xaa Xaa Xaa Lys Cys
1               5

<210> SEQ ID NO 167
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 167

Xaa Xaa Xaa Xaa Gln Cys
1               5

<210> SEQ ID NO 168
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 168

Xaa Xaa Xaa Xaa Arg Cys
1               5

<210> SEQ ID NO 169
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 169

Xaa Xaa Xaa Xaa Asp Cys
1               5

<210> SEQ ID NO 170
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 170

Xaa Xaa Xaa Xaa Cys Tyr
1               5

<210> SEQ ID NO 171
<211> LENGTH: 6
<212> TYPE: PRT
<213> ORGANISM: Artificial Sequence
<220> FEATURE:

```
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 171

Xaa Xaa Xaa Xaa Cys Gln
1               5

<210> SEQ ID NO 172
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 172

Xaa Xaa Xaa Xaa Tyr Ser
1               5

<210> SEQ ID NO 173
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 173

Xaa Xaa Xaa Xaa Tyr Asp
1               5

<210> SEQ ID NO 174
<211> LENGTH: 6
<212> TYPE: PRT
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 174

Xaa Xaa Xaa Xaa Thr Gln
1               5

<210> SEQ ID NO 175
<211> LENGTH: 6
<212> TYPE: PRT
<213> ORGANISM: Artificial Sequence
<220> FEATURE:
<223> OTHER INFORMATION: Synthesized

<400> SEQUENCE: 175

Trp Thr Phe Arg Tyr Cys
1               5

<210> SEQ ID NO 176
<211> LENGTH: 6
<212> TYPE: PRT
<213> ORGANISM: Artificial Sequence
```

```
<220> FEATURE:
<223> OTHER INFORMATION: Synthesized

<400> SEQUENCE: 176

Cys Tyr Arg Phe Thr Trp
1               5

<210> SEQ ID NO 177
<211> LENGTH: 11
<212> TYPE: PRT
<213> ORGANISM: Glomerella cingulata

<400> SEQUENCE: 177

Gly Tyr Phe Ser Tyr Pro His Gly Asn Leu Phe
1               5                   10

<210> SEQ ID NO 178
<211> LENGTH: 13
<212> TYPE: PRT
<213> ORGANISM: Saccharomyces cerevisiae

<400> SEQUENCE: 178

Trp His Trp Leu Gln Leu Lys Pro Gly Gln Pro Met Tyr
1               5                   10

<210> SEQ ID NO 179
<211> LENGTH: 13
<212> TYPE: PRT
<213> ORGANISM: Saccharomyces kluyveri

<400> SEQUENCE: 179

Trp His Trp Leu Ser Phe Ser Lys Gly Gln Pro Met Tyr
1               5                   10

<210> SEQ ID NO 180
<211> LENGTH: 19
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (3)..(3)
<223> OTHER INFORMATION: Nle

<400> SEQUENCE: 180

Tyr Asn Leu Glu Asp His Pro Gln Gly Asp His Pro Lys Leu Gln Leu
1               5                   10                  15

Trp His Trp

<210> SEQ ID NO 181
<211> LENGTH: 15
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (3)..(3)
<223> OTHER INFORMATION: Nle

<400> SEQUENCE: 181

Tyr Asn Leu Glu Pro Gln Gly Pro Lys Leu Gln Leu Trp His Trp
1               5                   10                  15

<210> SEQ ID NO 182
<211> LENGTH: 13
```

```
<212> TYPE: PRT
<213> ORGANISM: Artificial Sequence
<220> FEATURE:
<223> OTHER INFORMATION: Synthesized

<400> SEQUENCE: 182

Tyr Met Pro Gln Gly Pro Lys Leu Gln Leu Phe His Trp
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Synthesized

<400> SEQUENCE: 183

Tyr Met Pro Gln Gly Pro Lys Leu Gln Leu Trp His
1               5                   10

<210> SEQ ID NO 184
<211> LENGTH: 13
<212> TYPE: PRT
<213> ORGANISM: Artificial Sequence
<220> FEATURE:
<223> OTHER INFORMATION: Synthesized

<400> SEQUENCE: 184

Tyr Met Pro Gln Gly Pro Arg Leu Asn Leu Trp His Trp
1               5                   10

<210> SEQ ID NO 185
<211> LENGTH: 26
<212> TYPE: PRT
<213> ORGANISM: Magnaporthe grisea

<400> SEQUENCE: 185

Met Ser Pro Ser Thr Lys Asn Ile Pro Ala Pro Val Ala Gly Ala Arg
1               5                   10                  15

Ala Gly Pro Ile His Tyr Cys Val Ile Met
            20                  25

<210> SEQ ID NO 186
<211> LENGTH: 24
<212> TYPE: PRT
<213> ORGANISM: Neurospora crassa

<400> SEQUENCE: 186

Met Pro Ser Thr Ala Ala Ser Thr Arg Val Pro Gln Thr Thr Met Asn
1               5                   10                  15

Phe Asn Gly Tyr Cys Val Val Met
            20

<210> SEQ ID NO 187
<211> LENGTH: 23
<212> TYPE: PRT
<213> ORGANISM: Cryphonectria parasitica

<400> SEQUENCE: 187

Met Pro Ser Asn Thr Gln Thr Ser Asn Ser Ser Met Gly Val Asn Gly
1               5                   10                  15

Tyr Ser Tyr Cys Val Val Met
            20

<210> SEQ ID NO 188
```

```
<211> LENGTH: 11
<212> TYPE: PRT
<213> ORGANISM: Magnaporthe grisea

<400> SEQUENCE: 188

Gln Trp Cys Pro Arg Arg Gly

```
<213> ORGANISM: Artificial Sequence
<220> FEATURE:
<223> OTHER INFORMATION: Synthesized
<220> FEATURE:
<221> NAME/KEY: Misc_feature
<222> LOCATION: (1)..(6)
<223> OTHER INFORMATION: X = any amino acid

<400> SEQUENCE: 194

Xaa Xaa Xaa Xaa Cys Ile
1 5

<210> SEQ ID NO 195
<211> LENGTH: 10
<212> TYPE: PRT
<213> ORGANISM: Fusarium graminearum

<400> SEQUENCE: 195

Trp Cys Gln Gln Lys Gly Gln Pro Cys Trp
1 5 10

<210> SEQ ID NO 196
<211> LENGTH: 10
<212> TYPE: PRT
<213> ORGANISM: Fusarium graminearum

<400> SEQUENCE: 196

Trp Cys Thr Trp Lys Gly Gln Pro Cys Trp
1 5 10

<210> SEQ ID NO 197
<211> LENGTH: 7
<212> TYPE: PRT
<213> ORGANISM: Artificial Sequence
<220> FEATURE:
<223> OTHER INFORMATION: Synthesized

<400> SEQUENCE: 197

Phe Arg Leu Lys Phe His Phe
1 5

<210> SEQ ID NO 198
<211> LENGTH: 6
<212> TYPE: PRT
<213> ORGANISM: Artificial Sequence
<220> FEATURE:
<223> OTHER INFORMATION: Synthesized

<400> SEQUENCE: 198

Phe Arg Leu Lys His Ile
1 5

<210> SEQ ID NO 199
<211> LENGTH: 5
<212> TYPE: PRT
<213> ORGANISM: Artificial Sequence
<220> FEATURE:
<223> OTHER INFORMATION: Synthesized

<400> SEQUENCE: 199

Phe Arg Leu His Phe
1 5

COATING COMPOSITIONS HAVING PEPTIDIC ANTIMICROBIAL ADDITIVES AND ANTIMICROBIAL ADDITIVES OF OTHER CONFIGURATIONS

PRIORITY CLAIM

This application claims priority to U.S. Provisional Application No. 60/827,531 filed Sep. 29, 2006 and is a Continuation-In-Part Application of U.S. application Ser. No. 10/884,355 filed Jul. 2, 2004, which claims priority to U.S. Provisional Application No. 60/485,234 filed Jul. 3, 2003.

BACKGROUND OF THE INVENTION

1. Field of the Invention

The present invention generally relates to coating compositions and, more specifically, coating compositions having a peptidic antimicrobial additive and an antimicrobial additive of another configuration and methods for making and using such compositions to inhibit microbial growth during liquid handling processes to prepare the coatings, in storage of the coatings, and on susceptible surfaces coated with such coating compositions.

2. Description of the Related Art

Antimicrobial biocides are substances used to destroy or suppress the growth of harmful microorganisms, such as algae, bacteria, viruses or fungi, on surfaces. Antimicrobial biocides have a wide array of applications in both public health-related products, for the control of organisms infectious to humans, and products other than those related to public health, such as preserving agents in coatings, metal working fluids and wood supports. The hurdles for biocide manufacturers are mainly regulatory in nature, as many biocides are considered toxic and/or persistent in the environment. Additionally, microorganisms that are prevalent in coatings persistently breakdown polymeric binders within coatings and are continuously adapting to achieve resistance to biocides. Some antimicrobial biocides that are considered safer to humans and the environment are available. Limitations associated with such biocides typically include a narrow target range of microorganisms, limited environmental persistence and constrained modes of biocidal action (particularly those requiring passage through the cell membrane). In addition, they often require multiple applications, higher initial concentrations/doses, and/or the use of multiple biocides to achieve the desired degree of protection.

It would, therefore, be desirable to develop biocides that are not toxic to humans, do not negatively persist in the environment, meet ever more stringent regulations and maintain activity against resistance adaptation.

BRIEF SUMMARY OF THE PREFERRED EMBODIMENTS

The problems outlined above may be in large part addressed by coating compositions having a peptidic antimicrobial additive and an antimicrobial additive of another configuration and methods for making and using such compositions to inhibit microbial growth during liquid handling processes to prepare the coatings, in storage of the coatings and on susceptible surfaces coated with such coating compositions. The following are mere exemplary embodiments of such coating compositions. The embodiments are not to be construed in any way to limit the subject matter of the claims.

An embodiment of a surface coating composition includes a peptidic antimicrobial agent consisting essentially of a contiguous amino acid sequence and an antimicrobial agent (i.e., preservative, biocide) of a different configuration (e.g., a non-peptidic antimicrobial agent, a non-amino based antimicrobial agent, a compounded peptide antimicrobial agent, or an enzyme-based antimicrobial agent). The concentrations of the different antimicrobial agents are sufficient to collectively inhibit at least a predetermined amount (i.e., any percentage up to and including 100%) of microbial growth during liquid handling processes to prepare the coating composition, in storage of the coating composition and/or on a surface coated with the coating composition. In addition, an aggregate concentration of the different antimicrobial agents within the surface coating composition is less than a weighted speculative concentration of the different antimicrobial agents to cumulatively inhibit the predetermined amount of microbial growth based upon their individual minimum inhibitory concentrations for a given microorganism.

Another embodiment of a surface coating composition includes a cysteine-free peptidic antimicrobial agent consisting essentially of a contiguous amino acid sequence having 3 to 40 amino acid residues. The coating composition further includes a preservative with a different configuration than the cysteine-free peptidic antimicrobial agent. The concentrations of the antimicrobial agents within the coating composition are sufficient to synergistically inhibit microbial growth during liquid handling processes to prepare the coating composition, in storage of the coating composition and/or on an inanimate surface coated with the surface coating composition.

Another embodiment of a surface coating composition includes a peptidic antimicrobial agent consisting essentially of a contiguous amino acid sequence and an antimicrobial agent (i.e., preservative, biocide) of a different configuration (e.g., a non-peptidic antimicrobial agent, a non-amino based antimicrobial agent, a compounded peptide antimicrobial agent, or an enzyme-based antimicrobial agent). The concentrations of the antimicrobial agents within the coating composition are sufficient to synergistically inhibit microbial growth during liquid handling processes to prepare the coating composition, in storage of the coating composition and/or on an inanimate surface coated with the surface coating composition. In addition, the concentrations of the peptidic antimicrobial agent and the antimicrobial preservative are sufficient to collectively inhibit at least a predetermined amount of microbial growth on a surface coated with the surface coating composition. Moreover, the concentrations of the different antimicrobial agents are less than their respective MIC for a given microorganism. The MIC of the antimicrobial agent having the different configuration has increased over time due to developments of the microorganism to be resistant to the antimicrobial preservative.

BRIEF DESCRIPTION OF THE DRAWINGS

Other objects and advantages of the invention will become apparent upon reading the following detailed description and upon reference to the accompanying drawings in which.

Figure 1:
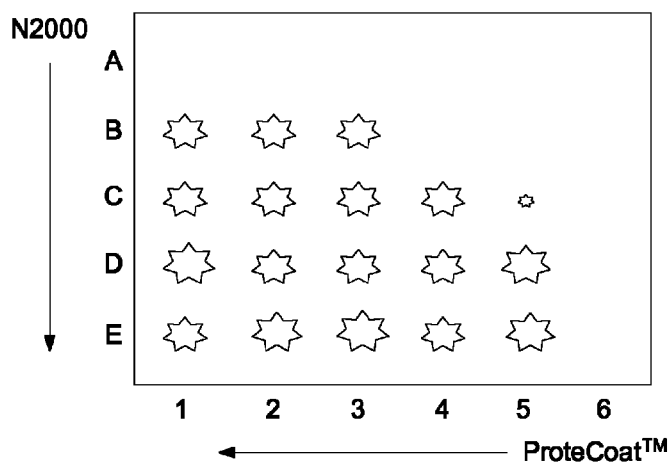
FIG. 1 illustrates an exemplary transfer blot onto growth medium graph of checkerboard plate testing solutions with various combinations of two antimicrobial agents.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

The following detailed description, specific examples and claims, while indicating the preferred embodiments of the invention, are given by way of illustration only and are considered representative of other embodiments. Accordingly, it will be readily apparent to one skilled in the art from this detailed description and the claims which follow that various changes, substitutions and modifications may be made to the invention disclosed herein without departing from the scope and spirit of the invention.

Paints and other conventional protective or decorative coating materials typically contain polymeric substances such as casein, acrylic, polyvinyl and carbon polymers (e.g., binders) which can serve as nutrients for microbial cells. Not only can these nutrient substances support the growth of microbes on paint films or coated surfaces, microbes can also grow inside cans of liquid paints and coating compositions during storage. As described in more detail below, it was an unexpected discovery that the synthetic peptidic agents described herein, when added to a range of conventional paint and coating materials, rendered such compositions and surfaces to which the coatings were applied resistant to microbial infestation and growth. It was also surprising to find that such additives worked in conjunction with conventional biocides in a coating.

A group of antimicrobial peptides that have shown compatibility and antimicrobial activity within the paint and coating mixtures described herein, or that is expected to be compatible and demonstrate antimicrobial activity within the paint and coating mixtures described herein, are disclosed in U.S. Pat. No. 6,020,312 (Edwards), U.S. Pat. No. 5,885,782 (Edwards) and U.S. Pat. No. 5,602,097 (Edwards). The disclosures of each of such patents are incorporated in their entirety herein by reference. Preferred sequences from such patents include one or more of SEQ ID Nos. 1-47 and, in some cases, particularly include one or more of SEQ ID Nos. 25-47. Additional antimicrobial peptides that are expected to demonstrate compatibility with the coatings described herein are listed in Table 1.

In some embodiments, antimicrobial additive compositions comprising equimolar mixtures of peptides produced in a synthetic peptide combinatorial library utilizing the methods described herein and/or in U.S. Pat. No. 6,020,312, U.S. Pat. No. 5,885,782, or U.S. Pat. No. 5,602,097 may be employed as antimicrobial agents in paints, coatings and films. In particular, a screening method for identifying antimicrobial peptides which are compatible and exhibit antimicrobial activity within the coatings described herein generally includes:

(a) creating a synthetic peptide combinatorial library using known methods and materials;

(b) testing a battery of microbial cells that are known to, or suspected of, infesting a building material or other object having a microbe-infestation susceptible surface with aliquots of the synthetic peptide library, wherein each aliquot comprises an equimolar mixture of peptides in which at least one of the C-terminal amino acid residues are known and which residues are in common for each peptide in the mixture;

(c) admixing said aliquots with a coating typically used on such building material/object and coating a surface with the admixture;

(d) allowing an appropriate period of time for growth of microbial cells under suitable culture conditions;

(e) comparing the growth of the treated microbial cells with untreated control cells;

(f) identifying which of the aliquots reduced the growth of the microbial cells; and, optionally, assessing the relative growth inhibitory activity of each aliquot compared to that of other aliquots (e.g., comparing $IC_{50}$ data).

TABLE 1

Antimicrobial Peptides Available for Use in the Coatings Described Herein

| Name | Source | Seq. ID | Activity |
|---|---|---|---|
| | Synthetic | 1 | Fungi |
| | Synthetic | 2 | Fungi |
| | Synthetic | 3 | Fungi |
| | Synthetic | 4 | Fungi |
| | Synthetic | 5 | Fungi |
| | Synthetic | 6 | Fungi |
| | Synthetic | 7 | Fungi |
| | Synthetic | 8 | Fungi |
| | Synthetic | 9 | Fungi |
| | Synthetic | 10 | Fungi |
| | Synthetic | 11 | Fungi |
| | Synthetic | 12 | Fungi |
| | Synthetic | 13 | Fungi |
| | Synthetic | 14 | Fungi |
| | Synthetic | 15 | Fungi |
| | Synthetic | 16 | Fungi |
| | Synthetic | 17 | Fungi |
| | Synthetic | 18 | Fungi |
| | Synthetic | 19 | Fungi |
| | Synthetic | 20 | Fungi |
| | Synthetic | 21 | Fungi |
| | Synthetic | 22 | Fungi |
| | Synthetic | 23 | Fungi |
| | Synthetic | 24 | Fungi |
| | Synthetic | 25 | Fungi |

TABLE 1-continued

Antimicrobial Peptides Available for Use in the Coatings Described Herein

| Name | Source | Seq. ID | Activity |
| --- | --- | --- | --- |
| | Synthetic | 26 | Fungi |
| | Synthetic | 27 | Fungi |
| | Synthetic | 28 | Fungi |
| | Synthetic | 29 | Fungi |
| | Synthetic | 30 | Fungi |
| | Synthetic | 31 | Fungi |
| | Synthetic | 32 | Fungi |
| | Synthetic | 33 | Fungi |
| | Synthetic | 34 | Fungi |
| | Synthetic | 35 | Fungi |
| | Synthetic | 36 | Fungi |
| | Synthetic | 37 | Fungi |
| | Synthetic | 38 | Fungi |
| | Synthetic | 39 | Fungi |
| | Synthetic | 40 | Fungi |
| | Synthetic | 41 | Fungi |
| | Synthetic | 42 | Fungi |
| | Synthetic | 43 | Fungi |
| | Synthetic | 44 | Fungi |
| | Synthetic | 45 | Fungi |
| | Synthetic | 46 | Fungi |
| | Synthetic | 47 | Fungi |
| Tachystatin A | Horseshoe Crab | 48 | Gram+ & Gram−, Fungi |
| Androctonin | *Androctonus Australis* | 49 | Gram+ & Gram−, Fungi |
| Tritrpticin | Synthetic | 50 | Gram+ & Gram−, Fungi |
| HNP-3 Defensin | Human | 51 | Gram+ & Gram−, Virus, Fungi |
| Anti-fungal protein 1 (pafp-s) | *Phytolacca Americana* | 52 | Fungi |
| Magainin 2 | Synthetic construct | 53 | Gram+ & Gram−, Fungi |
| Indolicidin | *Bos Taurus* | 54 | Gram+ & Gram−, Virus, Fungi |
| Defensin heliomicin | *Heliothis virescens* | 55 | Fungi |
| Defensin heliomicin | *Heliothis virescens* | 56 | Gram+ & Gram−, Fungi |
| Sativum defensin 1 (psd1) | Seed of Pea | 57 | Fungi |
| Gomesin | Synthetic | 58 | Gram+ & Gram−, Fungi, Mammalian cells |
| Lactoferricin B | Bovine | 59 | Gram+ & Gram−, Virus, Fungi, Cancer cells |
| PW2 | Synthetic | 60 | Fungi |
| Hepcidin 20 | Human | 61 | Fungi |
| Hepcidin 25 | Human | 62 | Fungi |
| AC-AMP2 | *Amaranthus caudatus* | 63 | Gram+, Fungi |
| NK-Lysin | *Sus scrofa* | 64 | Gram+ & Gram−, Fungi |
| Magainin 2 | African clawed frog | 65 | Gram+ & Gram−, Fungi, cancer cells |
| Melittin B | Honey bee venom | 66 | Gram+ & Gram−, Fungi, Mammalian cells |
| Thanatin | *Podisus maculiventris* | 67 | Gram+ & Gram−, Fungi |
| Antimicrobial peptide 1 | Common ice plant | 68 | Gram+ & Gram−, Fungi |
| Melanotropin alpha (Alpha-MSH) | Bovine | 69 | Gram+, Fungi |
| CORTICOSTATIN III (MCP-1) | Rabbit | 70 | Gram+ & Gram−, Virus, Fungi |
| CORTICOSTATIN III (MCP-1) | Rabbit | 71 | Gram+ & Gram−, Virus, Fungi |
| Cecropin B | Chinese oak silk moth | 72 | Gram+ & Gram−, Fungi |
| Seminalplasmin | Bovine | 73 | Gram+ & Gram−, Fungi, Mammalian cells |
| NP-3A defensin | Rabbit | 74 | Gram+ & Gram−, Virus, Fungi |
| HNP-1 Defensin | Human | 75 | Gram+ & Gram−, Virus, Fungi |
| HNP-2 Defensin | Human | 76 | Gram+ & Gram−, Virus, Fungi |
| HNP-4 Defensin | Human | 77 | Gram+ & Gram−, Fungi |
| Histatin 5 | Human | 78 | Gram+ & Gram−, Fungi |
| Histatin 3 | Human | 79 | Gram+ & Gram−, Fungi |
| Histatin 8 | | 80 | Gram+ & Gram−, Fungi |
| Tracheal antimicrobial peptide | Bovine | 81 | Gram+ & Gram−, Fungi |
| AMP1 (MJ-AMP1) | Garden four-o'clock | 82 | Gram+, Fungi |

TABLE 1-continued

Antimicrobial Peptides Available for Use in the Coatings Described Herein

| Name | Source | Seq. ID | Activity |
| --- | --- | --- | --- |
| AMP2 (MJ-AMP2) | Garden four-o'clock | 83 | Gram+, Fungi |
| MBP-1 | Maize | 84 | Gram+ & Gram−, Fungi |
| AFP2 | Rape | 85 | Fungi |
| AFP1 | Turnip | 86 | Fungi |
| AFP2 | Turnip | 87 | Fungi |
| ADENOREGULIN | Two coloured leaf frong | 88 | Gram+ & Gram−, Fungi |
| Protegrin 2 | Pig | 89 | Gram+ & Gram−, Virus, Fungi |
| Protegrin 3 | Pig | 90 | Gram+ & Gram−, Virus, Fungi |
| Histatin 1 | Crab eating macaque | 91 | Gram+ & Gram−, Fungi |
| Peptide PGQ | African clawed frog | 92 | Gram+ & Gram−, Fungi |
| Ranalexin | Bull frog | 93 | Gram+ & Gram−, Fungi |
| GNCP-2 | Guinea pig | 94 | Gram+ & Gram−, Virus, Fungi |
| Protegrin 4 | Pig | 95 | Gram+ & Gram−, Virus, Fungi |
| Protegrin 5 | Pig | 96 | Gram+ & Gram−, Virus, Fungi |
| BMAP-27 | Bovine | 97 | Gram+ & Gram−, Fungi |
| BMAP-28 | Bovine | 98 | Gram+ & Gram−, Fungi |
| Buforin I | Asian toad | 99 | Gram+ & Gram−, Fungi |
| Buforin II | Asian toad | 100 | Gram+ & Gram−, Fungi |
| BMAP-34 | Bovine | 101 | Gram+ & Gram−, Fungi |
| Tricholongin | *Trichoderma longibrachiatum* | 102 | Gram+ & Gram−, Fungi |
| Dermaseptin 1 | Sauvage's leaf frog | 103 | Gram+ & Gram−, Fungi |
| Pseudo-hevein (Minor hevin) | Para rubber tree | 104 | Fungi |
| Gaegurin-1 | Wrinkled frog | 105 | Gram+ & Gram−, Fungi |
| Skin peptide tyrosine-tyrosine | Two-colored leaf frog | 106 | Gram+ & Gram−, Fungi |
| Penaeidin-1 | Penoeid shrimp | 107 | Gram+ & Gram−, Fungi |
| Neutrophil defensin 1 (HANP-1) | Golden hamster | 108 | Gram+, Fungi |
| Neutrophil defensin 3 (HANP-3) | Golden hamster | 109 | Gram+, Fungi |
| Misgurin | Oriental weatherfish | 110 | Gram+ & Gram−, Fungi |
| PN-AMP | Japenese morning glory | 111 | Gram+, Fungi |
| Histone H2B-1 (HLP-1) (Fragment) | Rainbow trout | 112 | Gram+ & Gram−, Fungi |
| Histone H2b-3 (HLP-3) (Fragment) | Rainbow trout | 113 | Fungi |
| Neutrophil defensin 2 (RMAD-2) | Rhesus macaque | 114 | Gram+ & Gram−, Fungi |
| Termicin | Pseudacanthotermes spiniger | 115 | Gram+, Fungi |
| Spingerin | Pseudacanthotermes spiniger | 116 | Gram+ & Gram−, Fungi |
| Aurein 1.1 | Southern bell frog | 117 | Gram+ & Gram−, Fungi |
| Ponericin G! | Ponerine ant | 118 | Gram+ & Gram−, Fungi |
| Brevinin-1BB | Rio Grande leopard frog | 119 | Gram+ & Gram−, Fungi |
| Ranalexin-1CB | Gree frog | 120 | Gram+ & Gram−, Fungi |
| Ranatuerin-2CA | Green frog | 121 | Gram+ & Gram−, Fungi |
| Ranatuerin-2CB | Green frog | 122 | Gram+ & Gram−, Fungi |
| Ginkbilobin | Ginkgo | 123 | Gram+ & Gram−, Virus, Fungi |
| Alpha-basrubrin (Fragment) | Malabar spinach | 124 | Virus, Fungi |
| Pseudin 1 | Paradoxical frog | 125 | Gram+ & Gram−, Fungi |
| Parabutoporin | Scorpion | 126 | Gram+ & Gram−, Fungi, Mammalian cells |
| Opistoporin 1 | African yellow leg scorpion | 127 | Gram+ & Gram−, Fungi, Mammalian cells |
| Opistoporin 2 | African yellow leg scorpion | 128 | Gram+ & Gram−, Fungi, Mammalian cells |
| Histone H2A (fragment) | Rainbow trout | 129 | Gram+, Fungi |
| Dolabellanin B2 | Sea hare | 130 | Gram+ & Gram−, Fungi |
| Cecropin A | Nocutuid moth | 131 | Gram+ & Gram−, Fungi |
| HNP-5 Defensin | Human | 132 | Gram+ & Gram−, Fungi |
| HNP-6 Defensin | Human | 133 | Gram+ & Gram−, Fungi |
| Holotricin 3 | Holotrichia diomphalia | 134 | Fungi |

TABLE 1-continued

Antimicrobial Peptides Available for Use in the Coatings Described Herein

| Name | Source | Seq. ID | Activity |
| --- | --- | --- | --- |
| Lingual antimicrobial peptide | Bovine | 135 | Gram+ & Gram−, Fungi |
| RatNP-3 | Rat | 136 | Gram+ & Gram−, Virus, Fungi |
| GNCP-1 | Guinea pig | 137 | Gram+ & Gram−, Virus, Fungi |
| Penaeidin-4a | Penoeid shrimp | 138 | Gram+ & Gram−, Fungi |
| Hexapeptide | Bovine | 139 | Gram+ & Gram−, Virus, Fungi, Cancer cells |
| P-18 | | 140 | Gram+ & Gram−, Fungi, Cancer cells |
| MUC7 20- Mer | Human | 141 | Gram+ & Gram−, Fungi |
| Nigrocin 2 | *Rana nigromaculata* | 142 | Gram+ & Gram−, Fungi |
| Nigrocin 1 | *Rana nigromaculata* | 143 | Gram+ & Gram−, Fungi |
| Lactoferrin (Lf) peptide 2 | | 144 | Fungi |
| Ib-AMP3 | *Impatiens balsamina* | 145 | Gram+, Fungi |
| Ib-AMP4 | *Impatiens balsamina* | 146 | Gram+ Fungi |
| Dhvar4 | Synthesis | 147 | Gram+ & Gram−, Fungi |
| Dhvar5 | Synthesis | 148 | Gram+ & Gram−, Fungi |
| | Synthetic | 149 | Fungi |
| | Synthetic | 150 | Fungi |
| | Synthetic | 151 | Fungi |
| | Synthetic | 152 | Fungi |
| | Synthetic | 153 | Fungi |
| | Synthetic | 154 | Fungi |
| | Synthetic | 155 | Fungi |
| | Synthetic | 156 | Fungi |
| | Synthetic | 157 | Fungi |
| | Synthetic | 158 | Fungi |
| | Synthetic | 159 | Fungi |
| | Synthetic | 160 | Fungi |
| | Synthetic | 161 | Fungi |
| | Synthetic | 162 | Fungi |
| | Synthetic | 163 | Fungi |
| | Synthetic | 164 | Fungi |
| | Synthetic | 165 | Fungi |
| | Synthetic | 166 | Fungi |
| | Synthetic | 167 | Fungi |
| | Synthetic | 168 | Fungi |
| | Synthetic | 169 | Fungi |
| | Synthetic | 170 | Fungi |
| | Synthetic | 171 | Fungi |
| | Synthetic | 172 | Fungi |
| | Synthetic | 173 | Fungi |
| | Synthetic | 174 | Fungi |
| | Synthetic | 175 | Fungi |
| | Synthetic | 176 | Fungi |
| | Synthetic | 177 | Fungi |
| | Synthetic | 178 | Fungi |
| | Synthetic | 179 | Fungi |
| | Synthetic | 180 | Fungi |
| | Synthetic | 181 | Fungi |
| | Synthetic | 182 | Fungi |
| | Synthetic | 183 | Fungi |
| | Synthetic | 184 | Fungi |
| | Synthetic | 185 | Fungi |
| | Synthetic | 186 | Fungi |
| | Synthetic | 187 | Fungi |
| | Synthetic | 188 | Fungi |
| | Synthetic | 189 | Fungi |
| | Synthetic | 190 | Fungi |
| | Synthetic | 191 | Fungi |
| | Synthetic | 192 | Fungi |
| | Synthetic | 193 | Fungi |
| | Synthetic | 194 | Fungi |
| | Synthetic | 195 | Fungi |
| | Synthetic | 196 | Fungi |
| | Synthetic | 197 | Gram+ & Gram−, Fungi |
| | Synthetic | 198 | Gram+ & Gram−, Fungi |
| | Synthetic | 199 | Gram+ & Gram−, Fungi |

In some cases, the coatings described herein may include an antimicrobial peptidic agent which is chiefly composed of a single active peptide species. In other words, the antimicrobial peptidic agent may consist essentially of a contiguous amino acid sequence without any non-peptidic agents (e.g., aliphatic chains) coupled thereto. In general, minor amounts (less than 20% by moles) of impurities may coexist with the peptide in these compositions so long as they do not interfere with the growth inhibitory properties of the active peptide. Alternative to including a single antimicrobial peptide, the antimicrobial peptidic agent may instead be a peptide library aliquot containing a mixture of peptides in which at least two (and preferably three or four) of N-terminal amino acid residues are known. If the peptidic agent is a mixture of peptides, at least one will have antimicrobial activity. In certain situations, such as when an antimicrobial peptidic agent is being used to target an array of microbial genera or species, mixed peptide additives may be preferable. A mixed peptide antimicrobial agent may also be advantageous when there is a desire to treat or prevent infestation by a particular microbial species using lower concentrations of numerous antimicrobial peptides rather than a higher concentration of a single peptide.

It should be appreciated that it is not necessary for an amino acid sequence of a peptide having demonstrable antimicrobial activity to be completely defined for the coatings described herein. For example, in cases in which the increased cost of testing or producing a completely defined antifungal peptide is prohibitive, peptide compositions having one or more variable amino acid residues may be preferred. In some cases, it may be desirable to employ a peptide library aliquot that contains at least one antimicrobial peptide of a well-defined sequence, such as the hexapeptide of SEQ ID No. 41, but is impure to the extent that it may also include peptides of unknown exact sequence which may or may not have antimicrobial activity. In any case, a peptide or peptide library may, in some embodiments be one that has side chains blocked, is attached (e.g., covalently) to the synthetic resin or is both blocked and attached so long as sufficient antimicrobial activity is exhibited in the coating.

In the above-referenced U.S. Pat. Nos. 6,020,312; 5,885,782; and 5,602,097, an iterative process was used to identify active peptide sequences with broad spectrum antimicrobial activity. A representative method employed a hexapeptide library with the first two amino acids in each peptide chain individually and specifically defined and with the last four amino acids consisting of equimolar mixtures of 20 amino acids. Four hundred ($20^2$) different peptide mixtures each consisting of 130,321 ($19^4$) individual hexamers in which cysteine was eliminated were evaluated. In such peptide mixtures, the final concentration for each peptide was 9.38 ng/ml, in a mixture composed of 1.5 mg (peptide mix)/ml solution. This mixture profile assumed that an average peptide had a molecular weight of 785 g. In addition to a combinatorial approach for the generation of libraries of peptides, antimicrobial peptidic agents can be "intelligently" designed for both specific coatings and economy of manufacturing. For example, most amino acids occur as either of two possible isomers, designated D and L. The L-amino acids represent the vast majority of amino acids found in naturally occurring peptides and proteins, whereas D-amino acids are rarely found in nature. Although the D-form can be more stable due to resistance to proteolysis, the L-form has the advantage of economy (i.e., the L-form is both less costly to produce synthetically and can potentially be produced using a biological approach). Although the L-version of the antimicrobial additives described herein may demonstrate slightly higher MICs than their D-versions, they were still effective against the selected microbial test panel.

The testing methods described in U.S. Pat. Nos. 6,020,312; 5,885,782; and 5,602,097 may be employed to screen the peptide library for antimicrobial activity against a wide variety of microbe genera and species. In particular, the above-mentioned methods may be used to identify peptides or groups of peptides that demonstrate broad-spectrum antimicrobial activity. In addition or alternatively, the methods may be used to identify particular peptides or groups of peptides that target specific microbe genera or species. Other suitable peptide/polypeptide/protein screening methods could alternatively be used.

In any case, the methods may be configured to screen against microbial organisms that are known to, or suspected of, infesting indoor and outdoor structures, construction materials or other vulnerable materials and surfaces causing defacement (e.g., deterioration or discoloration), odor, environment hazards, and other undesirable effects. Particularly susceptible surfaces include porous materials such as stone, brick, wall board (drywall) and ceiling tiles; and semi-porous materials, including concrete, unglazed tile, stucco, grout, painted surfaces, roofing tiles, shingles, painted or treated wood and textiles. When anchorage, food and moisture are available, microbial microorganisms are able to survive where temperatures permit. As such, any type of indoor or outdoor object, structure or material that is capable of providing anchorage, food and moisture to microbial cells is potentially vulnerable to infestation with microbes. Moisture generally appears due to condensation on surfaces that are at or below the dew point for a given relative humidity. For example, fungal cells used for screening the peptide library may include members of the genera *Stachybotrys* (especially *Stachybotrys chartarum*), *Aspergillus* species (sp.), *Penicillium* sp., *Fusarium* sp., *Alternaria dianthicola*, *Aureobasidium pullulans* (aka *Pullularia pullulans*), *Phoma pigmentivora* and *Cladosporium* sp. Cell culture conditions may also be configured to provide favorable growth and proliferation conditions, as is within the capability of one of ordinary skill in the art.

It is noted that peptides of particular usefulness in the coatings described herein may exhibit variable abilities to inhibit microbial growth as adjudged by the minimal inhibitory concentrations (MIC mg/ml) and/or the concentrations necessary to inhibit growth of fifty percent of a population of microbial spores (IC50 mg/ml). MICs may range depending upon peptidic additive and target organism from about 3 to about 300 mg/ml, while IC50's may range depending upon peptidic additive and target organisms from about 2 to about 100 mg/ml. Target organisms susceptible to these amounts include *Fusarium oxysporum*, *Fusariam Sambucinum*, *Rhizoctonia Solani*, *Ceratocystis Fagacearum*, *Pphiostoma ulmi*, *Pythium ultimum*, *Magaporthe Aspergillus nidulans*, *Aspergillus fumigatus*, and *Aspergillus Parasiticus*.

The mode of action of antimicrobial peptides, polypeptides and proteins, by which they exert their inhibitory or exterminating effects, can be varied. For instance, certain peptides may operate to destabilize microbe cell membranes, while the modes of action of others may include disruptions of macromolecular synthesis or metabolism. Disruption of appressorium formation may also be the mechanism by which some peptides inhibit microbial growth (see e.g., published U.S. patent application Ser. No. 10/601,207 filed Jun. 20, 2003, expressly incorporated herein by reference in its entirety). While the modes of action of some known antimicrobial peptides have been determined, mechanisms which explain their modes of action and specificity have typically not yet been determined. Initial studies to elucidate antifungal mode of action of peptides involves a physical examination of mycelia and cells to determine if the peptides can perturb membrane functions responsible for osmotic balance. For the purposes of preparing and using antimicrobial peptides, polypeptides and/or proteins as active antimicrobial agents in paints and other coating compositions, it is not necessary to understand the mechanism by which the desired antimicrobial effect is exerted on microbe cells.

The antimicrobial peptidic additives for the coatings described herein may be constructed using a variety of amino acid precursors. The chemical structure of such amino acids (which term is used herein to include imino acids), regardless of stereoisomeric configuration, may be based upon that of the nineteen or twenty naturally-occurring amino acids: alanine (Ala; A), arginine (Arg; R), asparagine (Asn; N), aspartate (Asp; D), glutamine (Gln; Q), glutamate (Glu; E), glycine (Gly; G), histidine (His; H), isoleucine (Ile; I), leucine (Leu; L), lysine (Lys; K), methionine (Met; M), proline (Pro; P), phenylalanine (Phe; F), serine (Ser; S), threonine (Thr; T), tryptophan (Trp; W), tyrosine (Tyr; Y), and valine (Val; V). Cysteine (Cys; C) is preferably excluded to prevent disulfide linkage problems in the products. As a consequence, the antimicrobial peptidic agents described herein may, in some embodiments, by non-cyclic. The peptidic compositions may also contain amino acids which are notnaturally-occurring (e.g., norleucine), as are known to those of skill in the art. In some cases, the antimicrobial peptidic agents may be homogenous compositions containing only D-, L- or cyclic (non-racemic) amino acids. Alternatively, the antimicrobial peptidic agents may be non-homogenous, containing for instance a combination of D-, L- and/or cyclic amino acids. In yet other embodiments, the peptides may be constructed as retroinversopeptidomimetics of any of the peptides shown to be active in either the D- or L-configurations. For instance, it is known that the retroinversopeptidomimetic of SEQ ID No. (41) is inhibitory (albeit less so than either the D- or L-configurations) against certain household fungi such as *Fusarium* and *Aspergillus*.

As noted above, the coatings described herein may include one or more of the peptides disclosed in SEQ ID Nos. 1-199 and, in some embodiments, one or more of the peptide disclosed in SEQ ID Nos. 1-47. The sequences establish a number of precise chemical compositions which have been shown to have antimicrobial activity against a spectrum of microbes, but which were not previously known to be useful for treating and/or protecting building materials and other non-living objects from infestation by microbes. Antimicrobial peptidic agent compositions comprising substantially homogeneous peptide compositions, as well as mixtures of peptides derived from amino acids that are between 3 to 25 residues in length (a length readily accomplished using standard peptide synthesis procedures), especially six residues in length, are disclosed in U.S. Pat. Nos. 6,020,312; 5,885,782; and 5,602,097. A preferred antifungal peptide that inhibits or kills one or more fungus that infests and grows on the surfaces of inanimate objects is a hexapeptide having the amino acid sequence Phe Arg Leu Lys Phe His (SEQ ID No. 41).

In certain instances, the one or more peptides of the antimicrobial peptidic agents will have completely defined sequences. However, as noted above, it is not necessary for an amino acid sequence of a peptide having demonstrable antimicrobial activity to be completely defined for the coatings described herein. As such, certain peptides of SEQ ID Nos. 1-199 have somewhat variable amino acid compositions. In particular, the sequence of one or more peptides may be defined for only certain of the C-terminal amino acid residues leaving the remaining amino acid residues defined as equimolar ratios. More specifically, in each aliquot of the SPCL containing a given SEQ ID No. having a variable residue, the variable residues will each be uniformly represented in equimolar amounts by one of nineteen different naturally-occurring amino acids in one or the other stereoisomeric form. The relatively variable composition is described as an antimicrobial peptide even though it is likely that not every peptide encompassed by that general sequence will possess the same antimicrobial activity. In other embodiments, the variable residues may be rapidly defined using the method described in one or more of U.S. Pat. Nos. 6,020,312; 5,602, 097; and 5,885,782 to identify peptides that possess activity for controlling microbial growth.

In the aforementioned patents, it was demonstrated that peptides encompassed by the C-terminal sequence "XXXXRF" (SEQ ID No. 1) exhibited antifungal activity for a wide spectrum of fungi. For ease of reference, peptides are written herein in the C-terminal to N-terminal direction to denote the sequence of synthesis. However, the conventional N-terminal to C-terminal manner of reporting amino acid sequences is utilized in the Sequence Listing. In the next round of identification of antifungal peptides encompassed by the general sequence "XXXXRF" (SEQ ID No. 1) parent composition of known antifungal activity, "XXXLRF" (SEQ ID No. 9) peptides mixtures were found to exhibit significant antibiotic activity (also disclosed in U.S. Pat. Nos. 6,020,312; 5,602,097; and 5,885,782). Similar to the parent composition "XXXXRF" (SEQ ID No. 1), the "XXXLRF" (SEQ ID No. 9) peptides have a mixed equimolar array of peptides representing the same nineteen amino acid residues, some of which may have antifungal activity and some of which may not have such activity. Overall, however, the "XXXLRF" (SEQ ID No. 9) peptide composition is itself an antimicrobial agent. The identification process is carried out to the point where completely defined peptides are produced and tested for their antimicrobial activity. As a result, all amino acid residues in a six residue peptide may be defined.

It will be recognized by those of skill in the art that the peptides to be employed as antimicrobial agents for paints, coatings and other compositions, once selected, may be modified to contain functionally equivalent amino acid substitutions and yet retain the same or similar antimicrobial characteristics. It is well known that certain amino acids may be substituted for other amino acids having a similar hydropathic index or score and still retain similar if not identical biological activity. As displayed in Table 2 below, amino acids are assigned a hydropathic index on the basis of their hydrophobicity and charge characteristics. It is believed that the relative hydropathic character of the amino acid determines the secondary structure of the resultant protein, which in turn defines the interaction of the protein with the substrate molecule. Furthermore, in a peptide whose secondary structure is not a principal aspect of the interaction of the peptide, position within the peptide and the characteristic of the amino acid residue determine the interactions the peptide has in a biological system. It is proposed that biological functional equivalence may typically be maintained where amino acids having no more than a +/−1 to 2 difference in the index value, and more preferably within a +/−1 difference, are exchanged.

TABLE 2

| AMINO ACID | HYDROPATHIC INDEX |
|---|---|
| Isoleucine | 4.5 |
| Valine | 4.2 |
| Leucine | 3.8 |
| Phenylalanine | 2.8 |
| Cysteine/Cystine | 2.5 |
| Methionine | 1.9 |
| Alanine | 1.8 |
| Glycine | −0.4 |
| Threonine | −0.7 |
| Tryptophan | −0.9 |
| Serine | −0.8 |
| Tyrosine | −1.3 |
| Proline | −1.6 |
| Histidine | −3.2 |
| Glutamic Acid | −3.5 |
| Glutamine | −3.5 |
| Aspartic Acid | −3.5 |
| Asparagine | −3.5 |
| Lysine | −3.9 |
| Arginine | −4.5 |

Thus, it is expected that isoleucine, for example, which has a hydropathic index of +4.5, can be substituted for valine (+4.2) or leucine (+3.8), and still obtain a protein having similar biologic activity. Alternatively, at the other end of the scale, lysine (−3.9) can be substituted for arginine (−4.5), and so on. In general, amino acid substitutions are based on the relative similarity of R-group substituents, for example, in terms of size, electrophilic character, charge, and the like. Although these are not the only such substitutions, preferred substitutions which take various of the foregoing characteristics into consideration are listed in Table 3.

TABLE 3

| Originally Screened Residue | Exemplary Substitutions |
|---|---|
| alanine | gly; ser |
| arginine | lys |
| asparagine | gln; his |
| aspartate | glu |
| cysteine | ser |
| glutamate | asp |
| glutamine | asn |
| glycine | ala |
| histidine | asn; gln |
| isoleucine | leu; val |
| leucine | ile; val |
| lysine | arg; gln; glu |
| methionine | met; leu; tyr |
| serine | thr |
| threonine | ser |
| tryptophan | tyr |
| tyrosine | tip; phe |
| valine | ile; leu |

A variety of modifications can be made to the peptides as long as antimicrobial activity is retained. Some modifications may be used to increase the intrinsic antimicrobial potency of the peptide. Other modifications may facilitate handling of the peptide. Peptide functional groups that may typically be modified include hydroxyl, amino, guanidinium, carboxyl, amide, phenol, imidazol rings or sulfhydryl. Typical reactions of these groups include but are not limited to acetylation of hydroxyl groups by alkyl halides. Carboxyl groups may be esterified, amidated or reduced to alcohols. Carbodiimides or other catalysts may be used to catalyze the amidation of carboxyl groups. The amide groups of asparagine or glutamine may be deamidated under acidic or basic conditions. Acylation, alkylation, arylation or amidation reactions readily occur with amino groups such as the primary amino group of the peptide or the amino group of lysine residues. The phenolic group of tyrosine can be halogenated or nitrated. Examples where solubility of a peptide could be decreased include acylating charged lysine residues or acetylating the carboxyl groups of aspartic and glutamic acids. Techniques and materials that are suitable for carrying out each of these modifications are well known in the art.

Another way in which the antimicrobial activity of the peptides may be stabilized in paints and other coatings and compositions is by linking or conjugation to another molecule. Peptides may be conjugated to soluble or insoluble carrier molecules to modify their solubility properties as needed. Examples of soluble carrier molecules include polymers of polyethyleneglycol and polyvinylpyrrolidone. Alternatively, a peptide may be chemically linked or tethered to an insoluble molecule. Examples of insoluble polymers include sand or other silicates, and polystyrene, cellulose and polyvinylchloride. Such polymers are often employed in coatings. The molecular size of the conjugated polymer chosen for conjugating with an antimicrobial peptide is preferably suited for carrying out the desired additional function in the coating. Techniques and materials for conjugating peptides to other molecules are well known in the art.

Still another way in which the antimicrobial activity may be controlled or stabilized is by microencapsulating the peptides to enhance their stability in liquid coating compositions and in the final paint film or coat. For example, polyester microspheres may be used to encapsulate and stabilize the peptides in a paint composition during storage, or to provide for prolonged, gradual release of the peptide after it is dispersed in a paint film covering a surface that is vulnerable to attachment and growth of microbial cells or spores. Any suitable microencapsulation technique as would be known to one of ordinary skill in the art may be employed. Such encapsulation may enhance or confer a particulate nature to one or more antimicrobial peptide. The encapsulating membrane may provide protection to the peptide from peptidases, proteases, and other peptide bond or side chain modifying substances. In addition, the encapsulating membrane may serve to increase the average particle size of the antimicrobial peptidic agent to a desired range. Moreover, the encapsulating membrane may allow controlled release of the peptide(s) from the encapsulating material, alter surface charge, hydrophobicity, hydrophilicity, solubility and/or dispersability of the particulate material, or any combination of those functions.

An antimicrobial peptide sequence identified as described above may be grown in bacterial, insect, or other suitable cells employing techniques and materials that are well known in the art, except DNA encoding the antimicrobial peptides described herein will be used instead of a previous DNA sequence. For example, an expression vector will include a DNA sequence encoding SEQ ID No. 1 in the correct orientation and reading frame with respect to the promoter sequence to allow translation of the DNA encoding the SEQ ID No. 1. Examples of the cloning and expression of an exemplary gene and DNAs are known. Either batch culture production methods or continuous fed-batch culture methods may be employed to produce commercial-scale quantities of antifungal peptides.

Although synthetically obtained antimicrobial peptidic agents (i.e., peptides, polypeptides and proteins) that are identified and produced as described above are highly preferred, it is also possible to employ suitable naturally occurring antimicrobial peptidic agents, and microbes that produce such agents, as additives in paints and other coatings. A number of such naturally occurring peptide additives are listed in Table 1. A drawback to this is the time-consuming process of searching for naturally produced antimicrobial agents with very low-probability of success. The use of natural antimicrobial products isolated in commercial quantity from microorganisms is also limited in usefulness due in large part to purification problems. Large-scale cell culture of the antimicrobial agent-producing microorganism is required for the purification of the antimicrobial product. In many instances, the cultural isolate responsible for the production of the antimicrobial agent is not an isolate which is easily batch-cultured or it is entirely incapable of batch culturing. Furthermore, complicated purification strategies are often required to purify the active product to a reasonable level of homogeneity. Another substantial disadvantage to the use of naturally derived antimicrobial agents is the potential for co-purification of unwanted microbial byproducts, especially byproducts which are undesirably toxic.

In many cases, these factors lead to high production costs and make large-scale isolation of antimicrobial products from natural isolates impractical. Purifications may be even more difficult where racemized mixtures are possible where only a single stereoisomer is active, or where disulfide linkages are possible between peptide monomers. Even when desirable naturally occurring antimicrobial proteins or polypeptides are isolated, for example, and their amino acid sequences at least partially identified, synthesis of the native molecule, or portions thereof, may be problematic due to the need for specific disulfide bond formation, high histidine requirements, and so forth. Nonetheless, natural sources provide additional sequences to be explored as coating additives.

One or more of the antimicrobial peptides or peptide compositions, prepared as described in any of the foregoing embodiments, is mixed with a base paint or other coating, which may be any suitable commercially available product, a wide variety of which are well known in the art. Preferably the base composition is free of chemicals and other additives that are toxic to humans or animals, and/or that fail to comply with applicable environmental safety rules or guidelines. In some instances, it may be preferred to custom blend a paint or coating mixture using any combination of various naturally-occurring and synthetic components and additives that are known in the art and are also described in U.S. patent application Ser. No. 10/655,345 filed Sep. 4, 2003 or U.S. patent application Ser. No. 10/792,516 filed on Mar. 3, 2004, which are hereby expressly incorporated herein by reference in their entirety.

Coating components generally include a binder, a liquid component, a colorizing agent, one or more additives, or a combination thereof. A "binder," refers to the primary material in a coating capable of producing a film. A liquid component (e.g., a solvent, a diluent, a thinner) of a coating may refer to a material which confers and/or alters the coating's rheological properties (e.g., viscosity) to ease the application of the coating to a surface. A colorizing agent (e.g., a pigment) refers to a material which functions to alter an optical property of a coating and/or film. An additive within a coating generally refers to a composition configured to (a) reduce and/or prevent the development of a physical, chemical, and/or aesthetic defect in the coating and/or film; (b) confer some additional desired property to a coating and/or film; or (c) a combination thereof. The content for an individual coating additive in a coating generally is 0.0001% to 20.0%, including all intermediate ranges and combinations thereof. However, in many instances it is preferred if the concentration of a single additive in a coating comprises between 0.0001% and 10.0%, including all intermediate ranges and combinations thereof.

Some of the usual types of components of paints and coatings are summarized as follows:

Binders: oil-based resins (e.g., oils, alkyd resins, oleoresinous binders, and fatty acid epoxy esters); polyester resins; modified cellulose; polyamide; amidoamine; amino resins; urethanes; phenolic resins; epoxy resins; polyhydroxyether; acrylic resins; polyvinyl binders; rubber resins; bituminous; polysulfide and silicone.

Liquid Components: solvents; thinners; diluents; plasticizers; and water (e.g., hydrocarbons; oxygenated solvents; chlorinated hydrocarbons, nitrated hydrocarbons, other organic liquids).

Colorants: pigments and dyes.

Additives: accelerator, an adhesion promoter, an antifloating agent, an antiflooding agent, an antifoaming agent, an anti-insect additive, an antioxidant, an antiskinning agent, a buffer (e.g., ammonium bicarbonate, both monobasic and dibasicphosphate buffers, Trizma base and zwitterionic buffers), a catalyst (e.g., driers, acids, bases, urethane catalysts), a coalescing agent, a corrosion inhibitor, a defoamer, a dehydrator, a dispersant, a drier, an electrical additive (e.g., an electrolyte), an emulsifier, a film-formation promoter, a fire retardant, a flow control agent, a gloss aid, a leveling agent, a light stabilizer, a marproofing agent, a matting agent, a neutralizing agent, a preservative, a rheology modifier, a slip agent, a viscosity control agent and a wetting agent.

The term preservative refers to an additive that reduces or prevents the deterioration of a coating and/or film by a microorganism, specifically by killing and/or preventing the growth of an organism. Examples of preservatives include, for example, bactericides, fungicides, algaecides, or combinations thereof. In some cases, a preservative may alternatively be referred to as a biocide. Based on the function of a preservative within a coating, the antimicrobial peptidic agents described herein may be employed as preservatives. In general, a preservative may be directly admixed with the coating, applied as a primer coating, applied as an overcoat, or any combination of these application techniques. As such, a preservative may be an in-can preservative, an in-film preservative, or a combination thereof. An in-can preservative refers to a composition that reduces or prevents the growth of a microorganism prior to film formation. Typically, an in-can preservative is added to a coating composition for function during coating preparation, storage, or a combination thereof. Addition of an in-can preservative during a water-borne coating production typically occurs with the introduction of water to a coating composition. An in-film preservative refers to a composition that reduces or prevents the growth of a microorganism after film formation. Oftentimes an in-film preservative is the same chemical as an in-can preservative, but added to a coating composition at a higher (e.g., two-fold) concentration for continuing activity after film formation.

In some cases, an antimicrobial peptidic agent described herein may be used as a partial or complete substitute ("replacement") for another biocide (i.e., preservative) within a coating. In particular, it is contemplated that 0.0001% to 100%, including all intermediate ranges, of a conventional antimicrobial component (i.e., biocide/preservative) in a coating formulation may be substituted by one of the antimicrobial peptidic agents described herein. In some formulations, the concentration of antimicrobial peptidic agent may exceed 100%, by weight or volume, of the conventional antimicrobial component that is being replaced. As such, it is contemplated that an antimicrobial peptidic agent described herein may replace equivalents of 0.001% to 500% (by weight or by volume) of a conventional antimicrobial component within a coating, including all intermediate ranges. For example, to produce a coating with similar microbial resistance as a non-substituted formulation, it may require replacing 70% of a chemical biocide (e.g., 0.7 kg) with the equivalent of 127% (e.g., 1.27 kg) of antimicrobial peptidic agent. In an alternative exemplary embodiment, to produce a coating with similar microbial resistance properties as a non-substituted formulation, it may require that 20% (e.g., 0.2 kg) of a chemical biocide may be replaced by 10% (e.g., 0.1 kg) of an antimicrobial peptidic agent. It is noted that such embodiments are merely exemplary. Any variation of substitutions may be considered, depending on the design specifications of the coating.

Alternative to replacing a conventional preservative within a coating composition, one of the antimicrobial peptidic agents described herein may be included in a coating in addition to one or more conventional preservatives. As described in more detail below, it was discovered in conjunction with the development of the antimicrobial peptidic agents described herein that the agents in such cases may be configured to work synergistically with other preservatives in a coating. Regardless of whether the antimicrobial peptidic agents described herein are used alone or in combination with other preservatives, the various assays described herein may be used to determine the microbial resistance properties of a composition (e.g., a coating, a film) produced by direct addition of an antimicrobial peptidic agent and/or substitution of some or all of the conventional antimicrobial components within a coating.

In general, conventional preservatives have a distinct structure from the antimicrobial peptidic agents described herein. In particular, conventional preservatives generally do not consist essentially of a contiguous amino acid sequence, much less with the different configurations described herein with respect to the number amino acid residues in the sequence and possible non-cyclic structure. Rather, many conventional preservatives do not even include peptidic chains. Such conventional preservatives may generally be referred to herein as "non-peptidic antimicrobial agents". Furthermore, some conventional preservatives do not even include an amino acid of any kind, much less a peptidic chain. Such preservatives are generally referred to herein as "non-amino based antimicrobial agents". It is noted that a few antimicrobial preservatives exist which include a peptide chain, but such preservatives generally include one or more non-peptidic agents (e.g., aliphatic chains) coupled thereto. Such preservatives may generally be referred to herein as "compounded peptidic antimicrobial agents". Furthermore, a few antimicrobial preservatives exist which include amino acid polymers, specifically which are enzyme-based. Such preservatives may generally be referred to herein as "enzyme-based antimicrobial agents."

Examples of conventional preservatives that have been used in coatings include a metal compound (e.g., an organo-metal compound) biocide, an organic biocide, or a combination thereof. Examples of a metal compound biocide include barium metaborate (CAS No. 13701-59-2), which is a fungicide and bactericide; copper (II) 8-quinolinolate (CAS No. 10380-28-6), which is a fungicide; phenylmercuric acetate (CAS No. 62-38-4), tributyltin oxide (CAS No. 56-35-9), which is less preferred for use against Gram-negative bacteria; tributyltin benzoate (CAS No. 4342-36-3), which is a fungicide and bactericide; tributyltin salicylate (CAS No. 4342-30-7), which is a fungicide; zinc 2-pyridinethiol-N-oxide (CAS No. 13463-41-7), which is a fungicide; zinc oxide (CAS No. 1314-13-2), which is a fungistatic/fungicide and algaecide; a combination of zinc-dimethyldithiocarbamate (CAS No. 137-30-4) and zinc 2-mercaptobenzothiazole (CAS No. 155-04-4), which acts as a fungicide; zinc 2-pyridinethiol-N-oxide (CAS No. 13463-41-7), which is a fungicide; a metal soap; or a combination thereof. Examples of metals comprised in a metal soap biocide include copper, mercury, tin, zinc, or a combination thereof. Examples of an organic acid comprised in a metal soap biocide include a butyl oxide, a laurate, a naphthenate, an octoate, a phenyl acetate, a phenyl oleate, or a combination thereof.

An example of an organic biocide that acts as an algaecide includes 2-methylthio-4-tert-butylamino-6-cyclopropylamino-s-triazine (CAS No. 28159-98-0). Examples of an organic biocide that acts as a bactericide include a combination of 4,4-dimethyl-oxazolidine (CAS No. 51200-87-4) and 3,4,4-trimethyloxazolidine (CAS No. 75673-43-7); 5-hydroxy-methyl-1-aza-3,7-dioxabicylco (3.3.0.) octane (CAS No. 59720-42-2); 2(hydroxymethyl)-aminoethanol (CAS No. 34375-28-5); 2-(hydroxymethyl)-amino-2-methyl-1-propanol (CAS No. 52299-20-4); hexahydro-1,3,5-triethyl-s-triazine (CAS No. 108-74-7); 1-(3-chloroallyl)-3,5,7-triaza-1-azonia-adamantane chloride (CAS No. 51229-78-8); 1-methyl-3,5,7-triaza-1-azonia-adamantane chloride (CAS No. 76902-90-4); p-chloro-m-cresol (CAS No. 59-50-7); an alkylamine hydrochloride; 6-acetoxy-2,4-dimethyl-1,3-dioxane (CAS No. 828-00-2); 5-chloro-2-methyl-4-isothiazolin-3-one (CAS No. 26172-55-4); 2-methyl-4-isothiazolin-3-one (CAS No. 2682-20-4); 1,3-bis(hydroxymethyl)-5,5-dimethylhydantoin (CAS No. 6440-58-0); hydroxymethyl-5,5-dimethylhydantoin (CAS No. 27636-82-4); or a combination thereof.

Examples of an organic biocide that acts as a fungicide include a parabens; 2-(4-thiazolyl)benzimidazole (CAS No. 148-79-8); N-trichloromethyl-thio-4-cyclohexene-1,2-dicarboximide (CAS No. 133-06-2); 2-n-octyl-4-isothiazoline-3-one (CAS No. 26530-20-1); 2,4,5,6-tetrachloro-isophthalonitrile (CAS No. 1897-45-6); 3-iodo-2-propynyl butyl carbamate (Cas No. 55406-53-6); N-(trichloromethyl-thio)phthalimide (Cas No. 133-07-3); tetrachloroisophthalonitrile (Cas No. 1897-45-6); potassium N-hydroxy-methyl-N-methyl-dithiocarbamate (Cas No. 51026-28-9); sodium 2-pyridinethiol-1-oxide (Cas No. 15922-78-8); or a combination thereof. Examples of a parbens include butyl parahydroxybenzoate (Cas No. 94-26-8); ethyl parahydroxybenzoate (Cas No. 120-47-8); methyl parahydroxybenzoate (Cas No. 99-76-3); propyl parahydroxybenzoate (Cas No. 94-13-3); or a combination thereof.

Examples of an organic biocide that acts as an bactericide and fungicide include 2-mercaptobenzo-thiazole (Cas No. 149-30-4); a combination of 5-chloro-2-methyl-3(2H)-isothiazoline (Cas No. 26172-55-4) and 2-methyl-3(2H)-isothiazolone (Cas No. 2682-20-4); a combination of 4-(2-nitrobutyl)-morpholine (Cas No. 2224-44-4) and 4,4'-(2-ethylnitrotrimethylene dimorpholine (Cas No. 1854-23-5); tetra-hydro-3,5-di-methyl-2H-1,3,5-thiadiazine-2-thione (Cas No. 533-74-4); potassium dimethyldithiocarbamate (Cas No. 128-03-0); or a combination thereof. An example of an organic biocide that acts as an algaecide and fungicide includes diiodomethyl-p-tolysulfone (Cas No. 20018-09-1). Examples of an organic biocide that acts as an algaecide, bactericide and fungicide include glutaraldehyde (CAS No. 111-30-8); methylenebis(thiocyanate) (Cas No. 6317-18-6); 1,2-dibromo-2,4-dicyanobutane (CAS No. 35691-65-7); 1,2-benzisothiazoline-3-one (Cas No. 2634-33-5); 2-(thiocyanomethyl-thio)benzothiazole (CAS No. 21564-17-0); or a combination thereof. An example of an organic biocide that acts as an algaecide, bactericide, fungicide and molluskicide includes 2-(thiocyanomethyl-thio)benzothiozole (CAS No. 21564-17-0) and methylene bis(thiocyanate) (CAS No. 6317-18-6).

In certain situations of use, an applicable environmental law or regulation may encourage the selection of an organic biocide such as a benzisothiazolinone derivative. An example of a benzisothiazolinone derivative is Busan™ 1264 (Buckman Laboratories, Inc.), Proxel™ GXL (Avecia Inc.), or Preventol® VP OC 3068 (Bayer Corporation), which comprises 1,2-benzisothiazolinone (CAS No. 2634-33-5). In the case of Busan™ 1264, the primary use is a bactericide and/or fungicide at 0.03% to 0.5% in a water-borne coating.

Often, conventional preservatives are proprietary commercial formulations and/or compounds sold under tradenames. Examples include organic biocides under the tradename Nuosept® (International Specialty Products), which are typically used in a water-borne coating. Specific examples of a Nuosept® biocide includes Nuosept® 95, which comprises a mixture of bicyclic oxazolidines, and is typically added to 0.2% to 0.3% concentration to a coating composition; Nuosept® 145, which comprises an amine reaction product, and is typically added to 0.2% to 0.3% concentration to a coating composition; Nuosept® 166, which comprises 4,4-dimethyloxazolidine (CAS No. 51200-87-4), and is typically added to 0.2% to 0.3% concentration to a basic pH water-borne coating composition; or a combination thereof. A further example is Nuocide® (International Specialty Products) biocides, which are typically used fungicides and/or algaecides. Examples of a Nuocide® biocide is Nuocide® 960, which comprises 96% tetrachlorisophthalonitrile (CAS No. 1897-45-6), and is typically used at 0.5% to 1.2% in a water-borne or solvent-borne coating as a fungicide; Nuocide® 2010, which comprises chlorothalonil (CAS No. 1897-45-6) and IPBC(CAS No. 55406-53-6) at 30%, and is typically used at 0.5% to 2.5% in a coating as a fungicide and algaecide; Nuocide® 1051 and Nuocide® 1071, each which comprises 96% N-cyclopropyl-N-(1-dimethylethyl)-6-(methylthio)-1,3,5-triazine-2,4-diamine (CAS No. 28159-98-0), and is typically used as an algaecide in antifouling coatings at 1.0% to 6.0% or water-based coatings at 0.05% to 0.2%, respectively; and Nuocide® 2002, which comprises chlorothalonil (CAS No. 1897-45-6) and a triazine compound at 30%, and is typically used at 0.5% to 2.5% in a coating and/or a film as a fungicide and algaecide.

An additional example of a tradename biocide for coatings includes Vancide® (R. T. Vanderbilt Company, Inc.). Examples of a Vancide® biocide include Vancide® TH, which comprises hexahydro-1,3,5-triethyl-s-triazine (CAS No. 108-74-7), and is generally used in a water-borne coating; Vancide® 89, which comprises N-trichloromethylthio-4-cyclohexene-1,2-dicarboximide (CAS No. 133-06-2) and related compounds such as captan (CAS No. 133-06-2), and is used as a fungicide in a coating composition; or a combination thereof. A bactericide and/or fungicide for coatings, particularly a water-borne coating, is a Dowicil™ (Dow Chemical Company). Examples of a Dowicil™ biocide include Dowicil™ QK-20, which comprises 2,2-dibromo-3-nitrilopropionamide (CAS No. 10222-01-2), and is used as a bactericide at 100 ppm to 2000 ppm in a coating; Dowicil™ 75, which comprises 1-(3-chloroallyl)-3,5,7-triaza-1-azoniaadamantane chloride (CAS No. 51229-78-8), and is used as a bactericide at 500 ppm to 1500 ppm in a coating; Dowicil™ 96, which comprises 7-ethyl bicyclooxazolidine (CAS No. 7747-35-5), and is used as a bactericide at 1000 ppm to 2500 ppm in a coating; Bioban™ CS-1135, which comprises 4,4-dimethyloxazolidine (CAS No. 51200-87-4), and is used as a bactericide at 100 ppm to 500 ppm in a coating; or a combination thereof. An additional example of a tradename biocide for coatings includes Kathon® (Rohm and Haas Company). An example of a Kathon® biocide includes Kathon® LX, which typically comprises 5-chloro-2-methyl-4-isothiazolin-3-one (CAS no 26172-55-4) and 2-methyl-4-isothiazolin-3-one (CAS no 2682-20-4) at 1.5%, and is added from 0.05% to 0.15% in a coating.

Examples of tradename fungicides and algaecides include those described for Fungitrol® (International Specialty Products), which are often formulated for solvent-borne and water-borne coatings, and in-can and film preservation. An example is Fungitrol® 158, which comprises 15% tributyltin benzoate (CAS No. 4342-36-3) (15%) and 21.2% alkylamine hydrochlorides, and is typically used at 0.35% to 0.75% in a water-borne coating for in-can and film preservation. An additional example is Fungitrol® 11, which comprises N-(trichloromethylthio) phthalimide (CAS No. 133-07-3), and is typically used at 0.5% to 1.0% as a fungicide for solvent-borne coating. A further example is Fungitrol® 400, which comprises 98% 3-iodo-2-propynl N-butyl carbamate ("IPBC") (Cas No. 55406-53-6), and is typically used at 0.15% to 0.45% as a fungicide for a water-borne or a solvent-borne coating. The aforementioned products are available from a number of companies including Arch Chemical, Inc. of Norwalk, Conn.; Avecia Protection & Hygiene of Wilimington, Del.' BASF Corporation of Mount Olive, N.J.; Buckman Laboratories, Inc. of Memphis, Tenn.; Cognis Corporation of Ambler, Pa.; International Specialty Products of Wayne, N.J.; Rohm and Haas Company of Philadelphia, Pa.; and Troy Corporation of Florham Park, N.J.

As noted above, the antimicrobial peptidic agents described herein may be configured to work synergistically with conventional preservatives. In particular, combining an antimicrobial peptidic agent with conventional preservatives within a coating may provide antimicrobial activity over and above that seen with either of the preservatives alone. More specifically, combining an antimicrobial peptidic agent with conventional preservatives within a coating may provide a higher degree of microbial growth inhibition than what may be expected if inhibitory activity of the combination is assumed to be additive (i.e., calculated by summing the inhibition levels of each component alone). Such conventional preservatives may include any classification of preservatives noted above, specifically non-peptidic antimicrobial agents, non-amino based antimicrobial agents, compounded peptide antimicrobial agents, and enzyme-based antimicrobial agents.

It is further contemplated that the antimicrobial peptidic agents described herein may additionally or alternatively be included with non-conventional preservatives within a coating and exhibit synergistic effects. In particular, it is believed the antimicrobial peptidic agents described herein may be configured to work synergistically with preservatives which are not commonly known at the time of the filing of the captioned application (i.e., preservatives developed subsequent to the antimicrobial peptidic agents described herein). In other words, it is believed that it would be obvious to one skilled in the art based on the disclosure herein to configure the antimicrobial peptidic agents described herein to work synergistically with any newly developed preservative. Such newly developed preservatives may include any classification of preservatives noted above, specifically non-peptidic antimicrobial agents, non-amino based antimicrobial agents, compounded peptide antimicrobial agents, and enzyme-based antimicrobial agents.

The term "synergistic", as used herein, may generally refer to an interaction between combined elements that produces increased effectiveness of at least one of the elements relative to the effectiveness of that element taken alone. Following such a definition, it is contemplated that the antimicrobial peptidic agents described herein may be combined with antimicrobial agents of different configurations (i.e., conventional or non-conventional biocides having different configurations than the antimicrobial peptidic agents described herein including non-peptidic antimicrobial agents, non-amino based antimicrobial agents, compounded peptide antimicrobial agents, and enzyme-based antimicrobial agents) in a coating and the combination may produce increased antimicrobial activity of at least one of the agents relative to the effectiveness of that agent taken alone. As described above, the typical mode of action of the antimicrobial peptidic agents described herein is to disrupt the exterior cell membrane of a microbe to inhibit its growth. Such a mode of action may be increased in the presence of another preservative or serve to increase the effectiveness of another preservative within a coating to produce a synergistic effect. For example, it is contemplated that the disruption of exterior cell membranes of microbes by the antimicrobial peptidic agents described herein may allow the interior of the cells to be more accessible for preservatives which have a mode of action targeting the interior of the cells to inhibit microbial growth. In addition or alternatively, growth rates of microbes may be synergistically inhibited when the antimicrobial peptidic agents described herein are combined with preservatives which target different sites along exterior portions of a microbial cell membrane than the antimicrobial peptidic agents. In general, there are three generally accepted mechanisms of synergistic activity: a) increase, by one agent the permeability of the cell wall and membranes to the second agent, b) inhibition to degrade the second agent, and c) double blocking by the two components of successive steps in a metabolic sequence.

A surface coating composition is contemplated herein which includes a peptidic antimicrobial agent consisting essentially of a contiguous amino acid sequence and an antimicrobial agent (i.e., preservative, biocide) of a different configuration (e.g., a non-peptidic antimicrobial agent, a non-amino based antimicrobial agent, a compounded peptide antimicrobial agent, or an enzyme-based antimicrobial agent). The concentrations of the different antimicrobial agents are sufficient to synergistically inhibit microbial growth during liquid handling processes to prepare the coating composition, in storage of the coating composition and/or on a surface coated with the coating composition. In some embodiments, the concentrations of the antimicrobial agents may be sufficient to collectively inhibit at least a predetermined amount (i.e., any percentage up to and including 100%) of microbial growth during liquid handling processes to prepare the coating composition, in storage of the coating composition and/or on a surface coated with the coating composition.

Based on the aforementioned definition of synergistic, an aggregate concentration of the antimicrobial agents within the coating composition may, in some embodiments, be less than a speculative concentration of the antimicrobial agents to cumulatively inhibit the predetermined amount of microbial growth based upon their individual minimum inhibitory concentrations (MIC) for a given microorganism. MIC is referred to herein as the lowest concentration of particular antimicrobial agent in a solution at which no growth of a target microorganism is observed over a given period of time (i.e., lowest concentration at which 100% growth inhibition is exhibited).

By way of example, take an embodiment in which an antimicrobial peptidic agent described herein exhibits approximately 25% growth inhibition against a particular microorganism at a concentration of approximately 1.0 ppm within a coating (i.e., when the antimicrobial peptidic agent is the only preservative within the coating). In comparison, the growth inhibition of the microorganism for a preservative having a different configuration within such a coating is approximately 50% at a concentration of approximately 5.0 ppm (i.e., when the preservative is the only preservative within the coating). It is noted that such concentrations do not exhibit 100% growth inhibition and, therefore, do not represent the MICs for the agents. Such values, however, extend from the MICs for the agents and, thus, such information is based on the MICs of the agents. Assuming the growth inhibitions of the agents are additive when combined within a coating, a weighted speculative concentration of approximately 6 ppm (i.e., approximately 1.0 ppm of the antimicrobial peptidic agent and approximately 5.0 ppm of the other preservative) would produce a growth inhibition of approximately 75%. Due to synergism between the components, however, an aggregate concentration of the agents may be reduced relative to such a speculative concentration to attain 75% growth inhibition. For example, an aggregate concentration of the agents may be 3 ppm (i.e., approximately 0.5 ppm of the antimicrobial peptidic agent and approximately 2.5 ppm of the other preservative) to attain 75% growth inhibition. Larger or smaller aggregate concentrations (as well as concentrations of the individual agents) may be considered, depending on the characteristics of the coating, the target microorganism and the selected preservatives.

Although the embodiments described herein are not necessarily so limited, in some cases, it may be advantageous to configure an aggregate concentration of agents to be less than or equal to about 75% of a speculative concentration of the agents or, more specifically, less than or equal to about 50% of the speculative concentration. Furthermore, although the aforementioned embodiment reduces the concentrations of the individual agents by the same proportion to obtain the aggregate concentration, the coatings described herein are not so limited. In particular, the concentrations of individual agents may be independently varied to obtain an aggregate concentration within a coating. In some embodiments, not all concentrations of agents may be reduced relative to the values referred to when the agents are used independently within the coatings. For example, with regard to the example noted above, an alternative composition of a 3 ppm aggregate concentration may include 1.0 ppm of an antimicrobial agent described herein and approximately 2.0 ppm of a preservative with a different configuration. Such variation among the concentrations of the individual agents may be attributed to the effect one agent may have on another to produce the synergistic effect. A determination of target concentrations for agents to inhibit concentrations of one or more particular microorganisms within a coating may generally be performed by the methods described below. As described in more detail below, the synergistic effects of coatings having different preservatives, including antimicrobial peptidic agents, may not only be determined, but the concentrations of the preservatives may also be "tuneable" to particular coatings and microorganisms. In any case, for an embodiment in which an aggregate concentration of agents is less than a speculative concentration of such agents for predetermined growth inhibition, the concentration of one or both of the agents may be less than their respective MIC for a given microorganism.

Alternative to the embodiment noted above, a coating may be configured to have an aggregate concentration of an antimicrobial peptidic agent described herein and one or more antimicrobial agents of different configurations greater than or equal to a speculative concentration of such agents to produce a particular growth inhibition rate. In such cases, the resultant growth inhibition rate will be greater than the rate if the agents were assumed additive. For example, taking the concentrations and growth rates of the agents noted in the aforementioned embodiment, an aggregate concentration of 6 ppm of the agents will produce a growth inhibition greater than approximately 75%.

It is further noted that in cases in which a coating exhibits 100% growth inhibition, synergism between agents may occur even if the aggregate concentration of antimicrobial agents within the coatings is not less than a speculative amount to produce the 100% growth inhibition. In particular, take an embodiment in which an antimicrobial peptidic agent described herein exhibits 50% growth inhibition against a particular microorganism at a concentration of approximately 0.7 ppm within a coating (i.e., when the antimicrobial peptidic agent is the only preservative within the coating). In comparison, a growth inhibition of the microorganism for a preservative having a different configuration is approximately 50% at a concentration of approximately 3.0 ppm within such a coating (i.e., when the preservative is the only preservative within the coating). Assuming the microbial activity of the components is additive, a weighted speculative concentration 3.7 ppm (i.e., 0.7 ppm of the antimicrobial peptidic agent and 3.0 ppm of the other preservative) of the agents would produce a growth inhibition of 100%. In such a case, even if an aggregate concentration of the agents is greater than or equal to 3.7 ppm, synergism between the agents may still exist, but such effects may not be readily noticeable since 100% growth inhibition is attained.

An advantage of synergistic activity between an antimicrobial peptidic agent described herein and one or more preservatives of different configurations is that broad-spectrum biodical may be attained. In addition, biocidal activity of preservatives may be increased. Furthermore, biocidal activity may additionally or alternatively be retained within a coating for a longer duration. Moreover, effective doses of one or more of the antimicrobial agents may be reduced within a coating. With true synergism, it is possible to reduce the application rate of the antimicrobials without sacrificing control. A further advantage is the potential to revive the use of biocides to which pathogens have developed resistance. For example, *Fusarium sambucinum* Fuckel (telomorph *Gibberella pulicaris* (Fries) Sacc.) causes dry rot of potatos during storage. Since the early 1970s, thiabendazole (TBZ) has been used extensively as a systemic benzimidazole fungicide for the control of fruit and vegetable diseases. It is highly persistent; the field half-life for thiabendazole has been reported as 403 days. Resistance to thiabendazole has been reported in strains of *F. sambucinum* from the United States, Canada and the European Union. Studies combining TBZ and antimicrobial peptidic agents demonstrated that synergistic activity allowed for a reduction in the effective doses of TBZ and demonstrated the potential to act against fungicide-resistant pathogens individually and in a synergistic manner at low concentrations. This ability to synergistically "revive" established biocides can save both time and money, as it provides an enhanced control compared to applying each of the materials separately.

Further to such an advantage of synergism, a surface coating composition is contemplated herein which includes a peptidic antimicrobial agent consisting essentially of a contiguous amino acid sequence in a concentration less than its MIC for a given microorganism. The coating composition further includes a preservative with a different configuration having a concentration less than its MIC for the given microorganism, wherein the MIC of the preservative has increased over time due to developments of the microorganism to be resistant to the preservative. In such a coating composition, the concentrations of the antimicrobial agents are sufficient to collectively inhibit at least a predetermined amount (up to and including 100%) of microbial growth during liquid handling processes to prepare the coating composition, in storage of the coating composition and/or on a surface coated with the surface coating composition. Although not so limited, it is contemplated that one or both of the agents in such a coating composition may have a concentration less than approximately 50% of their MIC for the given microorganism and, in particularly cases, less than approximately 25% of their MIC.

A further surface coating composition contemplated herein includes a cysteine-free peptidic antimicrobial agent consisting essentially of a contiguous amino acid sequence having 3 to 40 amino acid residues. The coating composition further includes a preservative with a different configuration, wherein concentrations of the antimicrobial agents are sufficient to synergistically inhibit microbial growth during liquid handling processes to prepare the coating composition, in storage of the coating composition and/or on an inanimate surface coated with the surface coating composition. It is noted that the specific configurations of coating compositions noted above may be modified with any of the characteristics described herein with respect to coatings, including those which are specific to the antimicrobial agents as wells other components of the coatings. In particular, the coatings described herein are not necessarily restricted to the embodiments in which they are described.

In the development of the coatings described herein, biocide synergism experiments were conducted with three broad-spectrum biocides commonly used in waterborne coatings augmented with the one of the peptidic antimicrobial additives described herein. In particular, biocides of Rohm & Haas Kathon LX 1.5% (active biocide ingredient: 2-methyl-4-isothiazolin-3-one), Troy Corp. Polyphase (active biocide ingredient: 3-iodo-2-propynyl butyl carbamate) and Verichem N2000 (active biocide ingredient: dodecylguanidine) were each used singularly in combination with one of the peptidic antimicrobial additives described herein. The rationale for selecting each biocide was as follows: Kathon LX 1.5% is a common in-can preservative; Polyphase is a common iodo type additive that works in films after application; and Verichem N2000 provides in-can and in-solution (e.g., water cooling facilities) control against algae, bacteria, fungi and yeasts.

As set forth below, it was found that when these biocides (specifically the active biocide ingredients of the preservatives) were combined in a coating with an antimicrobial peptidic agent comprising the sequence denoted in SEQ ID No. 41, the preservatives exhibited a synergistic effect against particular microorganisms. The particular microorganisms tested were *Bacillus atrophaeus* (*B. atrophaeus*), *Fusarium oxysporum* f. sp. lycopersici (*F. oxysporum*) and *Aspergillus nidulans* (*A. nidulans*). *B. atrophaeus* is a gram-positive spore-forming bacteria and a commonly used, less dangerous, surrogate of *Bacillus anthracis*, the causative agent for anthrax. *A. nidulans* is a model microorganism and a less dangerous surrogate of *Aspergillus fumigatus*, which is a potentially deadly human pathogen and a major allergen. *Fusarium oxysporum*, the causal agent of vascular wilt disease in plants, is an emerging opportunistic human pathogen.

Although the environment of the paint film is significantly more complex, synergistic interactions of this type indicate a potential for antimicrobial peptidic agents to enhance the activity of other biocides currently in use for the control of pathogens and microbial pests. As such, it is expected that these and other synergistic combinations of peptidic antimicrobial agents and antimicrobial agents of different configurations will be useful as additives in paints, coatings and other compositions for deterring, preventing, or treating microbial infestations. In particular, it is contemplated that synergistic combinations may be discovered between the aforementioned biocides and the other antimicrobial peptidic agents described herein, particularly having the sequences outlined in SEQ ID Nos. 1-199. Likewise, it is expected that the antimicrobial peptidic agents described herein may have a synergistic effect with biocides other than those involved in the synergism experiments discuss herein. Moreover, it is expected that synergistic combinations of preservatives may be found to be effective against a number of different microorganisms other than those involved in the synergism experiments. Particularly, synergy between antifungal agents for controlling growth of the *Fusarium, Rhizoctonia, Ceratocystis, Pythium, Mycosphaerella, Aspergillus* (e.g., *A. paraciticus*) and *Candida* genera of fungi is expected but is not necessarily limited thereto.

A two-dimensional, checkerboard microdilution technique was used to characterize the interactions between the antimicrobial peptidic additive and each of the biocides. The term "checkerboard" refers to the pattern of microtiter wells formed by multiple dilutions of the two preservatives being tested in concentrations equal to, above and below their respective MIC. Thus, the checkerboard consists of columns in which each well contains the same concentration of preservative A, being diluted by 50% for each increment along the x-axis, and rows in which each well contains the same concentration of preservative B, being diluted by 50% for each increment along the y-axis. FIG. 1 illustrates an exemplary transfer blot onto growth medium graph of a 96-well checkerboard plate testing solutions with various combinations of N2000 and an antimicrobial peptidic agent referenced as "ProteCoat™". In general, ProteCoat™ may refer to a material including one or more of the antimicrobial peptides outlined in the Sequence Listing, specification SEQ ID Nos. 1-199. In the following example, ProteCoat™ specifically refers to an amino acid polymer consisting essentially of 7 amino acids in the sequence of FRLKFHI (SEQ ID No. 40 shows the amino polymer in its inverted form). The microorganism for which growth inhibition is test is *B. atrophaeus*. The amount of growth of the microorganism for a particular solution mixture is proportional to the size of the blot. The absence of a blot indicates 100% growth inhibition.

Column 6 of ProteCoat™ along the x-axis represents solution mixtures having the MIC of ProteCoat™ for *B. atrophaeus*. Columns 1-5 represent solution mixtures in which ProteCoat™ has been diluted by 50% relative to the succeeding column of solutions (i.e., column 5 represents solutions in which ProteCoat™ has been diluted by 50% relative to the solutions represented by column 6, column 4 represents solutions in which ProteCoat™ has been diluted by 50% relative to the solutions represented by column 5, etc). Similarly, Row A of N2000 along the y-axis represents solution mixtures having the MIC of N2000 for *B. atrophaeus*. Rows B-E represent solution mixtures in which N2000 has been diluted by 50% relative to the succeeding row of solutions (i.e., row B represents solutions in which N2000 has been diluted by 50% relative to the solutions represented by row A, row C represents solutions in which N2000 has been diluted by 50% relative to the solutions represented by row B, etc.).

As expected, solution mixtures of row A and column 6 exhibit 100% growth inhibition (which is denoted by the absence of a blot in such regions of the graph) since such solutions include a MIC of at least of one of the preservatives. Assuming the preservatives function in at least an additive manner with respect to their biocide activity, 100% growth inhibition is also expected for a solution having 0.5 MIC of each of the preservatives. FIG. 1 corroborates such an assumption at the well of column 5, row B by the absence of a blot. FIG. 1 further illustrates that synergism of biocidal activity exists among the preservatives. In particular, there is 100% growth inhibition exhibited at the well of column 4, row B and, further, the well of column 5, row C exhibits significantly lower growth relative to other wells of the transfer blot graph. Upon further investigation, it was found that there is approximately 3.5-4 fold increase in efficacy of both N2000 and ProteCoat™ for killing/preventing biocidal growth when combined in a solution.

Figure 2:
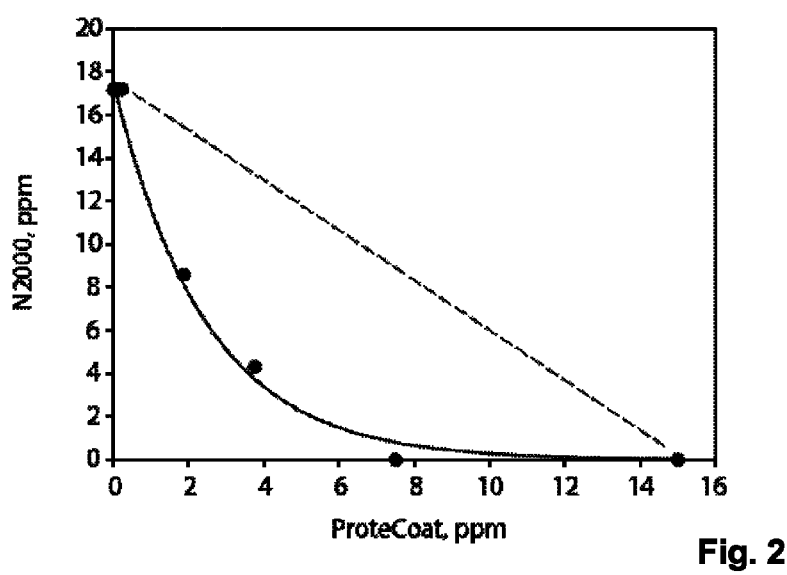
FIG. 2 illustrates an exemplary isobologram of antimicrobial activity of two antimicrobial agents within testing solutions.

The synergistic activity of ProteCoat™ and N2000 is depicted in an isobologram in FIG. 2, allowing for comparison of non-synergistic activity (i.e., additive activity). The solid circles in FIG. 2 indicate values of ProteCoat™ and N2000 needed within a solution to exhibit 100% growth inhibition. The solid line in FIG. 2 represents the best fit line ($R^2$=0.978) of those value points. The dotted line in FIG. 2 indicates the values of ProteCoat™ and N2000 expected to be required in a solution, assuming the preservatives function in an additive manner. As shown in FIG. 2, the actual values of ProteCoat™ and N2000 needed within a solution to exhibit 100% growth inhibition is far less than expected, emphasizing synergistic activity among the preservatives.

Sample results of the aforementioned experiment with regard to *B. atrophaeus* and similar studies with *F. oxysporum* are summarized in Table 4. In Table 4, the columns with the headings ProteCoat™ and N2000 include data reflecting growth inhibition percentages of solutions having each respective preservative alone (i.e., the preservatives are not combined in solution for such data). The percent growth inhibitions were determined experimentally. The columns further indicate the concentrations of N2000 and ProteCoat™ in the solutions (concentrations in parenthesis, in ppm). The column with the heading, Ee, represents the expected percent growth inhibition for a solution having a combination of ProteCoat™ and N2000 at the concentrations noted in the preceding columns, specifically when a "non-synergistic" or additive biocidal effect is assumed. The values in the column with the heading Ee were calculated using an equation derived from the dotted line in FIG. 2. The observed/measured percent growth inhibition for each combination ProteCoat™ and N2000 is provided in the column with the heading Eo. The final column in Table 4, labeled Eo/Ee, is the observed to expected ratio. In accordance with the selected 50% dilution rate of the aforementioned checkerboard microdilution experiment discussed in reference to FIG. 1, any ratio greater than 1.5 indicates synergism among the preservatives. As known to those skilled in the art, higher or lower ratios may be considered when larger or smaller dilutions are employed to evaluate biocide combinations. The results shown in Table 4 clearly demonstrate that very low concentrations of ProteCoat™ can significantly increase the efficacy of a conventional biocide against spore-forms of microbes.

TABLE 4

| Microorganisms | ProteCoat[a] | n2000[a] | $E_e$[b] | $E_o$[c] | $E_o/E_e$[d] |
|---|---|---|---|---|---|
| B. atrophaeus | 0% (0.47) | 55% (8.75) | 55% | 75.6% | 1.37 |
| | 0% (0.93) | 55% (8.75) | 55% | 94% | 1.70 |
| | 0% (1.87) | 55% (8.75) | 55% | 100% | 1.88 |
| F. oxysporum | 15% (0.45) | 21% (1.1) | 33% | 55% | 1.64 |
| | 44% (0.9) | 21% (1.1) | 56% | 92% | 1.63 |
| | 44% (0.9) | 0% (0.54) | 44% | 80% | 1.80 |

[a]Percent inhibition of growth at the biocide concentration indicated in parenthesis (ppm)
[b]$E_e$ is the expected effect (percent inhibition) for an additive, non-synergistic effect
[c]$E_o$ is the observed percent inhibition of growth by the combination of peptide and biocide as listed in columns two and three
[d]$E_o/E_e$ >1.5 indicates synergism As shown in Table 4, several combinations of ProteCoat™ and N2000 may be used to make a synergistic solution. Using the aforementioned methods, concentrations of preservatives within a solution may be "tunable" to exhibit a particular level of growth inhibition. Such ability may allow antimicrobial solutions to be fabricated for particular contamination scenarios and/or optimize the concentrations of component biocides therein. In particular, the antimicrobial peptidic agents described herein may be combined with preservatives of different configurations such that the concentrations of the preservatives of different configurations may be reduced. Such a scenario may be particularly advantageous in embodiments in which one or more of the preservatives are toxic, although the scenario may be equally applicable for embodiments in which one or more of the preservatives are non-toxic. In addition or alternatively, the antimicrobial peptidic agents described herein may be combined with preservatives of different configurations such that the biocidal efficacy of the preservatives is increased.

It is contemplated that any previously described formulation of a microbial-prone composition may be modified to incorporate an antimicrobial peptidic agent. Examples of described coating compositions include industrial water-borne coating formulations (e.g., air dry coatings, air dry or force air dry coatings, anti-skid of non-slip coatings, bake dry coatings, clear coatings, coil coatings, concrete coatings, dipping enamels, lacquers, primers, protective coatings, spray enamels, traffic and airfield coatings), architectural water-borne coating formulations (e.g., exterior paints, exterior enamels, exterior coatings, interior paints, interior enamels, interior coatings, exterior/interior paints, exterior/interior enamels, exterior/interior primers, exterior/interior stains), solvent borne coating formulations (e.g., exterior paints, exterior enamels, exterior coatings, exterior sealers, exterior fillers, exterior primers, interior paints, interior enamels, interior coatings, interior primers, exterior/interior paints, exterior/interior enamels, exterior/interior coatings, exterior/interior varnishes); and prepaint specialties and/or surface tolerant coatings (e.g., fillers, sealers, rust preventives, galvanizers, caulks, grouts, glazes, phosphatizers, corrosion inhibitors, neutralizers, graffiti removers, floor surfacers).

An exemplary exterior gloss alkyd house paint that includes an antimicrobial peptidic agent is outlined in Table 5.

TABLE 5

COMPOSITION OF AN EXEMPLARY EXTERIOR GLOSS ALKYD HOUSE PAINT

| Component | Weight or Volume |
|---|---|
| Grind: | |
| first alkyd | 232.02 lb or 29.9 gallons |
| second alkyd | 154.2 lb or 20 gallons |
| aliphatic solvent: duodecane | 69.55 lb or 1.7 gallons |
| lecithin | 7.8 lb or 0.91 gallons |
| $TiO_2$ | 185.25 lb or 5.43 gallons |
| 10 micron silica | 59.59 lb or 2.7 gallons |
| bentonite clay | 18.00 lb or 1.44 gallons |
| second alkyd | 97.22 lb or 12.61 gallons |
| first alkyd | 69.84 lb or 9.00 gallons |
| antimicrobial peptidic agent - optionally, in combination with a conventional mildewcide | effective amount/up to 7.8 lb or 0.82 gallons |
| Letdown: | |
| aliphatic solvent: dudecane) | 19.50 lb or 3.00 gallons |
| first drier: 12% solution cobalt) | 2.00 lb or 0.23 gallons |
| second drier: 18% solution Zr) | 2.92 lb or 0.32 gallons |
| third drier: 10% solution Ca) | 8.00 lb or 0.98 gallons |
| Anti skinning agent: methyl ethyl ketoxime | |
| Aliphatic solvent | 3.22 lb or 0.42 gallons |
| | 9.75 lb or 1.50 gallons |

An exemplary exterior flat latex house paint including an antimicrobial peptidic agent is outlined in Table 6 with the components listed in typical order of addition.

TABLE 6

COMPOSITION OF AN EXEMPLARY EXTERIOR FLAT LATEX HOUSE PAINT

| Component | Weight or Volume |
|---|---|
| water | 244.5 lb or 29.47 gallons |
| hydroxyethylcellulose | 3 lb or 0.34 gallons |
| glycols | 60 lb or 6.72 gallons |
| polyacrylate dispersant | 6.8 lb or 0.69 gallons |
| Antifungal Peptidic Agent | effective amount up to |
| optionally, other biocide(s) | 10 lb or 1 gallons |
| non-ionic surfactant | 1 lb or 0.11 gallons |
| titanium dioxide | 225 lb or 6.75 gallons |
| silicate mineral | 160 lb or 7.38 gallons |
| calcined clay | 50 lb or 2.28 gallons |
| acrylic latex, @ 60% | 302.9 lb or 34.42 gallons |
| coalescent | 9.3 lb or 1.17 gallons |
| defoamers | 2 lb or 0.26 gallons |
| ammonium hydroxide | 2.2 lb or 0.29 gallons |
| 2.5% HEC solution | 76 lb or 9.12 gallons |
| antifungal peptidic agent | 1.8 lb or 0.82 gallons |

From these representative formulations, it will be readily appreciated that a wide variety of paints and other coating compositions may be improved by addition of an antimicrobial peptidic agent. Some of these include industrial water-borne coating formulations (e.g., air dry coatings, air dry or force air dry coatings, anti-skid of non-slip coatings, bake dry coatings, clear coatings, coil coatings, concrete coatings, dipping enamels, lacquers, primers, protective coatings, spray enamels, traffic and airfield coatings); architectural water-borne coating formulations (e.g., exterior paints, exterior enamels, exterior coatings, interior paints, interior enamels, interior coatings, exterior/interior paints, exterior/interior enamels, exterior/interior primers, and exterior/interior stains); solvent borne coating formulations (e.g., exterior paints, exterior enamels, exterior coatings, exterior sealers, exterior fillers, exterior primers, interior paints, interior enamels, interior coatings, interior primers, exterior/interior paints, exterior/interior enamels, exterior/interior coatings, and exterior/interior varnishes); and prepaint specialties and/or surface tolerant coatings (e.g., fillers, sealers, rust preventives, galvanizers, caulks, grouts, glazes, phosphatizers, corrosion inhibitors, neutralizers, graffiti removers and floor surfacers).

An antimicrobial paint or coating containing an antimicrobial peptidic agent may then be tested and used as described elsewhere herein, or the product may be employed for any other suitable purpose as would be recognized by one of skill in the art in light of this disclosure. For instance, the physical properties (e.g., purity, density, solubility, volume solids and/or specific gravity, rheology, viscometry, and particle size) of the resulting antimicrobial liquid paint or other coating product, can be assessed using standard techniques that are known in the art.

As mentioned in the background discussion, the quality of a liquid coating mixture may suffer markedly if microorganisms degrade one or more of the components during storage. Since many of the coating products in use today contain ingredients that make it susceptible or prone to microbial infestation and growth, it is common practice to include a preservative. Although bacterial contamination may be a contributing factor, fungi are typically a primary cause of deterioration of a liquid paint or coating. Foul odor, discoloration, thinning and clumping of the product, and other signs of deterioration of components render the product commercially unattractive and/or unsatisfactory for the intended purpose. If the container will be opened and closed a number of times after its initial use, in some instances over a period of several months or years, it will inevitably be inoculated with ambient fungus organisms or spores subsequent to purchase by the consumer.

To avoid spoilage, it is especially desirable to ensure that the product will remain stable and usable for the foreseeable duration of storage and use by enhancing the long-term antifungal properties of the paint or coating with an antimicrobial peptide agent. The in-can stability and prospective shelf life of a paint or coating mixture containing an above-described antimicrobial peptide agent may be assessed using any appropriate testing method as would be known to one of skill in the art using conventional microbiological techniques. A fungus known to infect paints or other coatings is preferably employed as the test organism.

A suitable assay protocol for evaluating coatings containing an antimicrobial peptide is outlined below.

(a) A set of four 1×10 cm aluminum coupons approximately 1/32 in thick are prepared as follows: (1) blank A1 coupon; (2) A1 coupon coated with an aqueous solution of a peptide produced and identified as described in the preceding examples, and allowed to dry; (3) A1 coupon coated on both sides with a base paint composition, allowed to dry, and then the paint film is coated with a like amount of the same test peptide solution as applied to coupon 2; and (4) A1 coupon painted with a paint mixture containing the same base paint composition as for coupon 3 and a like amount of the peptide, as for coupons 2 and 3. Preferably duplicate or triplicate sets of these specimens are prepared. Optionally, a conventional biocide may be included as a positive control. The base paint composition may be any suitable water-based latex paint, with or without biocides, which is available from a number of commercial suppliers.

(b) Each of the specimens from (a) is placed on a bed of nutrient agar and uniformly innoculated with a microbial suspension. A preferred fungal test organism is *Fusarium oxysporum*. The microbial suspension may be applied by atomizer or by pipet, however a thin layer of nutrient agar mixed with the fungal innoculum is preferred.

(c) The specimens are incubated at about 28° C. under 85 to 90% relative humidity for 4 weeks.

(d) Microbial growth on each specimen is preferably rated weekly as follows: None=0; traces of growth (<10% coverage)=1; light growth (10-30%)=2; moderate growth (30-60%)=3; and heavy growth (60% to complete coverage)=4.

Another suitable assay protocol for testing the antimicrobial properties of a coating or paint film containing an antimicrobial peptide is described below.

(a) Preparation of the Coated Surface. Duplicate or triplicate sets of approximately ½ in. thick, 3×4 in. untreated wooden or gypsum board panels are prepared as follows: (1) blank panel; (2) coated with an aqueous solution of a peptide produced and identified as described in the preceding examples, and allowed to dry; (3) coated on both sides with a base paint composition, allowed to dry, and then the paint film is coated with a like amount of the same test peptide solution as applied to panel 2; and (4) painted with a paint mixture containing the same base paint composition as for panel 3 and a like amount of the peptide, as for panels 2 and 3. Optionally, a conventional biocide may be included as a positive control.

(b) Contamination. The panels are randomly arranged and suspended in an environmental cabinet above moist soil that has been inoculated with the desired microbe, (e.g., *Fusarium oxysporum*). Enough free space is provided to allow free circulation of air and avoid contact between the panels and the walls of the cabinet.

(c) Incubation. The panels are incubated for two weeks at 30.5-33.5° C. and 95-98% humidity.

(d) Scoring. A set of panels (test, control, and, optionally, a positive control) are removed for analysis at intervals, preferably weekly. The microbial growth on the specimen panels is rated as described above.

Alternatively, one or more equivalent testing protocols may be employed, and field tests of coating compositions containing laboratory-identified antimicrobial peptides or candidate peptides may be carried out in accordance with conventional methods as would be known to those of skill in the art.

Both the interior latex (e.g., Olympic Premium, flat, ultra white, 72001) and acrylic paints (e.g., Sherwin Williams DTM, primer/finish, white, B66W1; 136-1500) appeared to be toxic to both *Fusarium* and *Aspergillus*. Therefore, eight individual wells (48-well microtito plate) of each paint type were extracted on a daily basis with 1 ml of phosphate buffer for 5 days (1-4 & 6) and then allowed the plates were allowed to dry before running the assay. Each well contained 16 ul of respective paint.

Extract Testing:

The extract from two wells each of the two paints for each day was tested for toxicity by mixing the extract 1:1 with 2× medium and inoculating with spores (10E4) of *Aspergillus* or *Fusarium*. The extracts had no affect on growth of either test fungus.

Well Testing:

The extracted and non-extracted wells for each of the paints were tested with a range of inoculum levels in growth medium using the two different fungi. For *Fusarium* the range was 10E1-10E4 and for *Aspergillus* 10E2-10E5.

Well Testing of Acrylic Paint Plates:

Both *Fusarium* and *Aspergillus* grew in all extracted wells at all inoculum levels. Only *Aspergillus* grew in non-extracted wells at the 10E5 level and not at lower levels indicative of an inherent biocidal capability.

Well Testing of Latex Paint Plates:

Fusarium grew in the extracted wells only at the 10E4 inoculum level but not at 10E1-10E3. Aspergillus grew in all extracted wells showing an inoculum level effect. No growth was observed for either Fusarium or Aspergillus in non-extracted wells.

Conclusion:

Extraction of the toxic factor(s) found in both paints was possible. However, it appeared that it may be less extractable from the latex paint.

Evaluation of Peptide Activity in Presence of Acrylic and Latex Paints

It was established that it was possible to extract both acrylic and latex paints dried in a 48-well format to make them non-toxic to the test microorganisms—Fusarium and Aspergillus. Using that information an experiment was designed to determine the effect the paint has on peptide activity against two test organisms.

Experimental Design:

1. Coat 48-well plastic plates with 16 µl of acrylic or latex paint. Dry for two days under hood.
2. Extract designated wells with 1-ml phosphate buffer changing the buffer on a daily basis for 7 days. Control wells were not extracted to confirm paint toxicity.
3. Add 20 µl of peptide series in duplicate to designated dry paint coated wells. Peptide, SEQ ID No. 41, series was added in a two-fold dilution series to wells and allowed to dry. The concentration of peptide added ranged from 200 µg/20 µl to 1.5 µg/20 µl.

Inoculated Paint-Coated Plates as Follows:

1. Extracted control wells received 180 µl of medium+20 µl of spore suspension ($10^4$ spores/20 µl of medium). Inoculum was either Fusarium or Aspergillus in each case.
2. Non-extracted control wells received 180 µl of medium+20 µl of spore suspension ($10^4$ spores/20 µl of medium).
3. Extract wells with dried peptide series received 180 µl of medium+20 µl of spore suspension ($10^4$ spores/20 µl of medium). In duplicate.
4. Extract wells that did not have dried peptide series received 160 µl of medium+20 µl of spore suspension ($10^4$/20 µl of medium)+20 µl peptide series as above. In duplicate.

Plates were observed for growth over a 5-day period.

Growth and Peptide Controls:

1. Use sterile non-paint coated 48 well plastic plates.
2. Growth control wells for each test fungus received 180 µl of medium+20 µl of spore suspension ($10^4$ spores/20 µl of medium).
3. Peptide activity controls received 160 µl of medium+20 µl of spore suspension ($10^4$ spores/20 µl of medium)+20 µl peptide series as above. Peptide series were added in a two-fold dilution series to wells and range from 200 µg/20 µl to 1.5 µg/20 µl. Therefore, the range of peptide tested was 200 µg/200 µl or 1.0 µg/µl (1000 µg/ml) to 0.0075 µg/µl (7.5 µg/ml).
4. Uninoculated medium served as blank for absorbance readings taken at 24, 48, 72, 96 and 120 hours.

Results:

Unextracted wells containing either latex or acrylic paint inhibited growth of both Fusarium and Aspergillus. Extracted wells containing either latex or acrylic paint allowed growth of both Fusarium and Aspergillus.

The calculated MIC for Fusarium in peptide activity control experiments was 15.62 µg/ml. For Aspergillus, the calculated MIC was 61.4 µg/ml.

For extracted acrylic-coated plates, the following results were obtained.

Controls as stated in above.

For Fusarium with dried peptide, inhibition was seen at 1000 and 500 µg/ml after 5 days. Spores exposed to liquid peptide added to dry paint wells were inhibited at 1000, 500 and 250 µg/ml after 4 days, and 1000 and 500 µg/ml after 5 days.

For Aspergillus with dried peptide, inhibition was seen at 1000 µg/ml after 5 days. Spores exposed to liquid peptide added to dry paint wells were inhibited at 1000 and 500 µg/ml after 5 days.

For extracted latex-coated plates the following results were obtained.

Controls as stated above.

For Fusarium with dried peptide, inhibition was seen at 1000 µg/ml after 5 days. Spores exposed to liquid peptide added to dry paint wells were inhibited at 1000 µg/ml after 5 days.

For Aspergillus with dried peptide, inhibition was seen at 1000 µg/ml after 5 days. Spores exposed to liquid peptide added to dry paint wells were inhibited at 1000 µg/ml after 5 days.

Conventional techniques for applying or transferring a coating material to a surface are well known in the art and are suitable for applying the antimicrobial peptide composition. The selected peptides have activity for inhibiting or preventing the growth of one or more target microbes. An exemplary manner to inhibit or prevent microbial infestation and growth involves dissolving or suspending one or more antimicrobial peptidic agents from the Sequence Listing, preferably approximately 250-1000 mg/L of the hexapeptide of SEQ ID No. 41, in solution (e.g., water) and simply brushing or spraying the solution onto a pre-painted surface such as an exterior wall that is susceptible to mold infestation. The applied peptide solution is then dried on the painted surface, preferably by allowing it to dry under ambient conditions. If desired, drying can be facilitated with a stream of warm, dry air. Optionally, the application procedure may be repeated one or more times to increase the amount of antimicrobial peptide that is deposited per unit area of the surface. As a result of the treatment, when the treated surface is subsequently subjected to the target microbe organisms or spores and growth promoting conditions comprising humidity above about typical indoor ambient humidity, presence of nutrients, and temperature above about typical indoor ambient temperature and not exceeding about 38° C., the ability of the surface to resist microbial infestation and growth is enhanced compared to its pre-painted condition before application of the antimicrobial peptide.

A simple spray-coated surface may not provide sufficient durability for certain applications such as surfaces that are exposed to weathering. Longer-term protection may be provided against adhesion and growth of microbes by mixing one or more of the antimicrobial peptides with a base paint or other coating composition, which may be any suitable, commercially available product well known in the art. Preferably, the base composition is free of chemicals and other additives that are toxic to humans or animals, and/or that fail to comply with applicable environmental safety rules or guidelines. The typical components, additives and properties of conventional paints and coating materials, and film-forming techniques, are well known in the art and are also described in U.S. patent application Ser. No. 10/655,345 filed Sep. 4, 2003 and U.S. patent Ser. No. 10/792,516 filed Mar. 3, 2004, which is hereby incorporated herein by reference.

If additional, long-term protection against growth and adhesion of microbes is desired, the paint or other coating composition may include a barrier material that resists moisture penetration and also prevents or deters penetration and adhesion of the microorganisms and the airborne contaminants which serve as food for the growing organisms. Some typical water repellent components are acrylic, siliconates, metal-stearates, silanes, siloxane and paraffinic waxes. The user will preferably take additional steps to deter micrpbe infestation include avoiding moisture from water damage, excessive humidity, water leaks, condensation, water infiltration and flooding, and taking reasonable steps to avoid buildup of organic matter on the treated surface.

Although it is preferred that in situations where existing microbial growth is present, the microbe colonies and spores are first removed or substantially eliminated before application of one of the present antimicrobial coatings, it is expected that in some situations an antimicrobial compositions will be applied to existing microbe infected surfaces. In this case, the composition, containing one or more antimicrobial peptides, may inhibit, arrest the growth of, or substantially eradicate the microbes. Early detection and treatment is highly preferred in order to minimize the associated discoloration or other deterioration of the underlying surface due to microbe growth. The treatment procedure may consist of simply applying one or more coats of an antimicrobial peptide solution, paint or other coating composition.

Porous or semi-porous objects or materials such as paper, fabrics, carpet, some types of stone, and many other items that are employed indoors or outdoors, have internal surface areas that can be susceptible to infestation by mold and are very difficult to treat effectively by conventional methods. It is within the scope of the coatings described herein to impregnate such porous objects with an antimicrobial peptidic agent, as described above. The liquidity of the composition is such that it is capable of penetrating into the pores of the object. In this way, an effective amount of the antimicrobial peptidic agent is deposited on the internal surfaces as well as the exterior ones. Circumstances requiring treatment of a porous surface may benefit from using a relatively thin coating material rather than a thick, pigmented paint, in order to facilitate penetration of the pores.

The interior walls of grain silos or other fruit or grain storage or transportation tanks may be coated with a composition containing an antimicrobial peptidic agent to deter the attachment and growth of microbe organisms inside the container. By selecting antimicrobial peptides that target specific organisms and are non-toxic to humans or animals, microbe contamination of a wide variety of agricultural products may be deterred.

Over the past decade, outbreaks of food poisoning and hospital-acquired infections by so-called "super bugs" have become increasingly frequent. These are strains of bacteria that are resistant to conventional antibiotics, such as Methicillin-resistant *Staphylococcus aureus* (MRSA) and Vero-cytotoxin producing variants of *Escherichia coli*. Worldwide public concern about hygienic surfaces have also been heightened today due to the emergence and spread of new viral infections such as SARS. The current proliferation of antimicrobial cleaners, utensils, food preparation surfaces and coating systems aimed at fulfilling the demands of an increasingly hygiene conscious public are a testament to those widespread concerns.

Some of the antimicrobial peptides described herein, particularly the 8-10 amino acid residue long peptides also have the property of inhibiting the growth of bacteria, including disease-causing bacteria such as *Staphalococcus* and *Streptococcus*. Thus, peptides with sequenes such as SEQ ID Nos. 41, 197, 198, and 199 can inhibit growth of *E. amylovora, E. carotovora, E. coli, R. solanocerum, S. aureus*, and *S. faecalis* in standard media at IC50's of between 10-1100 mg/ml and MIC's of between 20-1700 mg/ml. *Staphalococcus* and *Streptococcus* bacteria are of special concern in hospital environments where antibiotic resistance is increasingly common. A multipurpose paint or coating is prepared by combining one or more antimicrobial peptides with one or more antibacterial peptides and, in some embodiments, with one or more antiviral peptides. Alternatively, a peptide is selected with more than one of antifungal, antibacterial, and antiviral properties. Paints and other coatings containing the antifungal/antibacterial/antiviral peptides will be applied to surfaces to lend antifungal, anti-bacterial and/or antiviral properties to those surfaces. It is expected that the use of these and other antifungal/antibacterial/antiviral peptidic agents will avoid the problem of human toxicity that is associated with conventional biocidal compounds in today's paints and coatings. The advantage of combined antifungal, antibacterial and/or antiviral activity will find particular usefulness in hospital environments and other health care settings.

Beyond the concerns about food poisoning and hospital acquired infections by antibiotic-resistant "super bugs," and worries about SARS-like outbreaks, there is also a need to prevent or protect against the possibility of contamination of public facilities and surfaces by toxic chemicals due to accidental spills, improper application of certain insecticides, or as a result of deliberate criminal or terroristic acts. In particular, organophosphorus compounds ("organophosphate compounds" or "OP compounds") and organosulfur ("OS") compounds, which are used extensively as insecticides, are highly toxic to many organisms, including humans. OP compounds function as nerve agents, and some of the most toxic OP compounds are known to have been used as chemical warfare agents. As discussed in more detail in copending U.S. patent application Ser. No. 10/655,435 filed Sep. 4, 2003, some OP chemical warfare agents can be taken up through skin contact and can remain on material, equipment and terrain for long periods of time (e.g., weeks). By addition of a thickener (e.g., a variety of carbon polymers), even volatile OP agents may be rendered less volatile and more persistent on a contaminated surface.

Thus, it can be readily appreciated that in some situations a multifunctional surface treatment that combines antifungal properties with the ability to degrade organophosphorus compounds would be desirable. Such composition may be in the form of a coating, a paint, a non-film forming coating, an elastomer, an adhesive, an sealant, a material applied to a textile, or a wax, and may be modified by addition of one or more antifungal peptide selected as described in Examples 1-6 and an organophosphorus compound detoxifying agent such as an OP degrading enzyme or cellular material containing such activity. Suitable OP degrading agents are described in copending U.S. patent application Ser. No. 10/655,435 filed Sep. 4, 2003 and U.S. patent application Ser. No. 10/792, 516 filed Mar. 3, 2004 and hereby incorporated herein by reference.

The antimicrobial additives described above are expected to be additionally useful for coating or mixing into sealants and elastomers such as grouts and caulks, especially those that are in frequent contact with, or constantly exposed to microbial nutrients and/or moisture. Examples of adhesives and sealants include but are not limited to caulks, acrylics, elastomers, phenolic resin, epoxy, polyurethane, anaerobic and structural acrylic, high-temperature polymers, water-based industrial type adhesives, water-based paper and packaging adhesives, water-based coatings, hot melt adhesives, hot melt coatings for paper and plastic, epoxy adhesives, plastisol compounds, construction adhesives, flocking adhesives, industrial adhesives, general purpose adhesives, pressure sensitive adhesives, sealants, mastics, urethanes. Such adhesives and sealants may be applied to various surfaces (e.g., metal, plastic, textile, paper). An adhesive, sealant or elastomer composition containing one or more conventional antimicrobial substance may be modified by addition of one or more of the antimicrobial peptidic agents described herein.

An antimicrobial peptidic agent may also be incorporated into a material applied to a textile, such as, for example, a textile finish (e.g., soil-resistant finishes, stain-resistant finishes). One type of water repellent and/or oil repellent textile finish is Scotchguard™ (available from 3M Company of Maplewood, Minn., U.S.A.). A textile finish may be modified by addition of one or more of the antimicrobial peptidic agents described herein.

Conjugation of a peptide to a polymer carrier molecule or insoluble substrate is described for stabilizing antimicrobial activity in a paint film or coating. That capability may also be used to advantage by chemically linking or otherwise associating one or more antimicrobial peptides to a polymeric material or plastic fabric which would otherwise be more susceptible to infestation, defacement or deterioration by microbes. Conventional techniques for linking the N- or C-terminus of a peptide to a long-chain polymer may be employed. The antimicrobial peptide may include additional amino acids on the linking end to facilitate linkage to the PVC polymer. A PVC-membrane such as a flexible or retractable roof or covering for an outdoor stadium, is treated to chemically link antimicrobial peptides to at least a portion of the outer surface of the membrane prior to its installation. Where an installed polymer membrane covering is already infested by microbes, and it is not practical for it to be removed and replaced by an antimicrobial peptide-linked polymer membrane, it may be feasible to clean the existing infestation or discoloration, and then apply or bond a suitable antimicrobial coating containing a stabilized antimicrobial peptidic agent. PVC is only one of many well-known types of plastic or polymer-containing materials that could be linked to an antimicrobial peptide in this manner.

For ease of production, in most instances paint or coating product containing antimicrobial peptidic agents will be provided to the consumer as a single premixed formulation. Alternatively, in order to optimize the initial activity and extend the useful lifetime of the coating, the antimicrobial peptidic agent may instead be packaged separately from the paint or coating product into which the antimicrobial agent is to be added. For increased stability, the peptidic agent may also contain a suitable solid or liquid carrier. As in preceding examples, the antimicrobial peptidic agent may comprise one or more "pure" antimicrobial peptides of defined sequence, or it may include a peptide library aliquot containing a mixture of peptides in which at least two (and preferably three or four) of the N-terminal amino acid residues are known (as in SEQ ID Nos. 1-24). If the peptidic agent is a mixture of peptides, at least one will have antimicrobial activity.

In some situations it may also be preferred to store a microbial-prone material in a separate container ("pot") prior to application, in order to minimize the occurrence of microbial contamination prior to use and for other reasons. Separation of conventional coating components is typically done to reduce film formation during storage for certain types of coatings. Accordingly, some or all of the different components of the antimicrobial composition are stored in a plurality of containers, or as a multi-pack kit, and the components are admixed prior to and/or during application. For example, 0.001% to 100%, including all intermediate ranges and combinations thereof, of the antimicrobial peptidic agent may be stored in a separate container from one or more microbial-prone materials of the final composition. A multi-pack kit may include one or more pots of a microbial-prone material, preferably including 2- to 5-packs of microbial-prone material. A new antimicrobial composition may be prepared at or near the time of use by combining a microbial-prone material (e.g., carbon polymer-containing binder) with other coating components, including an antimicrobial peptide, polypeptide or protein, as described herein.

A novel concept described herein includes the use of peptides as antimicrobial biopesticides. As a biologically inspired antimicrobial, peptides have the potential to combine the environmentally friendly nature of the biopesticides with the fast-acting and broad-spectrum nature of the more traditional chemical pesticides. Consequently, a new generation of antimicrobial additives for coatings has been developed. The additives are efficacious biocides for coatings in processing, in the can and in the film. They can be used alone or synergistically in combination with existing biocides to effectively kill fungi, bacteria and viruses, including the spore stages of such microorganisms. In general, the objectives of the development of the antimicrobial peptides described herein is to retain their biocidal activity in coatings; to identify peptides that could be relatively economically manufactured; to modify them as necessary to address the realities of the coating environment; to develop techniques that would allow rapid-throughput testing; and to test the additives in a variety of coatings and against a variety of target microorganisms in the development of additive solution.

Since toxicity to humans, as evaluated by lysis of red blood cells, appears to be influenced by both length of peptide and the strength of hydrophobic interactions, the design template of the target peptides was only six residues. This adds further economic advantage, as the process of combinatorial synthesis followed by screening and selection could be limited to five iterations. The mechanism of action of these peptides appears to be typical of most antimicrobial peptidic agents. They exhibit the common cationic, hydrophobic character, with the cationic nature of the hexameric peptide being conferred by the presence of the positively charged amino acids arginine (R), lysine (K) and/or histidine (H). The hydrophobic residues phenylalanine (F) and leucine (L) that separate the positively charged residues of the peptide enhances the capabilities of the charged residues to interact with the hydrophobic chains of the phospholipids. Although the actual mechanism of killing is not known, the hexameric peptide FRLKFH appears to compromise the integrity of both the cell membrane and the internal nuclear membrane surrounding the DNA. Observations indicate that all antimicrobial peptidic agents used in these studies are able to compromise exposed cellular membranes within 5 minutes, to cause rapid kill of spores and vegetative cells used to challenge the coated surfaces.

In the past, the only way to obtain these small cationic peptides were to isolate them from the host organism, which required large amounts of material and yielded only very small amounts of peptide, or to synthesize them by chemical methods. One alternative available now is to use biological production processes to generate the peptides. Fermentation methods will certainly be most economical. Antimicrobial peptidic agents have been successfully expressed using several genetic/biological approaches, including production as fusion proteins, inclusion bodies, repeats/multimers, or cell-surface expression. The advantages of producing these peptides in a bioexpression system include: (1) the relative ease with which the system can be scaled up: (2) cost effectiveness, and (3) the ability to make variants and utilize optimized isolation procedures. By developing and producing active peptides in the form found in nature, the peptides can be manufactured using existing fermentation technology, reducing production costs to acceptable commercial levels.

This large-scale chemical production of peptides can be achieved in a number of ways: solid-phase synthesis or solution-phase synthesis. Where manufacturing of research (gram) quantities of an antimicrobial peptide would be cost prohibitive, commercially feasible manufacturing of kilogram quantities of antimicrobial peptides is imminently achievable. While the actual sequence, length and any modifications present in the peptide will have dramatic effects on production costs, optimized synthetic processes will further dramatically reduce costs for large-scale peptide synthesis.

In order to evaluate the concept of antimicrobial peptides as a biocidal coating component, the hexapeptide described above from the preliminary studies underwent further design considerations, resulting in a heptapeptide, antimicrobial peptidic agent-7, of similar composition and activity. To evaluate the efficacy of the antimicrobial additives described herein when added to coatings, a dilution series of the antimicrobial additives was added to UCAR 451 (a clear styrene-acrylic latex available from Dow Chemical Company). An antimicrobial additive was dissolved in UCAR 451 and the resulting coating was applied to the bottom of 96-well clear polystyrene plates, and then challenged with an inoculum of $10^4$ spores/ml of *Fusarium oxysporum* f. sp. lycopersici. The spores were subsequently transferred to a growth media, and allowed to grow for about 48 hrs at approximately 25° C. As expected, the MIC of the admixed coating was greater than that of the peptide ingredient in broth, with the pattern of growth inhibition in the coating determined the MIC to be 1.17 mg/ml. There was clear retardation of growth even at the lowest peptide concentration tested, which was 0.78 mg/ml, at the 24 hr time point (although in the presence of this high of a spore challenge, by 48 hrs this antimicrobial additive concentration was overwhelmed and the inhibition was ultimately less than 10%). In addition to antimicrobial agent design, there are a number of approaches that can be used to engineer specialty coatings for antimicrobial applications. In particular, appropriate additives may be blended with coatings for in-can stabilization, post-added as synergistic activity modifiers just prior to application or applied to existing surfaces as synergistic clear coat sealer surfaces. The high temperature latex polymer (i.e., UCAR451) discussed above was chosen to validate activity in a very rigid polymer system. The rationale was that the free volume between individual polymer chains varies depending upon the respective temperature, pigment to binder ratio, and use temperatures to name a few. Glass transition temperatures dictate the shift from glassy to rubbery when a polymer is heated from below to above that range of temperatures. Hence, the mobility of any ingredient or component added to the polymeric system, such as the antimicrobial peptidic additive described herein, is related to the polymer temperature. An emulsion polymer with a transition temperature of 45° C. provides a worst-case scenario regarding mobility and activity with all other variables remaining constant, yet the antimicrobial peptidic agents described herein are effective biocides when blended with this polymer.

The application of the antimicrobial additive described herein to existing surfaces as a clear coat sealer or top coat is simulated in the current studies by coating a surface (in this case, the bottom of each well in a 96-well plate) with UCAR451, allowing that to dry, then applying a layer of the antimicrobial additive. These results show that substantial increases in the killing efficacy of antimicrobial peptidic agents described herein can be achieved by localizing the additive in the paint film at the interface challenged by the microorganism. Thus, if used as coatings on previously contaminated surfaces, one may choose to localize the additive in greatest concentrations at the surface-film interface. Conversely, if the spore challenge occurs after the curing of the paint film, it will be preferable to localize the greatest concentration of antimicrobial peptidic agents described herein at the exposed film surface. Due to the variable charge nature of the antimicrobial peptidic agents described herein, such localization is easily achieved.

The antimicrobial additives described herein offer substantial advantages over traditional biocidal/biostatic chemicals presently used in coatings. They are biodegradable, work under mild conditions, provide safe alternatives to existing pesticides, and are not associated with the production or release of hazardous compounds to the environment. The antimicrobial additives described herein bring a new technology to bear on the problems of certain existing biocides that are viewed as hazardous to the environment or to humans, offering an opportunity for protection without the adverse human-health and environmental impacts of traditional approaches.

Equally important is the adaptability of antimicrobial peptide-based additives. The diversity of antimicrobial peptides identified in nature provides a variety of design templates for tailoring a new generation of environmentally friendly antimicrobial additives for a wide variety of coatings. Combinatorial libraries of antimicrobial peptides provide a wealth of candidate biocides adaptable to specific coating requirements. With the rapidly increasing database of naturally occurring antimicrobial peptidic agents and the available recombinant DNA technologies, tools exist today that will allow antimicrobial peptidic agent additives to be developed for specific coating applications (e.g. architectural, technical paper, military, homeland security, in-can, in-process, on-surface, etc.).

Since the antimicrobial additives described herein are designed to work alone or synergistically with existing biocides, the use of the additives can be integrated with other biocidal products to enhance their activity. The large number of potential applications for these “green” biocides, including housing, surfaces in hospitals, schools, government facilities, industrial sites, and public transportation systems will expand the types of coatings into which the additives may be used. The development of cost-effective, antimicrobial surfaces will mitigate hazards for building occupants, decrease the time needed for reclamation of contaminated spaces and minimize environmental impacts commonly associated with traditional biocides.

Broad-spectrum antimicrobial additives that offer substantial advantages over the traditional biocidal/biostatic chemicals presently used in coatings are described in more detail below. The additives are biodegradable, work under mild conditions, provide a safe alternative to existing pesticides, and are not associated with the production or release of hazardous compounds into the environment. As such, the additives bring a new and innovative technology to bear on the problem of biocides for coatings, offering protection without the adverse human-health and environmental impact often associated with currently used biocides.

Antimicrobial peptides (antimicrobial peptidic agents) are ubiquitous molecules produced by microorganisms as well as plants, invertebrates and vertebrates. They represent the first line of defense against pathogens in living systems, and interest in them is rapidly expanding since the emergence of resistance to commonly used antibiotics has stimulated the search for new, naturally occurring antimicrobial peptidic agents. The antimicrobial peptidic additives described herein are designed to function in minute quantities, against the vegetative and spore stages of target microorganisms. As with chemical biocides, the mode of action of the additives is designed to be compatible with the components of the coating such that the desired biocidal activity is achieved. In addition, it was considered crucial that the additives not only work alone, but also synergistically with existing biocides and other antimicrobial components of coatings.

In general, it is desirable for the antimicrobial coating additives described herein to exhibit the following properties: 1) selective toxicity to discriminate between target microbial cells and non-target organisms; 2) rapid killing, the time needed for killing should be shorter than the doubling time of the target microorganism; 3) effective against a broad range of microorganisms; and 4) no resistance development, e.g. have a mechanism of action such that the target microbes cannot easily develop resistance. More generally, in order to provide for selective toxicity and broad-spectrum activity, the additives are designed to target those features that are ubiquitous among microbial cells but do not exhibit toxic effects or cytotoxicity to mammalian cells. For rapid killing, the site of action of the additives targets the cell surface rather than the cell interior, and is capable of affecting the target membrane even in the presence of a spore coat or other protective envelope.

The selectivity of the additives described herein is due to a fundamental difference in the membranes of microbes and multicellular animals. Bacterial membranes, which are the best understood of the microbial examples, are organized in such a way that the outer region of the lipid bilayer, the region exposed to the environment, is composed of lipids having negatively charged groups. In contrast, the outward facing side of the membranes of plants and animals is composed primarily of lipids with no net charge. However, despite the diversity in the sequence and structure, all antimicrobial peptidic agents share a common three-dimensional arrangement: they fold into amphiphilic molecules with one hydrophobic face and one charged face. antimicrobial peptidic agent The Shai-Matsuzaki-Huang model explains the mechanism of most antimicrobial peptidic agents as initiating with the peptide-membrane interaction, followed by displacement of lipids and alteration of the membrane structure. Here the consensus ends, however, and a number of models have been proposed for how the antimicrobial peptidic agent alters the microbial membrane [e.g., the barrel-stave model, the carpet model, the toroidal pore model and the micellar aggregate channel model], as well as how the antimicrobial peptidic agent kills [e.g., fatal depolarization of the membrane, micellization or entry of the peptide into the cell and disruption of intracellular targets]. In developing the technology of the additives described herein, and in particular in maximizing the coating scaffolding in which the antimicrobial peptide is expected to work, understanding these mechanisms of action is desirable.

Efficient in-process and in-can biocides should have broad-spectrum antimicrobial efficacy to offer the optimum preservation. Although the selectivity of the antimicrobial peptidic agents can be attributed to the unique characteristics of the cell wall and membranes of microbes, the broad-spectrum nature of antimicrobial peptidic agents lies in their unique ability to target those features that are ubiquitous among microbial cells.

Conceptually, the design of a biocide that is both broad-spectrum and selective can be very challenging because, as the terms imply, these characteristics are to some degree mutually exclusive. One test commonly applied during the development of new antimicrobials to identify undesirable effects that may be associated with the antimicrobial peptidic agent is the red blood cell (RBC) hemolytic assay (HA). The HA assay utilizes the lysis of target RBCs as an indicator of cytotoxicity. Hemolysis is associated with the formation of ion channels through cell membranes by an amphipathic peptide. Previous investigation has indicated that RBC hemolytic activity is more sequence-dependent than lysis of microbial cells, and it has been proposed that two different mechanisms of action are involved in the lysis of microbes and RBCs. Stronger hydrophobic interactions than those required for antimicrobial activity were shown to be necessary for the lysis of RBCs; no hemolytic activity was observed with peptides smaller than 12 residues. This test is a first step in the development of an antimicrobial peptidic agent that can be introduced into the environment with minimal concern for impact on organisms other than the microbial targets. The precursor peptides used to conduct the proof-of-concept testing for the microbial additive described herein have been tested and shown to exhibit no significant hemolysis.

The antimicrobial peptidic additive described herein can be used in-process, in-can and in-film, and can be admixed, layered or added in or as a topcoat to the coating. Since the antimicrobial peptidic additive described herein is a naturally occurring polymer of amino acids, it can be fermented and produced on a commercially feasible basis. The antimicrobial peptidic additive described herein provides polymer chemists with a new arsenal of effective, safe, environmentally sound biocide options.

DEFINITIONS

The terms used herein have their customary and usual meanings, and are intended to encompass at least the following definitions, consistent with their use elsewhere herein:

As used herein other than the claims, the terms "a", "an", "the" and "said" means "at least one" or "one or more."

As used herein in the claim(s), when used in conjunction with the words "comprises" or "comprising," the words "a", "an", "the" or "said" may refer to one or more than one. As used herein "another" may mean at least a second or more.

"Fungus" includes multicellular and unicellular organisms in the fungus family, including the true fungi, molds, mildews and yeasts. "Mold" is sometimes used herein as a synonym for fungi, where the context permits, especially when referring to indoor contaminants. However, the term "mold" also, and more specifically, denotes certain types of fungi. For example, the plasmodial slime molds, the cellular slime molds, water molds, and the everyday common mold. True molds are filamentous fungi consisting of the mycelium, specialized, spore-bearing structures called conidiophores, and conidia (spores). "Mildew" is another common name for certain fungi, including the powdery mildews and the downy mildews. "Yeasts" are unicellular members of the fungus family. For the purposes of the present disclosure, where any of the terms fungus, mold, mildew and yeast is used, the others are implied where the context permits.

"Building materials" include, but are not limited to, conventional and non-conventional indoor and outdoor construction and decorative materials, such as wood, drywall (wallboard), paper or vinyl coated wallboard, fabrics (textiles), carpet, leather, ceiling tiles, cellulose resin wall board (fiberboard), stone, brick, concrete, unglazed tile, stucco, grout, painted surfaces, roofing tiles, shingles, and other materials that are cellulose-rich, or are capable of providing nutrients to fungi, or are capable of harboring nutrient materials and supporting fungal infestation.

"Bioactive" means having an effect on a living organism, especially fungal cells, when the context allows.

An "antifungal peptide" refers specifically to a contiguous amino acid sequence from 3 to 100 amino acid residues in length, including all intermediate ranges, and which is capable of exerting antifungal activity, as defined above. For simplicity, where the context permits, the term "antifungal peptide" also refers to antifungal polypeptides (i.e., a contiguous amino acid sequence from 101 to 10,000 amino acid residues in length, including all intermediate ranges, and antifungal proteins which are proteinaceous molecules having a contiguous amino acid sequence of more than 10,000 amino acid residues length. Preferably such peptides, polypeptides and proteins are not encoded by the genome of an organism.

"Antifungal peptidic agent" refers to a peptide, polypeptide or protein having the ability to inhibit the growth of one or more genera and/or species of fungi. It is also intended to encompass mixtures of such peptides, polypeptides and proteins, together with any associated stabilizers, carriers, and inactive peptides/polypeptides/proteins. Where the context allows, the term "antifungal peptidic agent" may also refer to a peptide library aliquot containing a mixture of peptides in which at least two of the N-terminal amino acid residues are known. If the peptidic agent is a mixture of peptides, at least one will have antifungal activity.

"Antifungal activity" refers to inhibition of fungal cell attachment and/or growth, and is may also refer to fungal cell killing, as the context permits. Accordingly, some antifungal peptidic agents can also be denoted as "fungistatic agents" or "fungicides."

"Inhibition of fungal growth" refers to cessation or reduction of fungal cell proliferation, and can also include inhibition of expression of cellularly produced proteins in static fungal cell colonies. Such inhibition can provide or facilitate disinfection, decontamination or sanitization of inanimate objects, which refer to the process of reducing the number of fungus microorganisms to levels that no longer pose a threat (e.g., to property or human health). Use of a bioactive antifungal agent can be accompanied by manual removal of mold-contaminated building materials, in some instances.

The term "biocide" as used herein refers to a substance that kills microorganisms and their spores. Depending on the type of microorganism killed, a biocidal substance may be further defined as a bactericide, fungicide, or algaecide. The term "biostatic" refers to a substance that prevents the growth of the microorganism and its spores, and encompasses bacteristatic, fungistatic and algaestatic compounds.

A "fungicide" is a biocidal substance used to kill or inactivate a specific microbial group, the fungi. The term "fungistatic," is used to denote substances that prevent fungal microorganisms from growing or reproducing, but do not result in substantial inactivation or killing.

An "effective amount" refers to a concentration of antifungal peptide that is capable of exerting the desired antifungal effect, as defined above.

An "inanimate object" refers to structures and objects other than living organisms. Examples of inanimate objects are architectural structures having painted or unpainted surfaces such as the exterior and interior walls of buildings, industrial equipment, outdoor sculptures and furniture, construction materials for indoor or outdoor use, such as wood, stone, brick, wall board (drywall), ceiling tiles, concrete, unglazed tile, stucco, grout, roofing tiles, shingles, painted or treated wood, synthetic composite materials, leather and textiles.

A "base" or "substrate" refers to any surface that can potentially support the infestation and/or growth of a fungus or spore under favorable conditions for such infestation or growth. It is intended to include exterior surfaces of objects as well as interior surfaces of porous and semiporous objects (e.g., high surface area porous stone structures), constitutes a surface on which a coating can be directly applied and/or impregnated.

The term "coating" has its usual meaning and specifically includes the process of applying (e.g., brushing, dipping, spreading, spraying) or otherwise producing a coated surface, which may also be referred to as a coating, coat, covering, film or layer on a surface.

Where the context so indicates, the term "coating" may instead refer to the coating composition or mixture that is applied. For example, a coating composition may be capable of undergoing a change from a fluent to a nonfluent condition by removal of solvents, vehicles or carriers, by setting, by chemical reaction or conversion, or by solidification from a molten state. The coating or film that is formed may be hard or soft, elastic or inelastic, permanent or transitory. Where the context allows, the act of coating also includes impregnating a surface or object by causing a coating material to extend or penetrate into the object, or into the interstices of a porous, cellular or foraminous material. The general composition and properties of conventional coating materials are described in U.S. patent application Ser. No. 10/655,345 filed Sep. 4, 2003, which is hereby incorporated herein by reference. Additionally, the use of the term "coating" ("coat," "surface coat," "surface coating") is also intended to be consistent with its use in PAINT and Coating Testing Manual, Fourteenth Edition of the Gardner-Sward Handbook (Koleske, J. V. Ed.), p. 696, 1995; and in "ASTM Book of Standards, Volume 06.01, Paint—Tests for Chemical, Physical, and Optical Properties; Appearance," D16-00, 2002, i.e., "a liquid, liquefiable or mastic composition that is converted to a solid protective, decorative, or functional adherent film after application as a thin layer." Examples of a coating include a clear coating and a paint.

A "paint" generally refers to a "pigmented liquid, liquefiable or mastic composition designed for application to a substrate in a thin layer which is converted to an opaque solid film after application. Used for protection, decoration or identification, or to serve some functional purpose such as the filling or concealing of surface irregularities, the modification of light and heat radiation characteristics, etc," [Paint and Coating Testing Manual, Fourteenth Edition of the Gardner-Sward Handbook (Koleske, J. V. Ed.), p. 696, 1995]. Surface treatments, particularly coatings and paints, have been described in U.S. patent application Ser. No. 10/655,345 filed Sep. 4, 2003.

"Elastomers" or rubbers are polymers that can undergo large, but reversible, deformations upon a relatively low physical stress. Elastomers (e.g., tire rubbers, polyurethane elastomers, polymers ending in an anionic diene, segmented polyerethane-urea copolymers, diene triblock polymers with styrene-alpha-methylstyrene copolymer end blocks, poly (p-methylstyrene-b-p-methylstyrene), polydimethylsiloxane-vinyl monomer block polymers, chemically modified natural rubber, polymers from hydrogenated polydienes, polyacrylic elastomers, polybutadienes, trans-polyisoprene, polyisobutene, cis-1,4-polybutadiene, polyolefin thermoplastic elastomers, block polymers, polyester thermoplastic elastomer, thermoplastic polyurethane elastomers) and techniques of elastomer synthesis and elastomer property analysis have been described, for example, in Walker, B. M., ed., Handbook of Thermoplastic Elastomers, Van Nostrand Reinhold Co., New York, 1979; Holden, G., ed., et. al., Thermoplastic Elastomers, 2nd Ed., Hanser Publishers, Verlag, 1996.

An "adhesive" is a composition that is capable of uniting, bonding or holding at least two surfaces together, preferably in a strong and permanent manner (e.g., glue, cement, paste).

A "sealant" is a composition capable of attaching to at least two surfaces, filling the space between them to provide a barrier or protective coating (e.g., by filling gaps or making a surface nonporous).

A "fungal-prone material" is a substance that is capable of serving as a food source for a fungus, or is a material that contains one or more such substance. For example, in the context of a paint or coating composition, a fungal-prone material may be a binder containing a carbon-based polymer that serves as a nutrient for a fungus.

All patents, published patent applications and other publications cited herein are hereby incorporated herein by reference to the extent that they describe materials and methods supplementary to that set forth herein. One skilled in the art will readily appreciate that the present invention is well adapted to carry out any objects and obtain the ends and advantages mentioned as well as those inherent therein. The preferred antifungal compositions and methods described herein are exemplary and intended to be representative of other embodiments which will be apparent to those skilled in the art in light of the present disclosure. For instance, in light of the present disclosure and representative examples, changes in the disclosed compositions and methods and other uses will occur to those skilled in the respective arts of preparing and using paints and coatings, textile finishes, waxes, elastomers, adhesives and sealants which are encompassed within the spirit of the invention and defined by the scope of the appended claims. The present examples, therefore, are not to be considered as limiting the scope of the present invention.

What is claimed is:

1. A surface coating composition, comprising:
   at least one cysteine-free peptidic antimicrobial agent selected from the group consisting of SEQ ID Nos. 173 and 180-184 and variants of SEQ ID Nos. 173 and 180-184 having one or more functionally equivalent amino acids substituted therein, said substituted amino acids having no more than a +/−2 difference in hydropathic value of the Kyte-Doolittle scale compared to the hydropathic value of the Kyte-Doolittle scale of amino acids in SEQ ID Nos. 173 and 180-184, wherein chiral amino acids of the peptidic agent are L-amino acids; and
   a non-peptidic antimicrobial agent, wherein concentrations of the peptidic and non-peptidic antimicrobial agents are sufficient to synergistically inhibit microbial growth during liquid handling processes to prepare the coating composition, in storage of the coating composition or on an inanimate surface coated with the surface coating composition.

2. The surface coating composition of claim 1, wherein the functional groups of the peptidic antimicrobial agent are chemically unmodified.

\* \* \* \* \*